(12) United States Patent
Triener et al.

(10) Patent No.: US 8,748,789 B2
(45) Date of Patent: *Jun. 10, 2014

(54) ASSAY INSTRUMENT FOR DETECTING OPTICAL SIGNALS FROM SAMPLES

(71) Applicant: Illumina, Inc., San Diego, CA (US)

(72) Inventors: Alexander Triener, San Diego, CA (US); Erik Allegoren, San Diego, CA (US); Wenyi Feng, San Diego, CA (US); Dale Buermann, Hayward, CA (US); Erik Olson, San Diego, CA (US); James Osmus, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/905,633

(22) Filed: May 30, 2013

(65) Prior Publication Data
US 2013/0261028 A1 Oct. 3, 2013

Related U.S. Application Data

(63) Continuation of application No. 13/041,194, filed on Mar. 4, 2011, now Pat. No. 8,481,903.

(60) Provisional application No. 61/311,312, filed on Mar. 6, 2010.

(30) Foreign Application Priority Data

Mar. 4, 2011 (CN) ...................... 2011 2 0058782 U
Mar. 4, 2011 (DE) ...................... 20 2011 003 570 U

(51) Int. Cl.
*G02B 7/04* (2006.01)
(52) U.S. Cl.
USPC .................................... 250/201.2; 250/559.4

(58) Field of Classification Search
USPC ........ 250/201.2, 559.4, 226, 216, 239, 222.1; 356/246, 440; 359/361–363, 385–390; 435/287.2–287.4, 7.1, 6.16–6.19
See application file for complete search history.

(56) References Cited

U.S. PATENT DOCUMENTS 3,285,127 A 11/1966 Horst
3,438,690 A 4/1969 Victor (Continued)

FOREIGN PATENT DOCUMENTS

AT 505 258 A1 12/2008
DE 202007003260 5/2007

(Continued)

OTHER PUBLICATIONS

Baird (RB), "Analyst Day Report", Nov. 7, 2008, 10 pgs.

(Continued)

*Primary Examiner* — Que T Le
(74) *Attorney, Agent, or Firm* — Dean Small; Jason P. Gross; The Small Patent Law Group LLC

(57) ABSTRACT

An optical system configured to detect optical signals during imaging sessions. The optical system includes an objective lens that has a collecting end that is positioned proximate to a sample and configured to receive optical signals therefrom. The optical system also includes a removable path compensator that is configured to be located at an imaging position between the collecting end of the objective lens and the sample. The path compensator adjusts an optical path of the light emissions when in the imaging position. Also, the optical system includes a transfer device that is configured to move the path compensator. The transfer device locates the path compensator at the imaging position for a first imaging session and removes the path compensator from the imaging position for a second imaging session.

20 Claims, 32 Drawing Sheets

(56) References Cited

U.S. PATENT DOCUMENTS

| | | | |
|---|---|---|---|
| 5,548,441 | A | 8/1996 | Greenberg |
| 6,266,459 | B1 | 7/2001 | Walt |
| 6,355,431 | B1 | 3/2002 | Chee |
| 6,518,068 | B1 | 2/2003 | Gambini et al. |
| 6,770,441 | B2 | 8/2004 | Dickinson |
| 6,859,570 | B2 | 2/2005 | Walt |
| 7,057,026 | B2 | 6/2006 | Barnes et al. |
| 7,106,513 | B2 | 9/2006 | Moon et al. |
| 7,164,533 | B2 | 1/2007 | Moon |
| 7,211,414 | B2 | 5/2007 | Hardin |
| 7,295,316 | B2 | 11/2007 | Boege et al. |
| 7,315,019 | B2 | 1/2008 | Turner |
| 7,329,492 | B2 | 2/2008 | Hardin |
| 7,329,860 | B2 | 2/2008 | Feng |
| 7,399,643 | B2 | 7/2008 | Moon et al. |
| 7,405,281 | B2 | 7/2008 | Xu et al. |
| 7,622,294 | B2 | 11/2009 | Walt et al. |
| 7,830,575 | B2 | 11/2010 | Moon et al. |
| 7,914,734 | B2 | 3/2011 | Livingston |
| 7,924,515 | B2 | 4/2011 | Plangger |
| 7,932,504 | B2 * | 4/2011 | Yamada ............... 250/461.2 |
| 8,005,314 | B2 | 8/2011 | Ortyn et al. |
| 8,343,746 | B2 | 1/2013 | Rank et al. |
| 2005/0227252 | A1 | 10/2005 | Moon et al. |
| 2009/0027914 | A1 | 1/2009 | Wu et al. |
| 2010/0087325 | A1 | 4/2010 | Buermann |
| 2010/0157086 | A1 | 6/2010 | Segale et al. |

FOREIGN PATENT DOCUMENTS

| | | |
|---|---|---|
| WO | WO 91/06678 A1 | 5/1991 |
| WO | WO 00/63437 A2 | 10/2000 |
| WO | WO 2004/018497 A2 | 3/2004 |
| WO | WO 2004/024328 A1 | 6/2004 |
| WO | WO 2005/033681 A1 | 4/2005 |
| WO | WO 2007/123744 A2 | 11/2007 |
| WO | WO 2009/137435 A1 | 11/2009 |

OTHER PUBLICATIONS

Barclays Capital, "Analyst Day Report-Barclays Capital", Nov. 7, 2008, 8 pgs.

Bentley, David R., et al. Accurate Whole Human Genome Sequencing Using Reversible Terminator Chemistry; Nature; article; vol. 456; Nov. 2008; p. 53-59.

Caris & Co., "Analyst Day Report—Caris & Co.," Nov. 7, 2008, 2 pgs.

Caris & Co., "ILMN-Analyst Day Dazzles Again; Two New Product Unveilings; Dx Strategy Better Articulated," Analyst Research Report Snapshot, Nov. 7, 2008; 2 pgs.

Cowen, "Analyst Day Report—Cowen," Nov. 7, 2008, 9 pgs.

Deutsche Bank, "Analyst Day Report—Deutsche Bank," Nov. 7, 2008, 10 pgs.

International Search Report and Written Opinion of the International Searching Authority in International Application No. PCT/US2011/027271, dated Jul. 7, 2011, 18 pgs.

JP Morgan, "Analyst Day Report—JP Morgan," Nov. 7, 2008, 7 pgs.

Karow, Julia, "Illumina to Launch Sequencing Module for iScan this Year; Other Techs in the Works," Genome Web, http://www.genomeweb.com/print/910407, Jan. 20, 2009, 3 pgs.

Leerink Swann, "Analyst Day Report—Leerink Swann," Nov. 7, 2008, 7 pgs.

Merrill Lynch, "Analyst Day Report—Merrill Lynch," Nov. 7, 2008, 7 pgs.

Pacific Growth Equities, "Analyst Day Report—Pacific Growth Equities," Nov. 7, 2008, 9 pgs.

Piper Jaffray; "Go Big or Go Home: Bold Diagnostics Strategy Unveiled at Analyst Day;" Nov. 7, 2008; 5 pgs.

Winnick, Edward et al. "Illumina Delays Launch of 'Harmonia' Sequencing Module for iScan System," Genome Web, http://www.genomeweb.com/print/924331, Sep. 23, 2009, 2 pgs.

* cited by examiner

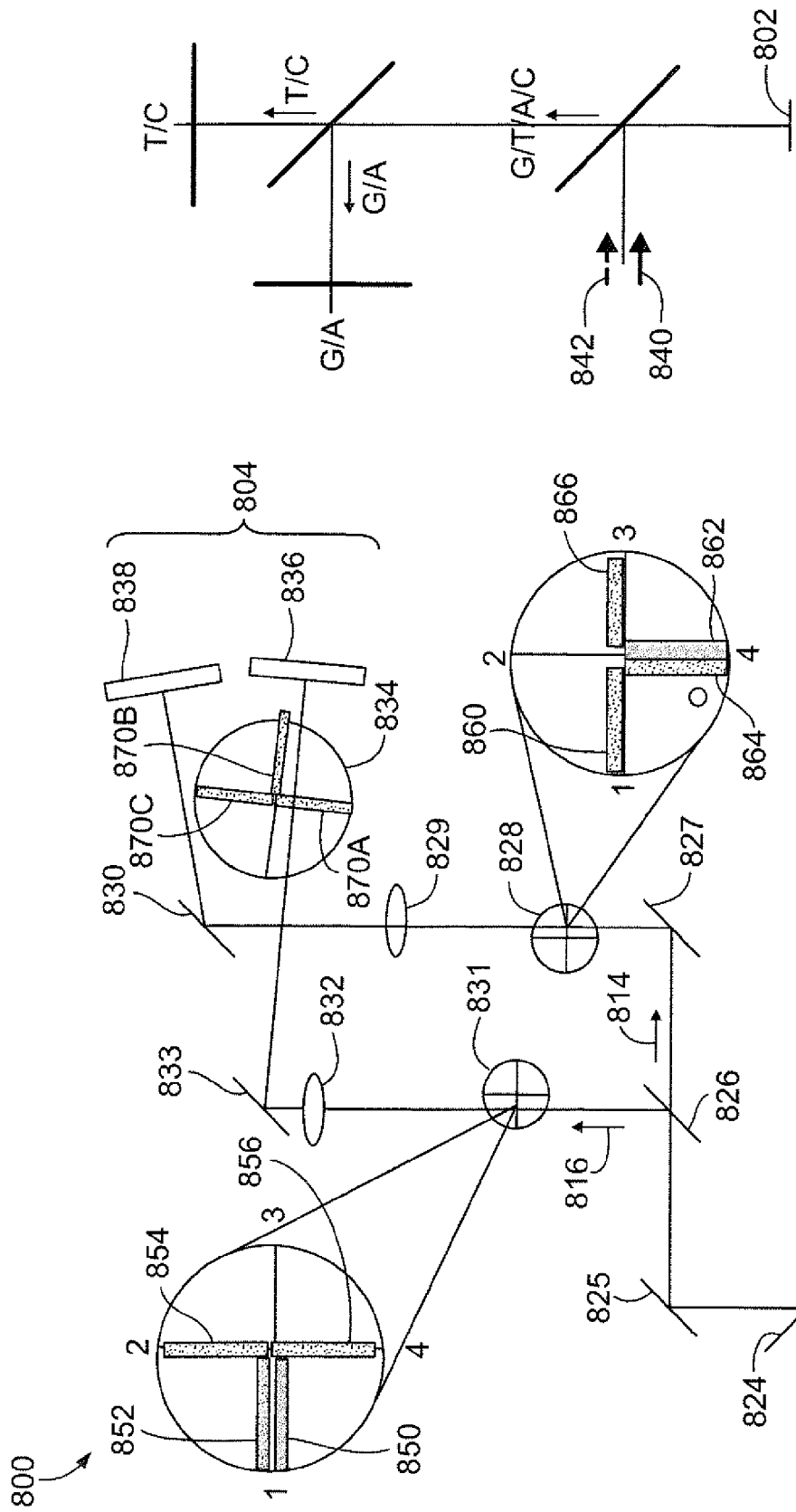

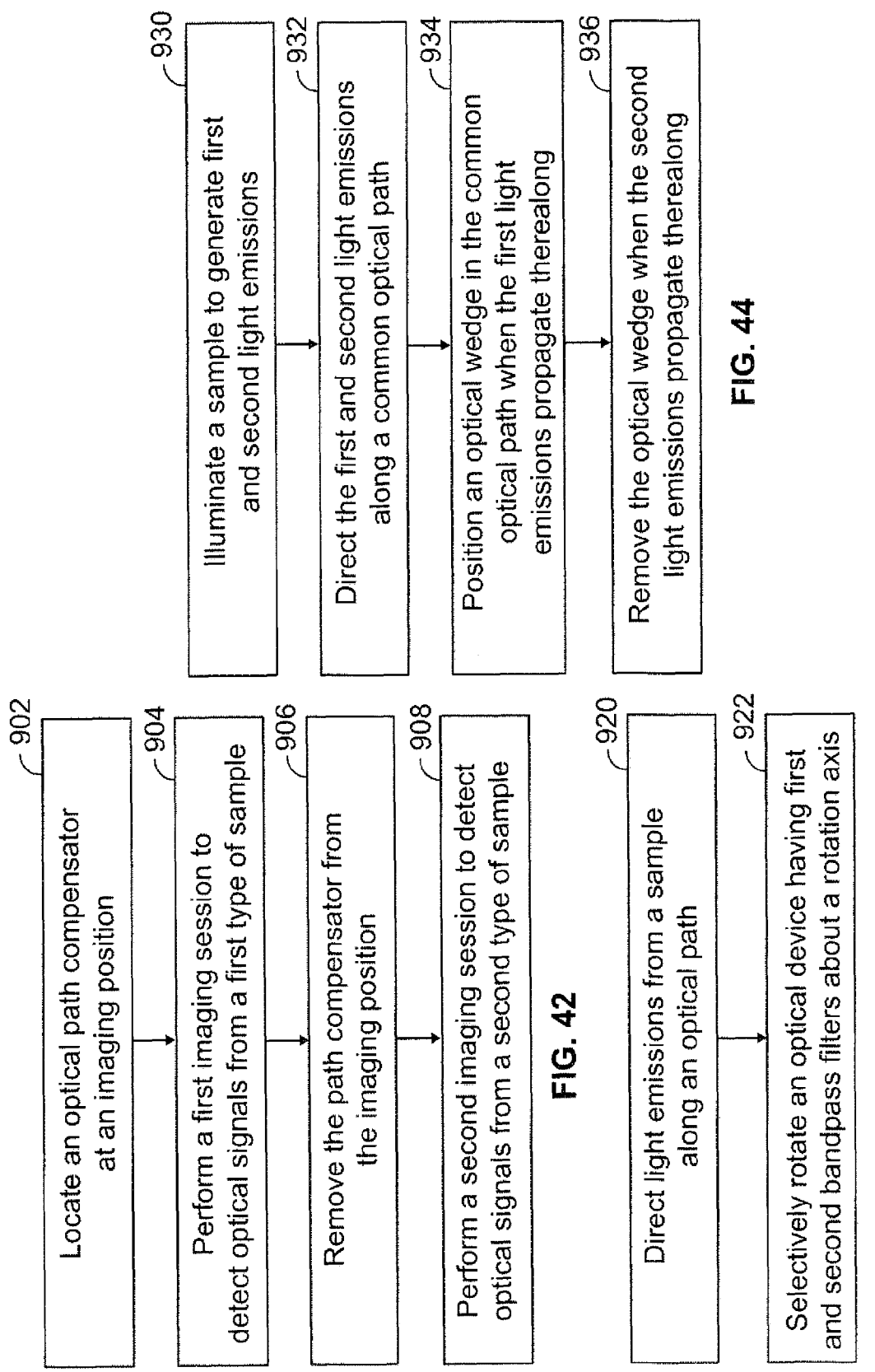

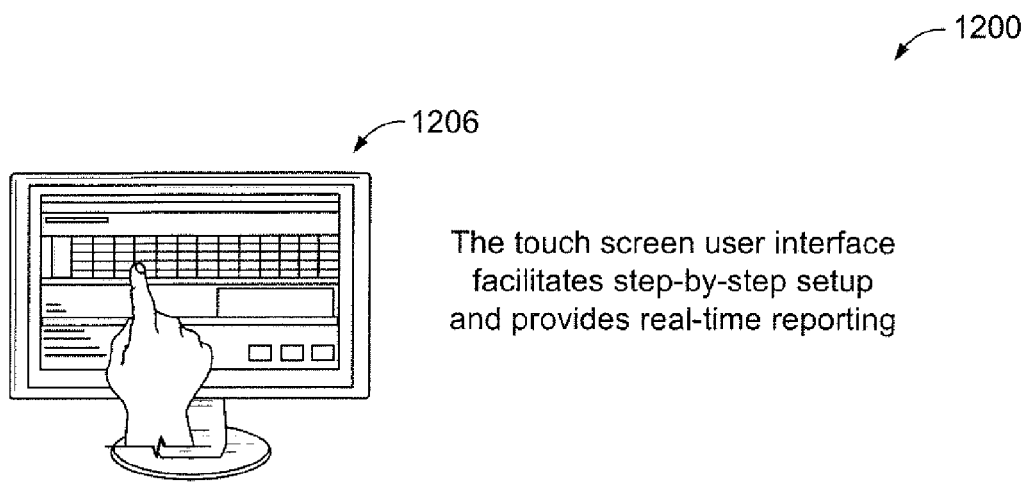
The touch screen user interface facilitates step-by-step setup and provides real-time reporting
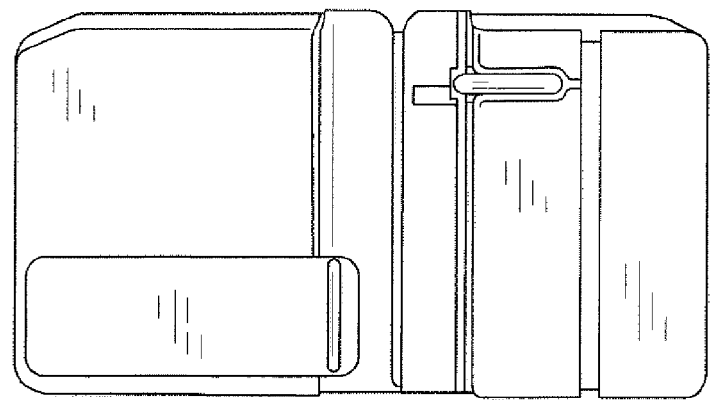
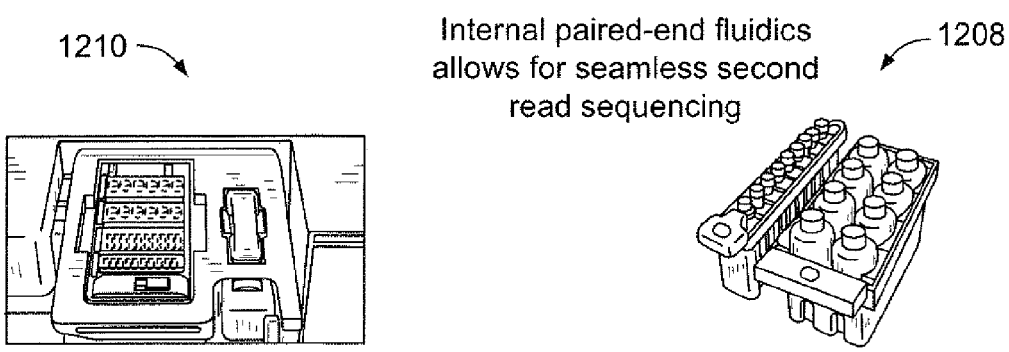
The combo drawer contains dual components for easy array and flow cell loading.
Internal paired-end fluidics allows for seamless second read sequencing
Pre-configured, plug-and-play reagents are ready for up to 200 sequencing cycles.
FIG. 54

ASSAY INSTRUMENT FOR DETECTING OPTICAL SIGNALS FROM SAMPLES

CROSS-REFERENCES TO RELATED APPLICATIONS

The present application is a continuation of U.S. patent application Ser. No. 13/041,194 ("the '194 Application"), filed Mar. 4, 2011, which claims the benefit of U.S. Provisional Application No. 61/311,312 ("the '312 Application"), filed Mar. 6, 2010. Each of the '194 Application and the '312 Application is incorporated by reference in its entirety. The '194 Application also claims the benefit of China Utility Model Application No. 201120058782.6, filed Mar. 4, 2011, and the benefit of German Utility Model Application No. 20 2011 003 570.0, filed Mar. 4, 2011. The German and China utility model applications also claim priority to U.S. Provisional Application No. 61/311,312. Each of the utility model applications is also incorporated by reference in its entirety.

International Application No. PCT/US11/27271, which was filed on the same day as the present application, is also incorporated by reference in its entirety. The international application also claims priority to the U.S. Provisional Application No. 61/311,312.

BACKGROUND OF THE INVENTION

Embodiments of the present invention relate generally to biological or chemical analysis and more particularly, to systems and methods that are configured to detect optical signals from one or more samples of interest.

Various assay protocols used for biological or chemical research are concerned with performing a large number of controlled reactions. In some cases, the controlled reactions are performed on support surfaces or within predefined reaction volumes. The desired reactions may then be observed and analyzed to help identify properties or characteristics of the chemicals involved in the desired reaction. For example, in some protocols, a chemical moiety that includes an identifiable label (e.g., fluorescent label) may selectively bind to another chemical moiety under controlled conditions. These chemical reactions may be observed by exciting the labels with radiation and detecting light emissions from the labels.

Examples of such protocols include DNA sequencing and multiplex array-based assays. In one sequencing-by-synthesis (SBS) protocol, clusters of clonal amplicons are formed through bridge PCR on a surface of a flow cell channel. After generating the clusters of clonal amplicons, the amplicons may be "linearized" to make single stranded DNA (sstDNA). A series of reagents is flowed into the flow cell to complete a cycle of sequencing. Each sequencing cycle extends the sstDNA by a single nucleotide (e.g., A, T, G, C) having a unique fluorescent label. Each nucleotide has a reversible terminator that allows only a single-base incorporation to occur in one cycle. After nucleotides are added to the sstDNAs clusters, an image in four channels is taken (i.e., one for each fluorescent label). After imaging, the fluorescent label and the terminator are chemically cleaved from the sstDNA and the growing DNA strand is ready for another cycle. Several cycles of reagent delivery and optical detection can be repeated to determine the sequences of the clonal amplicons.

In some multiplex array-based assay protocols, populations of different probe molecules are immobilized to a substrate surface. The probes may be differentiated based on each probe's address on the substrate surface. For example, each population of probe molecules may have a known location (e.g., coordinates on a grid) on the substrate surface. The probe molecules are exposed to target analytes under controlled conditions such that a detectable change occurs at one or more addresses due to a specific interaction between a target analyte and the probe. For example, a fluorescently labeled target analyte that binds to a specific probe can be identified based on recruitment of the fluorescent label to the address of the probe. The addresses on the array can be detected by an optical device to identify which populations reacted with the analytes. By knowing the chemical structure of the probe molecules that reacted with the analytes, properties of the analyte may be determined. In other multiplex assays, desired reactions are conducted on surfaces of individually identifiable microparticles that may also be scanned and analyzed. Typically, multiplex array-based assays do not require repeated delivery of fluids and, thus, detection can be carried out on an open-face substrate without a flow cell.

Different assay protocols, such as those described above, may include particular features or involve particular steps that do not occur in other assay protocols. For example, different assay protocols may use different types of reagents or reagents having unique modifications, labels with different emission spectra, types of optical substrates for supporting the samples (e.g., flow cells, open-face substrates, microarrays, wells, microparticles), light sources with different excitation spectra, different optical components (e.g., objective lenses), thermal conditions, and software. Furthermore, the devices typically operate at a high level precision since detection occurs at a resolution of a few microns or less. As a result, research platforms that exist today are generally concerned with performing only one type of assay protocol.

Accordingly, there is a need for systems capable of performing more than one assay protocol. There is also a need for optical components that facilitate performing more than one assay protocol. There is also a general need for alternative systems, methods, and optical components that may be used in performing one or more assay protocols.

BRIEF DESCRIPTION OF THE INVENTION

In accordance with one embodiment, an optical system is provided that is configured to detect optical signals during imaging sessions. The optical system includes an objective lens that has a collecting end that is positioned proximate to a sample and configured to receive optical signals therefrom. The optical system also includes a removable path compensator that is configured to be located at an imaging position between the collecting end of the objective lens and the sample. The path compensator adjusts an optical path of the light emissions when in the imaging position. Also, the optical system includes a transfer device that is configured to move the path compensator. The transfer device locates the path compensator at the imaging position for a first imaging session and removes the path compensator from the imaging position for a second imaging session.

In another embodiment, a method of operating an optical system is provided. The optical system has an objective lens that is configured to receive optical signals from a sample that is located proximate to a focal region of the optical system. The method includes locating a path compensator at an imaging position proximate to a collecting end of the objective lens. The path compensator adjusts an optical path of the optical signals propagating therethrough when in the imaging position. The method also includes performing a first imaging session and removing the path compensator from the imaging position. The method further includes performing a second imaging session.

In yet another embodiment, an optical system configured to detect optical signals from a sample is provided. The optical system includes an optical train including an objective lens that is configured to receive the optical signals. The optical system also includes a sample detector that is configured to detect the optical signals. The optical signals are directed by the optical train along an optical path between the sample detector and the objective lens. The optical system also includes an optical device having a rotation axis and comprising first and second bandpass filters. The first and second bandpass filters have fixed orientations with respect to the rotation axis. The optical device selectively rotates about the rotation axis to position at least one of the first and second bandpass filters within the optical path.

In another embodiment, an optical system configured to detect optical signals from a sample is provided. The optical system includes an optical train including an objective lens configured to receive sample light emissions. The optical system also includes a detector assembly that is configured to detect the optical signals. Portions of the optical signals are directed by the optical train along first and second optical paths between the detector assembly and the objective lens. The optical system also includes first and second optical devices that are located proximate to the first and second optical paths, respectively. Each of the first and second optical devices has a rotation axis and includes a plurality of bandpass filters. The bandpass filters have fixed orientations with respect to the corresponding rotation axis. Each of the first and second optical devices selectively rotates about the corresponding rotation axis to position at least one of the bandpass filters within the corresponding optical path.

In one embodiment, a method of detecting optical signals from a sample is provided. The method includes directing optical signals from a sample along an optical path between an objective lens and a sample detector of the optical system. The method also includes selectively rotating an optical device about a rotation axis. The optical device includes first and second bandpass filters. The first and second bandpass filters have fixed orientations with respect to the rotation axis. At least one of the first and second bandpass filters is positioned within the optical path to filter the light emissions.

In another embodiment, an optical device configured to at least one of redirect and filter optical signals propagating along an optical path is provided. The optical device includes a device body having a rotation axis. The device body is rotatable about the rotation axis. The optical device also includes first and second optical components coupled to the device body. The first and second optical components have fixed orientations with respect to a rotation axis. The optical device also includes a motor operatively coupled to the device body. The motor selectively rotates the first and second optical components about the rotation axis to position at least one of the first and second optical components within the optical path.

In another embodiment, an optical system is provided that includes a sample detector that is configured to detect optical signals from a sample. The optical signals include first and second optical signals having different emission spectra. The optical system also includes an optical train including an objective lens that is located proximate to the sample and a removable optical wedge. The optical train directs the light emissions along an optical path to the sample detector. The optical system also includes a transfer device that is configured to position the optical wedge in the optical path for detecting the first optical signals and remove the optical wedge from the optical path for detecting the second optical signals. The optical wedge directs the first optical signals when positioned in the optical path so that the first optical signals are incident upon the sample detector. The second optical signals are incident upon the sample detector when the optical wedge is removed from the optical path.

In yet another embodiment, an optical system is provided that includes an excitation light source assembly comprising first and second excitation light sources. The first and second excitation light sources excite a sample during separate first and second imaging sessions, respectively. The sample generates corresponding light emissions when excited by each of the first and second excitation light sources. The optical system also includes a beamsplitter that separates the corresponding light emissions of each of the first and second excitation light sources into reflected and transmitted portions. The transmitted portions of the first and second excitation light sources are directed along a common transmitted optical path. The reflected portions of the first and second excitation light sources are directed along a common reflected optical path. The optical system also includes a plurality of optical wedges. Each of the transmitted and reflected optical paths has an optical wedge that is selectively moveable. The optical wedge of the reflected optical path redirects the reflected portion during the first imaging session and the optical wedge of the transmitted optical path redirects the transmitted portion during the second imaging session.

In another embodiment, a method of operating an optical system is provided that includes illuminating a sample to generate light emissions that include first and second optical signals having different emission spectra. The method also includes directing the first and second optical signals along a common optical path to a sample detector. The directing operation includes positioning an optical wedge in the optical path when the first optical signals propagate therealong. The optical wedge directs the first optical signals so that the first optical signals are incident upon the sample detector. The directing operation also includes removing the optical wedge from the optical path when the second optical signals propagate therealong. The second optical signals are incident upon the sample detector when the optical wedge is removed from the optical path.

In another embodiment, a workstation that is configured to detect optical signals from samples is provided. The samples include first and second types of samples. The workstation includes a detector assembly that is configured to detect the optical signals and an optical assembly that is configured to receive and direct the optical signals to the detector assembly. The optical assembly includes a plurality of selectively moveable optical components. The workstation also includes an excitation light source assembly that has two excitation light sources having different excitation spectra. Furthermore, the workstation includes a protocol module that is configured to subject the first and second types of samples to first and second imaging protocols, respectively. Each of the first and second imaging protocols includes illuminating the corresponding sample with the two excitation light sources and detecting the corresponding light emissions. The workstation also includes an optics adjustment system configured to selectively move the optical components of the optical assembly. The optics adjustment system selectively moves the optical components to a first collective arrangement for the first imaging protocol and a different second collective arrangement for the second imaging protocol.

An assay instrument for detecting optical signals from samples is provided that includes a sample stage having a first interface and a second interface. The first interface includes a platform for holding a sample on an open-faced support and for imaging of an external surface and the second interface includes a platform for holding a sample in a flow cell for imaging of at least one internal surface. The sample stage is coupled with the flow cell with fluidics connectors. The assay instrument also includes an optical detector for detecting optical signals from the open-faced support and flow cell. The assay instrument also includes a moving mechanism for selectively moving one or more optical components including an objective lens in the optical pathway between the sample stage and the optical detector to either a first configuration for surface-imaging of the open-faced support or a second configuration for imaging the flow cell.

An optical assembly for use in an assay instrument to assist the detection of optical signals from a sample during imaging sessions is provided. The optical assembly includes an objective lens that has (i) a collecting end that is positioned proximate to a sample interface on a sample stage and configured to receive optical signals therefrom and (ii) an afocal end configured to transmit the optical signals to a detector. The optical assembly also includes a first removable path compensator for adjusting an optical path of the optical signals when positioned between the collecting end of the objective lens and the sample. The optical assembly also includes a second removable path compensator for adjusting an optical path of the optical signals when located at an afocal position with respect to the objective lens.

In another embodiment, a workstation is provided that is configured to detect optical signals from samples. The samples include first and second types of samples. The workstation includes a detector assembly that is configured to detect the optical signals from first and second types of samples at different sample interfaces on a sample stage. The workstation includes an optical assembly that has an objective lens that is positioned proximate to the sample stage. The optical assembly is configured to receive and direct the optical signals to the detector assembly. The optical assembly has one or a plurality of selectively moveable optical components. The workstation also includes an excitation light source assembly that is positioned proximate to the objective lens and includes two excitation light sources having different excitation spectra. The workstation also has a protocol module that is configured to subject the first and second types of samples to first and second imaging protocols, respectively. Each of the first and second imaging protocols includes illuminating the corresponding sample with the two excitation light sources and detecting the corresponding optical signals. Furthermore, the workstation includes a moving mechanism for selectively moving the optical components of the optical assembly. The moving mechanism is configured to selectively move the optical components to a first configuration for the first imaging protocol and a different second configuration for the second imaging protocol.

BRIEF DESCRIPTION OF THE DRAWINGS

FIGS. 37 and 38 illustrate a top plan view and a diagram, respectively, of an optical assembly formed in accordance with one embodiment.

FIG. 39 illustrates optical signals that are reflected and transmitted by different optical components of the optical assembly of FIG. 38.

FIG. 42 is a block diagram of a method of operating an optical system that has an objective lens configured to receive optical signals from a sample stage.

FIG. 43 is a block diagram of a method of detecting light emissions from a sample.

FIG. 44 is a block diagram of a method of operating an optical system.

FIG. 54 shows various features of the HiScan SQ assay system that a user can interact with.

DETAILED DESCRIPTION OF THE INVENTION

Figure 1:
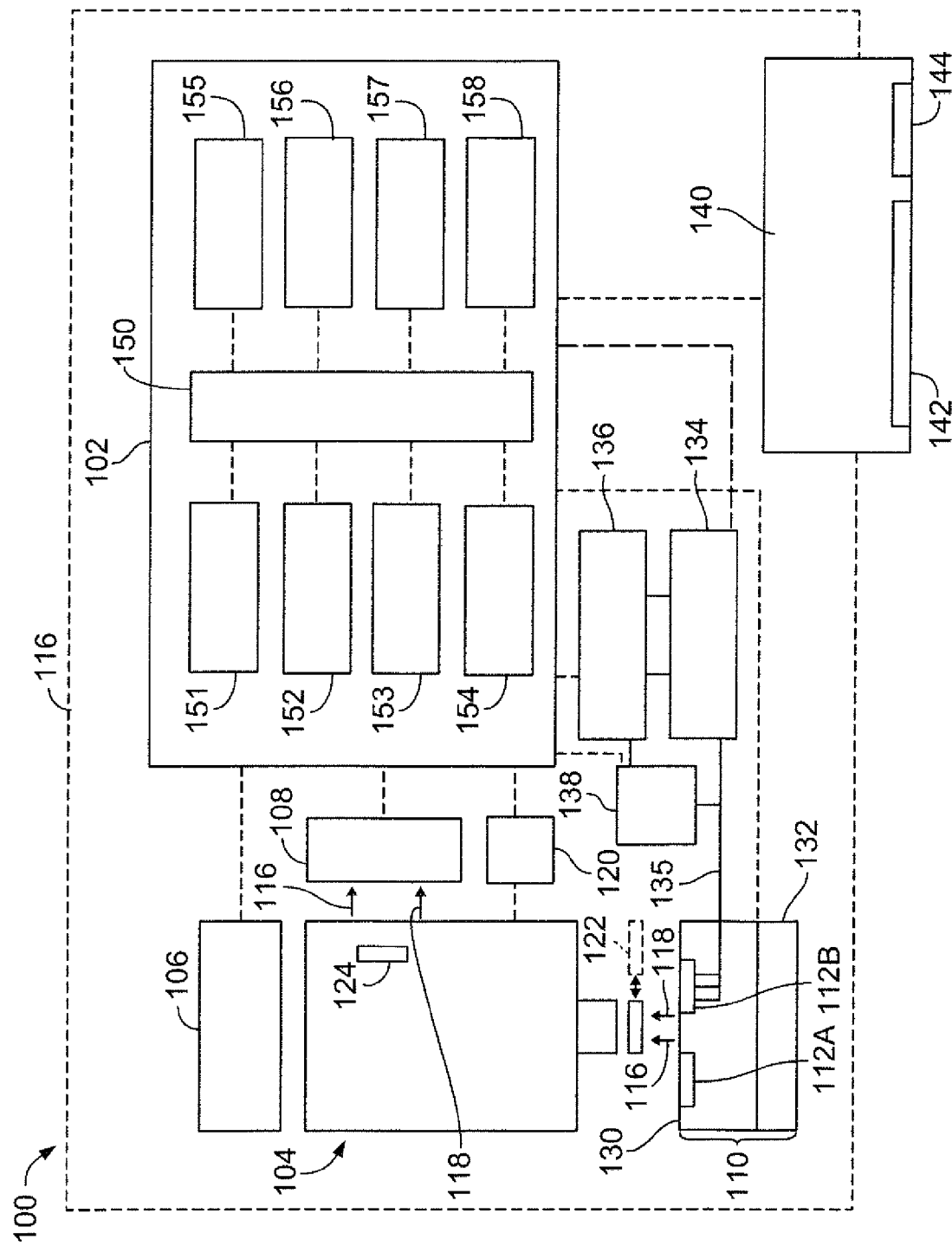
FIG. 1 is a block diagram of a system for biological or chemical analysis formed in accordance with one embodiment.

Embodiments described herein include various systems, assemblies, and apparatuses used to detect optical signals that are provided by samples of interest. The optical signals may be light emissions from labels or may be transmission light that has been reflected or refracted by the sample. Particular embodiments include systems or components of systems that may be used in performing more than one type of assay protocol. For example, embodiments may be used to perform or facilitate performing a sequencing protocol in which sstDNA is sequenced in a flow cell and a scanning protocol in which microarrays are scanned to investigate unknown analytes. However, embodiments described herein are not limited to performing more than one assay protocol and, in some embodiments, may be used to perform only one type of assay protocol.

In particular embodiments, the optical systems include selectively moveable optical components. By moving one or more optical components, the optical system may be adjusted or modified, which may be desirable for various reasons. For example, an optical path taken by the sample optical signals may be adjusted to detect optical signals from a different part (e.g., depth) of the same sample or to calibrate the system. As another example, the optical path may be adjusted to accommodate a different sample. For instance, different support structures that hold the biological matter may have different effects on the optical signals propagating from the biological matter. Furthermore, the optical path may be adjusted by adding or exchanging filters to so that different light emissions can be detected. In yet another example, optical systems may be reconfigured to magnify the image of the samples by inserting an optical component or through pixel binning. Accordingly, the optical components of an optical system or assembly may be reconfigured to have different collective arrangements for different imaging sessions.

As used herein, the phrases "modifying an optical path," "adjusting an optical path," and similar phrases include at least one of redirecting the optical signals through reflection and/or refraction, filtering the optical signals, adjusting an intensity of the optical signals, adjusting a focal region of the optical assembly, modifying a beam shape of the optical signals.

As used herein, the term "optical components" includes various elements that affect the propagation of optical signals. For example, the optical components may at least one of redirect, filter, shape, magnify, or concentrate the optical signals. The optical signals that may be affected include the optical signals that are upstream from the sample and the optical signals that are downstream from the sample. In a fluorescence-detection system, upstream components include those that direct excitation radiation toward the sample and downstream components include those that direct emission radiation away from the sample. Optical components may be, for example, reflectors, dichroics, beam splitters, collimators, lenses, filters, wedges, prisms, mirrors, detectors, and the like. Optical components also include bandpass filters, optical wedges, and optical devices similar to those described herein.

As used herein, the term "optical signals" includes electromagnetic energy capable of being detected. The term includes light emissions from labeled biological or chemical substances and also includes transmitted light that is refracted or reflected by optical substrates. For example, samples may include encoded microparticles that transform the incident light into optical signals that identify the microparticle (or substances immobilized on the microparticles). The transformed optical signals may form a detectable pattern that represents a code of the illuminated microparticle. Optical signals may also include incident light that is directed onto the sample to excite labels or to be reflected/refracted by the sample.

Optical signals, including excitation radiation that is incident upon the sample and light emissions that are provided by the sample, may have one or more spectral patterns. For example, more than one type of label may be excited in an imaging session. In such cases, the different types of labels may be excited by a common excitation light source or may be excited by different excitation light sources that simultaneously provide incident light. Each type of label may emit optical signals having a spectral pattern that is different from the spectral pattern of other labels. For example, the spectral patterns may have different emission spectra. The light emissions may be filtered to separately detect the optical signals from other emission spectra. As used herein, when the term "different" is used with respect to emission spectra, the emission spectra may have wavelength ranges that at least partially overlap so long as at least a portion of one emission spectrum does not completely overlap the other emission spectrum. Different emission spectra may have other characteristics that do not overlap, such as emission anisotropy or fluorescence lifetime. When the light emissions are filtered, the wavelength ranges of the emission spectra may be narrowed.

As described above, the optical components may be selectively moveable. As used herein, when the term "selectively" is used in conjunction with "moving" and similar terms, the phrase means that the position of the optical component may be changed in a desired manner. For example, at least one of the location and the orientation of the optical component may be changed. The phrase "selectively moving" includes removing the optical component from the optical path, adjusting an orientation of the optical component in the optical path (e.g., rotating the optical component), or moving the optical component such that the orientation does not change, but the location of the optical component does change. In particular embodiments, the optical components are selectively moved between imaging sessions. However, in other embodiments, the optical components may be selectively moved during an imaging session.

Different elements and components may be removably coupled. As used herein, when two or more elements or components are "removably coupled" (or "removably engaged") the elements are readily separable without destroying the coupled components. Elements are readily separable when the elements may be separated from each other without undue effort or a significant amount of time spent in separating the components. For example, in some embodiments, a path compensator may be removably coupled to an objective lens numerous times during operation. When removably coupled, the path compensator and objective lens may operate together in a suitable manner for imaging a sample. In particular embodiments, the elements are automatically removably coupled by a machine or system. Furthermore, in some embodiments, the removably coupled elements are directly attached to one another such that some contact is made between the coupled elements. In other embodiments, the removably coupled elements have intervening elements that facilitate removably coupling. For example, the path compensator may be directly attached to a collar that is directly attached to the objective lens. In such a case, the path compensator and the objective lens may not contact each other. Exemplary modes for removably coupling components include, but are not limited to, interactions mediated by magnetism, vacuum, charge, mild adhesives, mechanical clamping or the like.

Imaging sessions include a time period in which at least a portion of the sample is imaged. One sample may undergo or be subject to multiple imaging sessions. For example, one sample may be subject to two different imaging sessions in which each imaging session attempts to detect optical signals from one or more different labels. As a specific example, a first scan along at least a portion of a nucleic acid sample may detect labels associated with nucleotides A and C and a second scan along at least a portion of the sample may detect labels associated with nucleotides G and T. In other embodiments, detecting optical signals in different imaging sessions may include scanning different samples. Different samples may be of the same type (e.g., two microarray chips) or of different types (e.g., a flow cell and a microarray chip).

During an imaging session, optical signals provided by the sample are observed through an optical system. Various types of imaging may be used with embodiments described herein. For example, embodiments may be configured to perform at least one of epi-fluorescent imaging and total-internal-reflectance-fluorescence (TIRF) imaging. In particular embodiments, the sample imager is a scanning time-delay integration (TDI) system. Furthermore, the imaging sessions may include "line scanning" one or more samples such that a linear focal region of light is scanned across the sample(s). Some methods of line scanning are described, for example, in U.S. Pat. No. 7,329,860 and International Publication No. WO 2009/137435, of which the complete subject matter is incorporated herein by reference in their entirety. Imaging sessions may also include moving a point focal region of light in a raster pattern across the sample(s). Alternatively, one or more regions of the sample(s) may be illuminated at one time in a "step and shoot" manner. In other embodiments, imaging sessions may include detecting light emissions that are generated, without illumination, and based entirely on emission properties of a label within the sample (e.g., a radioactive or chemiluminescent component in the sample).

As used herein, the term "sample" includes various matters of interest that undergo an imaging session where optical signals from the sample are observed. In particular embodiments, a sample may include biological or chemical substances of interests and, optionally, an optical substrate or support structure that supports the biological or chemical substances. As such, a sample may or may not include an optical substrate or support structure. As used herein, the term "biological or chemical substances" may include a variety of biological or chemical substances that are suitable for being imaged or examined with the optical systems described herein. For example, biological or chemical substances include biomolecules, such as nucleosides, nucleic acids, polynucleotides, oligonucleotides, proteins, enzymes, polypeptides, antibodies, antigens, ligands, receptors, polysaccharides, carbohydrates, polyphosphates, nanopores, organelles, lipid layers, cells, tissues, organisms, and biologically active chemical compound(s) such as analogs or mimetics of the aforementioned species. Other chemical substances include labels that can be used for identification, examples of which include fluorescent labels and others set forth in further detail below.

Different types of samples may include different optical substrates or support structures that affect incident light in different manners. In particular embodiments, samples to be detected can be attached to one or more surfaces of a substrate or support structure. For example, open-face substrates (such as some microarrays and chips) have biological or chemical substances immobilized to an exterior surface of the open-face substrate. As such, optical signals to be detected are projected from an exterior surface through air and perhaps through liquid having different indices of refraction when the optical signals are collected from above. However, flow cells or capillary flow optical substrates may include one or more flow channels. In flow cells, the flow channels may be separated from the surrounding environment by top and bottom layers of the flow cell. Thus, optical signals to be detected are projected from within the support structure and may transmit through multiple layers of material having different refractive indices. For example, when detecting optical signals from an inner bottom surface of a flow channel and when detecting optical signals from above the flow channel, the optical signals that are desired to be detected may propagate through a fluid having an index of refraction, through one or more layers of the flow cells having different indices of refraction, and through the ambient environment having a different index of refraction. Accordingly, the optical signals propagating from the open-face substrate may be affected differently than the optical signals propagating from a surface of the flow channel. In such cases, embodiments described herein may facilitate adjusting or modifying the optical assembly (or train) that directs the optical signals from the sample to the detector assembly.

Different types of optical substrates or solid support structures used in a method, system, or apparatus set forth herein can have various compositions and properties. Substrates and support structures can differ from each other with regard to, for example, type of material (e.g., glass, plastic), a thickness of the solid material, spacing of a gap between solid material layers, number of solid material layers in which the solid material layers may comprise the same or different materials, number of gaps between solid material layers, chemical nature of gases or liquids in contact with one or more solid material layers, refractive index of the solid material, refractive index of liquid in contact with a solid material layer, and the like. In some embodiments, the optical substrate may include a gel that supports the biological substances and permits optical signals to transmit therethrough.

In some embodiments, different types of samples may also include the same support structures and biological substances, but have labels that emit optical signals at different emission spectra. In such cases, it may be better to adjust or modify the optical components of the optical assembly to improve the detection of the optical signals. More specifically, optical signals having different emission spectra may be directed differently by the optical components due to chromatic aberration.

Optical substrates or support structures include flow cells having flow channels where, for example, nucleic acids are sequenced. In other embodiments, optical substrates may include one or more slides, open-face substrates or planar chips (such as those used in microarrays), or microparticles. In such cases where the optical substrate includes a plurality of microparticles that support the biological or chemical substances, the microparticles may be held by another optical substrate, such as a slide, array of pits, or grooved plate. In particular embodiments, the optical substrate includes diffraction grating based encoded optical identification elements similar to or the same as those described in pending U.S. patent application Ser. No. 10/661,234, entitled Diffraction Grating Based Optical Identification Element, filed Sep. 12, 2003, which is incorporated herein by reference in its entirety, discussed more hereinafter. A bead cell or plate for holding the optical identification elements may be similar to or the same as that described in pending U.S. patent application Ser. No. 10/661,836, entitled "Method and Apparatus for Aligning Microbeads in Order to Interrogate the Same", filed Sep. 12, 2003, and U.S. Pat. No. 7,164,533, entitled "Hybrid Random Bead/Chip Based Microarray", issued Jan. 16, 2007, as well as U.S. patent application Ser. No. 60/609,583, entitled "Improved Method and Apparatus for Aligning Microbeads in Order to Interrogate the Same", filed Sep. 13, 2004, Ser. No. 60/610,910, entitled "Method and Apparatus for Aligning Microbeads in Order to Interrogate the Same", filed Sep. 17, 2004, each of which is incorporated herein by reference in its entirety.

Optical systems described herein may also be used to scan samples that include microarrays. A microarray may include a population of different probe molecules that are attached to one or more substrates such that the different probe molecules can be differentiated from each other according to relative location. An array can include different probe molecules, or populations of the probe molecules, that are each located at a different addressable location on a substrate. Alternatively, a microarray can include separate optical substrates, such as beads, each bearing a different probe molecule, or population of the probe molecules, that can be identified according to the locations of the optical substrates on a surface to which the substrates are attached or according to the locations of the substrates in a liquid. Exemplary arrays in which separate substrates are located on a surface include, without limitation, a BeadChip Array available from Illumina® Inc. (San Diego, Calif.) or others including beads in wells such as those described in U.S. Pat. Nos. 6,266,459, 6,355,431, 6,770,441, 6,859,570, and 7,622,294; and PCT Publication No. WO 00/63437, each of which is hereby incorporated by reference. Other arrays having particles on a surface include those set forth in US 2005/0227252; WO 05/033681; and WO 04/024328, each of which is hereby incorporated by reference.

Any of a variety of microarrays known in the art, including, for example, those set forth herein, can be used. A typical microarray contains sites, sometimes referred to as features, each having a population of probes. The population of probes at each site is typically homogenous having a single species of probe, but in some embodiments the populations can each be heterogeneous. Sites or features of an array are typically discrete, being separated with spaces between each other. The size of the probe sites and/or spacing between the sites can vary such that arrays can be high density, medium density or lower density. High density arrays are characterized as having sites separated by less than about 15 μm. Medium density arrays have sites separated by about 15 to 30 μm, while low density arrays have sites separated by greater than 30 μm. An array useful in the invention can have sites that are separated by less than 100 μm, 50 μm, 10 μm, 5 μm, 1 μm, or 0.5 μm. An apparatus or method of an embodiment of the invention can be used to image an array at a resolution sufficient to distinguish sites at the above densities or density ranges.

Further examples of commercially available microarrays that can be used include, for example, an Affymetrix® GeneChip® microarray or other microarray synthesized in accordance with techniques sometimes referred to as VLSIPS™ (Very Large Scale Immobilized Polymer Synthesis) technologies as described, for example, in U.S. Pat. Nos. 5,324,633; 5,744,305; 5,451,683; 5,482,867; 5,491,074; 5,624,711; 5,795,716; 5,831,070; 5,856,101; 5,858,659; 5,874,219; 5,968,740; 5,974,164; 5,981,185; 5,981,956; 6,025,601; 6,033,860; 6,090,555; 6,136,269; 6,022,963; 6,083,697; 6,291,183; 6,309,831; 6,416,949; 6,428,752 and 6,482,591, each of which is hereby incorporated by reference. A spotted microarray can also be used in a method according to an embodiment of the invention. An exemplary spotted microarray is a CodeLink™ Array available from Amersham Biosciences. Another microarray that is useful is one that is manufactured using inkjet printing methods such as SurePrint™ Technology available from Agilent Technologies.

The systems and methods set forth herein can be used to detect the presence of a particular target molecule in a sample contacted with the microarray. This can be determined, for example, based on binding of a labeled target analyte to a particular probe of the microarray or due to a target-dependent modification of a particular probe to incorporate, remove, or alter a label at the probe location. Any one of several assays can be used to identify or characterize targets using a microarray as described, for example, in U.S. Patent Application Publication Nos. 2003/0108867; 2003/0108900; 2003/0170684; 2003/0207295; or 2005/0181394, each of which is hereby incorporated by reference.

Furthermore, optical systems described herein may be constructed to include various components and assemblies as described in PCT application PCT/US07/07991, entitled "System and Devices for Sequence by Synthesis Analysis", filed Mar. 30, 2007 and/or to include various components and assemblies as described in International Publication No. WO 2009/042862, entitled "Fluorescence Excitation and Detection System and Method", filed Sep. 26, 2008, both of which the complete subject matter are incorporated herein by reference in their entirety. In particular embodiments, optical systems can include various components and assemblies as described in U.S. Pat. No. 7,329,860 and WO 2009/137435, of which the complete subject matter is incorporated herein by reference in their entirety. Optical systems can also include various components and assemblies as described in U.S. patent application Ser. No. 12/638,770, filed on Dec. 15, 2009, of which the complete subject matter is incorporated herein by reference in its entirety.

In particular embodiments, methods, and optical systems described herein may be used for sequencing nucleic acids. For example, sequencing-by-synthesis (SBS) protocols are particularly applicable. In SBS, a plurality of fluorescently labeled modified nucleotides are used to sequence dense clusters of amplified DNA (possibly millions of clusters) present on the surface of an optical substrate (e.g., a surface that at least partially defines a channel in a flow cell). The flow cells may contain nucleic acid samples for sequencing where the flow cells are placed within the appropriate flow cell holders. The samples for sequencing can take the form of single nucleic acid molecules that are separated from each other so as to be individually resolvable, amplified populations of nucleic acid molecules in the form of clusters or other features, or beads that are attached to one or more molecules of nucleic acid. The nucleic acids can be prepared such that they comprise an oligonucleotide primer adjacent to an unknown target sequence. To initiate the first SBS sequencing cycle, one or more differently labeled nucleotides, and DNA polymerase, etc., can be flowed into/through the flow cell by a fluid flow subsystem (not shown). Either a single type of nucleotide can be added at a time, or the nucleotides used in the sequencing procedure can be specially designed to possess a reversible termination property, thus allowing each cycle of the sequencing reaction to occur simultaneously in the presence of several types of labeled nucleotides (e.g. A, C, T, G). The nucleotides can include detectable label moieties such as fluorophores. Where the four nucleotides are mixed together, the polymerase is able to select the correct base to incorporate and each sequence is extended by a single base. Nonincorporated nucleotides can be washed away by flowing a wash solution through the flow cell. One or more lasers may excite the nucleic acids and induce fluorescence. The fluorescence emitted from the nucleic acids is based upon the fluorophores of the incorporated base, and different fluorophores may emit different wavelengths of emission light. A deblocking reagent can be added to the flow cell to remove reversible terminator groups from the DNA strands that were extended and detected. The deblocking reagent can then be washed away by flowing a wash solution through the flow cell. The flow cell is then ready for a further cycle of sequencing starting with introduction of a labeled nucleotide as set forth above. The fluidic and detection steps can be repeated several times to complete a sequencing run. Exemplary sequencing methods are described, for example, in Bentley et al., Nature 456:53-59 (2008), WO 04/018497; U.S. Pat. No. 7,057,026; WO 91/06678; WO 07/123,744; U.S. Pat. No. 7,329,492; U.S. Pat. No. 7,211,414; U.S. Pat. No. 7,315,019; U.S. Pat. No. 7,405,281, and US 2008/0108082, each of which is incorporated herein by reference.

In some embodiments, nucleic acids can be attached to a surface and amplified prior to or during sequencing. For example, amplification can be carried out using bridge amplification. Useful bridge amplification methods are described, for example, in U.S. Pat. No. 5,641,658; U.S. Patent Publ. No. 2002/0055100; U.S. Pat. No. 7,115,400; U.S. Patent Publ. No. 2004/0096853; U.S. Patent Publ. No. 2004/0002090; U.S. Patent Publ. No. 2007/0128624; and U.S. Patent Publ. No. 2008/0009420. Another useful method for amplifying nucleic acids on a surface is rolling circle amplification (RCA), for example, as described in Lizardi et al., Nat. Genet. 19:225-232 (1998) and US 2007/0099208 A1, each of which is incorporated herein by reference. Emulsion PCR on beads can also be used, for example as described in Dressman et al., Proc. Natl. Acad. Sci. USA 100:8817-8822 (2003), which is incorporated herein by reference.

Other sequencing techniques that are applicable for use of the methods and systems set forth herein are pyrosequencing, nanopore sequencing, and sequencing by ligation. Exemplary pyrosequencing techniques and samples that are particularly useful are described in U.S. Pat. No. 6,210,891; U.S. Pat. No. 6,258,568; U.S. Pat. No. 6,274,320 and Ronaghi, Genome Research 11:3-11 (2001), each of which is incorporated herein by reference. Exemplary nanopore techniques and samples that are also useful are described in Deamer et al., Acc. Chem. Res. 35:817-825 (2002); Li et al., Nat. Mater. 2:611-615 (2003); Soni et al., Clin Chem. 53:1996-2001 (2007) Healy et al., Nanomed. 2:459-481 (2007) and Cockroft et al., J. am. Chem. Soc. 130:818-820; and U.S. Pat. No. 7,001,792, each of which is incorporated herein by reference. In particular, these methods utilize repeated steps of reagent delivery. An instrument or method set forth herein can be configured with reservoirs, valves, fluidic lines and other fluidic components along with control systems for those components in order to introduce reagents and detect signals according to a desired protocol such as those set forth in the references cited above. Any of a variety of samples can be used in these systems such as substrates having beads generated by emulsion PCR, substrates having zero-mode waveguides, substrates having integrated CMOS detectors, substrates having biological nanopores in lipid bilayers, solid-state substrates having synthetic nanopores, and others known in the art. Such samples are described in the context of various sequencing techniques in the references cited above and further in US 2005/0042648; US 2005/0079510; US 2005/0130173; and WO 05/010145, each of which is incorporated herein by reference.

Exemplary labels that can be detected in accordance with various embodiments, for example, when present on or within a support structure include, but are not limited to, a chromophore; luminophore; fluorophore; optically encoded nanoparticles; particles encoded with a diffraction-grating; electrochemiluminescent label such as $Ru(bpy)^{32+}$; or moiety that can be detected based on an optical characteristic. Fluorophores that may be useful include, for example, fluorescent lanthanide complexes, including those of Europium and Terbium, fluorescein, rhodamine, tetramethylrhodamine, eosin, erythrosin, coumarin, methyl-coumarins, pyrene, Malacite green, Cy3, Cy5, stilbene, Lucifer Yellow, Cascade Blue™, Texas Red, alexa dyes, phycoerythin, bodipy, and others known in the art such as those described in Haugland, Molecular Probes Handbook, (Eugene, Oreg.) 6th Edition; The Synthegen catalog (Houston, Tex.), Lakowicz, Principles of Fluorescence Spectroscopy, 2nd Ed., Plenum Press New York (1999), or WO 98/59066, each of which is hereby incorporated by reference. In some embodiments, the one pair of labels may be excitable by a first excitation wavelength and another pair of labels may be excitable by a second excitation wavelength.

Although embodiments are exemplified with regard to detection of samples that include biological or chemical substances supported by an optical substrate, it will be understood that other samples can be imaged by the embodiments described herein. Other exemplary samples include, but are not limited to, biological specimens such as cells or tissues, electronic chips such as those used in computer processors, and the like. Examples of some of the applications include microscopy, satellite scanners, high-resolution reprographics, fluorescent image acquisition, analyzing and sequencing of nucleic acids, DNA sequencing, sequencing-by-synthesis, imaging of microarrays, imaging of holographically encoded microparticles and the like.

FIG. 1 is a block diagram of an assay system 100 for biological or chemical analysis formed in accordance with one embodiment. In some embodiments, the assay system 100 is a workstation that may be similar to a bench-top device or desktop computer. For example, a majority of the systems and components for conducting the desired reactions can be within a common housing 116 of the assay system 100. In some embodiments, the assay system 100 includes one or more components, assemblies, or systems that are remotely located from the assay system 100. Furthermore, the assay system 100 may include various components, assemblies, and systems (or sub-systems) that interact with each other to perform one or more predetermined methods or assay protocols for biological or chemical analysis.

For example, the assay system 100 includes a system controller 102 that may communicate with the various components, assemblies, and sub-systems of the assay system 100. As shown, the assay system 100 has an optical assembly 104, an excitation source assembly 106, a detector assembly 108, and a docking station or system 110 that supports one or more samples 112. In some embodiments, the optical assembly 104 is configured to direct incident light from the excitation source assembly 106 onto the sample(s) 112. The excitation source assembly 106 may include one or more excitation light sources that are configured to excite labels associated with the samples 112. The excitation source assembly 106 may also be configured to provide incident light that is reflected and/or refracted by the samples 112. As shown, the samples 112 may provide optical signals that include light emissions 116 and/or transmission light 118. The docking system 110 and the optical assembly 104 may be moved relative to each other. In particular embodiments, the docking system 110 includes a sample stage 130 and a motor assembly 132 that moves the sample stage 130 with respect to the optical assembly 104. In other embodiments, the optical assembly 104 may be moved in addition to or alternatively to the docking system 110.

The optical assembly 104 may also be configured to direct the light emissions 116 and/or transmission light 118 to the detector assembly 108. The detector assembly 108 may include one or more sample detectors. The sample detectors may be, by way of example only, CCD cameras or photodiodes. The optical assembly 104 may include an optics adjustment system (or sub-system) 120. The optics adjustment system 120 is configured to selectively move one or more optical components of the optical assembly 104. For example, the optics adjustment system 120 may selectively move a path compensator 122 and/or an optical device 124 that is located upstream or downstream from the sample 112. Components can also be shared among two or more optical trains. For example, one or more components can be alternatively placed into contact with different optical paths (e.g. emissions from different samples).

Also shown, the assay system 100 may include a fluidic control system 134 to control the flow of fluid throughout a fluidic network 135 (indicated by the solid lines) of the assay system 100. The fluidic control system 134 may deliver reagents to the sample 112 during, for example, a sequencing protocol. The assay system 100 may also include a fluid storage system 136 that is configured to hold fluids that may be used by the assay system 100 and a temperature control system 138 that regulates the temperature of the fluid. The temperature control system 138 may also generally regulate a temperature of the assay system 100 using, for example, heat sinks and blowers. Exemplary temperature control systems are described in U.S. Ser. No. 12/565,606, which is incorporated herein by reference.

In some embodiments, the fluidic network 135 includes one or more umbilical cables (not shown) that operatively couples the fluidic control system 134 and the fluidic storage system 136 to the sample 112B and other components of the assay system 100. The sample 112B may comprise a flow cell that is configured to have solutions flow therethrough during an assay protocol. The solutions may be delivered through the umbilical cable. For example, the umbilical cable may be fluidicly coupled to the flow cell and a multi-port pump, which is, in turn, fluidically coupled to various fluids (e.g., reagents, buffers, and others) in the fluid storage system 134. The pump may receive instructions for delivering different solutions to the flow cell. The umbilical cable may include one or more fluidic lines and also one or more communication lines (e.g., electrical or optical) that deliver instructions.

Also shown, the assay system 100 may include a user interface 140 that interacts with the user. For example, the user interface 140 may include a display 142 to display or request information from a user and a user input device 144 to receive user inputs. In some embodiments, the display 142 and the user input device 144 are the same device (e.g., touchscreen). As will be discussed in greater detail below, the assay system 100 may communicate with various components to perform the desired reactions. The assay system 100 may also be configured to analyze the detection data to provide a user with desired information.

The fluidic control system 134 is configured to direct and regulate the flow of one or more fluids through the fluidic network 135. The fluidic network 135 may be in fluid communication with at least one of the samples 112 and the fluid storage system 136. For example, select fluids may be drawn from the fluid storage system 136 and directed to the sample 112 in a controlled manner, or the fluids may be drawn from the sample 112 and directed toward, for example, a waste reservoir in the fluid storage system 136. Although not shown, the fluidic control system 134 may include flow sensors that detect a flow rate or pressure of the fluids within the fluid network. The sensors may communicate with the system controller 102.

The temperature control system 138 is configured to regulate the temperature of fluids at different regions of the fluidic network 135, the fluid storage system 136, and/or the sample 112. For example, the temperature control system 138 may include a thermocycler (not shown) that interfaces with the sample 112 and controls the temperature of the fluid that flows along the sample 112. The temperature control system 138 may also regulate the temperature of solid elements or components of the assay system 100 or sample 112. Although not shown, the temperature control system 138 may include sensors to detect the temperature of the fluid or other components. The sensors may communicate with the system controller 102.

The fluid storage system 136 is in fluid communication with the sample 112 and may store various reaction components or reactants that are used to conduct the desired reactions therein. The fluid storage system 136 may store fluids for washing or cleaning the fluidic network 135 or the sample 112 and also for diluting the reactants. For example, the fluid storage system 136 may include various reservoirs to store reagents, enzymes, other biomolecules, buffer solutions, aqueous, and non-polar solutions, and the like. Furthermore, the fluid storage system 136 may also include waste reservoirs for receiving waste products.

The docking system 110 is configured to engage one or more samples 112, for example, in at least one of a mechanical, electrical, and fluidic manner. The docking system 110 may hold the sample(s) 112 in a desired orientation to facilitate the flow of fluid through the sample 112 and/or imaging of the sample 112. Docking systems can be configured to deliver fluids to one sample, but not to another. The system can be configured to deliver different fluids to different samples. Alternatively or additionally, fluids can be delivered to different samples in a different temporal sequence, amount, flow rate, or duration.

The system controller 102 may include any processor-based or microprocessor-based system, including systems using microcontrollers, reduced instruction set computers (RISC), application specific integrated circuits (ASICs), field programmable gate array (FPGAs), logic circuits, and any other circuit or processor capable of executing functions described herein. The above examples are exemplary only, and are thus not necessarily intended to limit in any way the definition and/or meaning of the term system controller. In the exemplary embodiment, the system controller 102 executes a set of instructions that are stored in one or more storage elements, memories, or modules in order to at least one of obtain and analyze detection data. Storage elements may be in the form of information sources or physical memory elements within the assay system 100.

The set of instructions may include various commands that instruct the assay system 100 to perform specific operations such as the methods and processes of the various embodiments described herein. The set of instructions may be in the form of a software program. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

The software may be in various forms such as system software or application software. Further, the software may be in the form of a collection of separate programs, or a program module within a larger program or a portion of a program module. The software also may include modular programming in the form of object-oriented programming. After obtaining the detection data, the detection data may be automatically processed by the assay system 100, processed in response to user inputs, or processed in response to a request made by another processing machine (e.g., a remote request through a communication link).

The system controller 102 may be connected to the other components or sub-systems of the assay system 100 via communication links (indicated by dashed lines). The system controller 102 may also be communicatively connected to off-site systems or servers. The communication links may be hardwired or wireless. The system controller 102 may receive user inputs or commands, from the user interface 140. The user input device 144 may include a keyboard, mouse, a touch-screen panel, and/or a voice recognition system, and the like. Alternatively or in addition, the user input device 144 may also be the display 142.

In some embodiments, the assay system 100 may have interchangeable or swappable devices (e.g., plug-and-play). For example, the docking system 110 or sample stage 130 may be readily replaced or substituted with a different docking system 110 or sample stage 130. This may occur when a different type of sample 112 is desired to be used. In some embodiments, the sample 112 is readily exchanged from the sample stage 130. Furthermore, the fluid storage system 136 may be a container that is readily separated from the fluid network and replaced by another container. This may occur when the fluid in the container is depleted, has expired, or a different container is required because a user of the assay system 100 desires to run a different assay protocol. Furthermore, the system controller 102 may have swappable devices (e.g., if the user desires to use the assay system 100 to execute a different assay protocol).

FIG. 1 also illustrates a block diagram of the system controller 102. In one embodiment, the system controller 102 includes one or more processors or modules that can communicate with one another. The system controller 102 is illustrated conceptually as a collection of modules, but may be implemented utilizing any combination of dedicated hardware boards, DSPs, processors, etc. Alternatively, the system controller 102 may be implemented utilizing an off-the-shelf PC with a single processor or multiple processors, with the functional operations distributed between the processors. As a further option, the modules described below may be implemented utilizing a hybrid configuration in which certain modular functions are performed utilizing dedicated hardware, while the remaining modular functions are performed utilizing an off-the-shelf PC and the like. The modules also may be implemented as software modules within a processing unit.

The system controller 102 may include a plurality of modules 151-158 that communicate with a system control module 150. The system control module 150 may communicate with the user interface 140. Although the modules 151-158 are shown as communicating directly with the system control module 150, the modules 151-158 may also communicate directly with each other, the user interface 140, or the other systems. Also, the modules 151-158 may communicate with the system control module 150 through the other modules.

The plurality of modules 151-158 include system modules 151-153 that communicate with the sub-systems. The fluidic control module 151 may communicate with the fluidic control system 134 to control the valves and flow sensors of the fluidic network 135 for controlling the flow of one or more fluids through the fluidic network 135. The fluid storage module 152 may notify the user when fluids are low or when the waste reservoir must be replaced. The fluid storage module 152 may also communicate with the temperature control module 153 so that the fluids may be stored at a desired temperature.

The plurality of modules 151-158 may also include an optics adjustment (or correction) module 154 that communicates with the optics adjustment system 120 and an identification module 155 that determines identification information relating to the sample 112. For example, the sample 112 may be scanned before an imaging session or before being placed onto the sample stage 130 to identify the sample 112. The optics adjustment module 154 may communicate with the various devices that are capable of selectively moving the optical components, such as a transfer device or a rotatable optical device. The plurality of modules 151-158 may also include a detection data analysis module 158 that receives and analyzes the detection data (e.g., image data) from the detector assembly 108. The processed detection data may be stored for subsequent analysis or may be transmitted to the user interface 140 to display desired information to the user. Furthermore, there may be a sample module that communicates with the sample (e.g., receives signals regarding temperature of the sample or flow rate of a fluid in the sample).

Protocol modules 156 and 157 communicate with the system control module 150 to control the operation of the sub-systems when conducting predetermined assay protocols. The protocol modules 156 and 157 may include sets of instructions for instructing the assay system 100 to perform specific operations pursuant to predetermined protocols. The protocol modules 156 and 157 include a sequencing-by-synthesis (SBS) module 156 that may be configured to issue various commands for performing sequencing-by-synthesis processes. In some embodiments, the SBS module 156 may also process detection data. The protocol module 157 may be configured to scan microarrays or perform other assay protocols.

By way of one example, the SBS module 156 may be configured to issue commands for sequencing-by-synthesis processes. For example, the SBS module 156 may issue commands to perform bridge PCR where clusters of clonal amplicons are formed on localized areas within a channel (or lane) of a flow cell. After generating the amplicons through bridge PCR, the SBS module 156 may provide instructions to linearize or denature the amplicons to make sstDNA and to add a sequencing primer such that the sequencing primer may be hybridized to a universal sequence that flanks a region of interest. Each sequencing cycle extends the sstDNA by a single base and is accomplished by modified DNA polymerase and a mixture of four types of nucleotides delivery of which can be instructed by the SBS module 156. The different types of nucleotides have unique fluorescent labels, and each nucleotide has a reversible terminator that allows only a single-base incorporation to occur in each cycle. After a single base is added to the sstDNA, the SBS module 156 may instruct a wash step to remove nonincorporated nucleotides by flowing a wash solution through the flow cell. The SBS module 156 may further instruct the excitation source assembly and detector assembly to perform an image session(s) to detect the fluorescence in each of the four channels (i.e., one for each fluorescent label). After imaging, the SBS module 156 may instruct delivery of a deblocking reagent to chemically cleave the fluorescent label and the terminator from the sstDNA. The SBS module 156 may instruct a wash step to remove the deblocking reagent and products of the deblocking reaction. Another similar sequencing cycle may follow. In such a sequencing protocol, the SBS module 156 may instruct the fluidic control system 134 to direct a flow of reagent and enzyme solutions through the sample 112.

In some embodiments, the SBS module 156 may also be configured to issue various commands for performing the steps of a pyrosequencing protocol. In this case, the sample 112 may include millions of wells where each well has a single capture bead having clonally amplified sstDNA thereon. Each well may also include other smaller beads that, for example, may carry immobilized enzymes (e.g., ATP sulfurylase and luciferase) or facilitate holding the capture bead in the well. The SBS module 156 may be configured to issue commands to the fluidic control module 151 to run consecutive cycles of fluids that carry a single type of nucleotide (e.g., 1st cycle: A; 2nd cycle: G; 3rd cycle: C; 4th cycle: T; 5th cycle: A; 6th cycle: G; 7th cycle: C; 8th cycle: T; and on). When a nucleotide is incorporated into the DNA, pyrophosphate is released thereby instigating a chain reaction where a burst of light is generated. The burst of light may be detected by a sample detector of the detector assembly. Detection data may be communicated to the system control module 150, the detection data analysis module 158, and/or the SBS module 156 for processing. The detection data may be stored for later analysis or may be analyzed by the system controller 102 and an image may be sent to the user interface 140.

The protocol module 157 may be configured to send instructions for scanning a microarray for an unknown analyte. Before or after performing an imaging session, the protocol module 157 may instruct the optics adjustment system 120 to move an optical component within, into, or out of the optical path. For example, the protocol module 157 may request that the path compensator 122 be inserted into or removed from the optical path. The protocol module 157 may also request that another optical component be repositioned. Any of a variety of movable or adjustable optical components set forth herein can be moved, adjusted or otherwise manipulated in response to instructions sent from protocol module 157 or any other appropriate module of a system controller. Once the collective arrangement of the optical components is established as desired, the protocol module 157 may instruct the excitation source assembly to provide incident light onto the samples and the detector assembly to detect the optical signals provided by the sample 112.

In some embodiments, the user may provide user inputs through the user interface 140 to select an assay protocol to be run by the assay system 100. In other embodiments, the assay system 100 may automatically detect the type of sample 112 that has been inserted into the docking system 110 and confirm with the user the assay protocol to be run. Alternatively, the assay system 100 may offer a limited number of assay protocols that could be run with the determined type of sample 112. The user may select the desired assay protocol, and the assay system 100 may then perform the selected assay protocol based on preprogrammed instructions.

However, the assay system 100 may also allow the user to reconfigure an assay protocol. After determining the assay protocol to run, the assay system 100 may offer options to the user through the user interface 140 for modifying the determined protocol. For example, if it is determined that the sample 112 is to be used for amplification, the assay system 100 may request a temperature for the annealing cycle. Furthermore, the assay system 100 may issue warnings to a user if a user has provided user inputs that are generally not acceptable for the selected assay protocol. Furthermore, in other embodiments, the assay system 100 may establish or request user inputs to establish a priority status of each sample 112 in the assay system 100. The assay system 100 may then operate according to the priority statuses of the samples 112 therein. For example, the sequencing protocols may have a higher priority than the scanning protocols. According to selected priorities the assay system can run on a schedule that pauses lower priority samples when a schedule conflict arises. For example, if sequencing sample is designated to have a higher priority than an array sample then scanning of the array sample can occur while fluidic manipulations are carried out for the sequencing sample. However in this priority scheme, scanning of the array can be halted prior to full imaging of the array such that scanning of the sequencing sample can be initiated immediately following fluidic manipulations.

Figure 2:
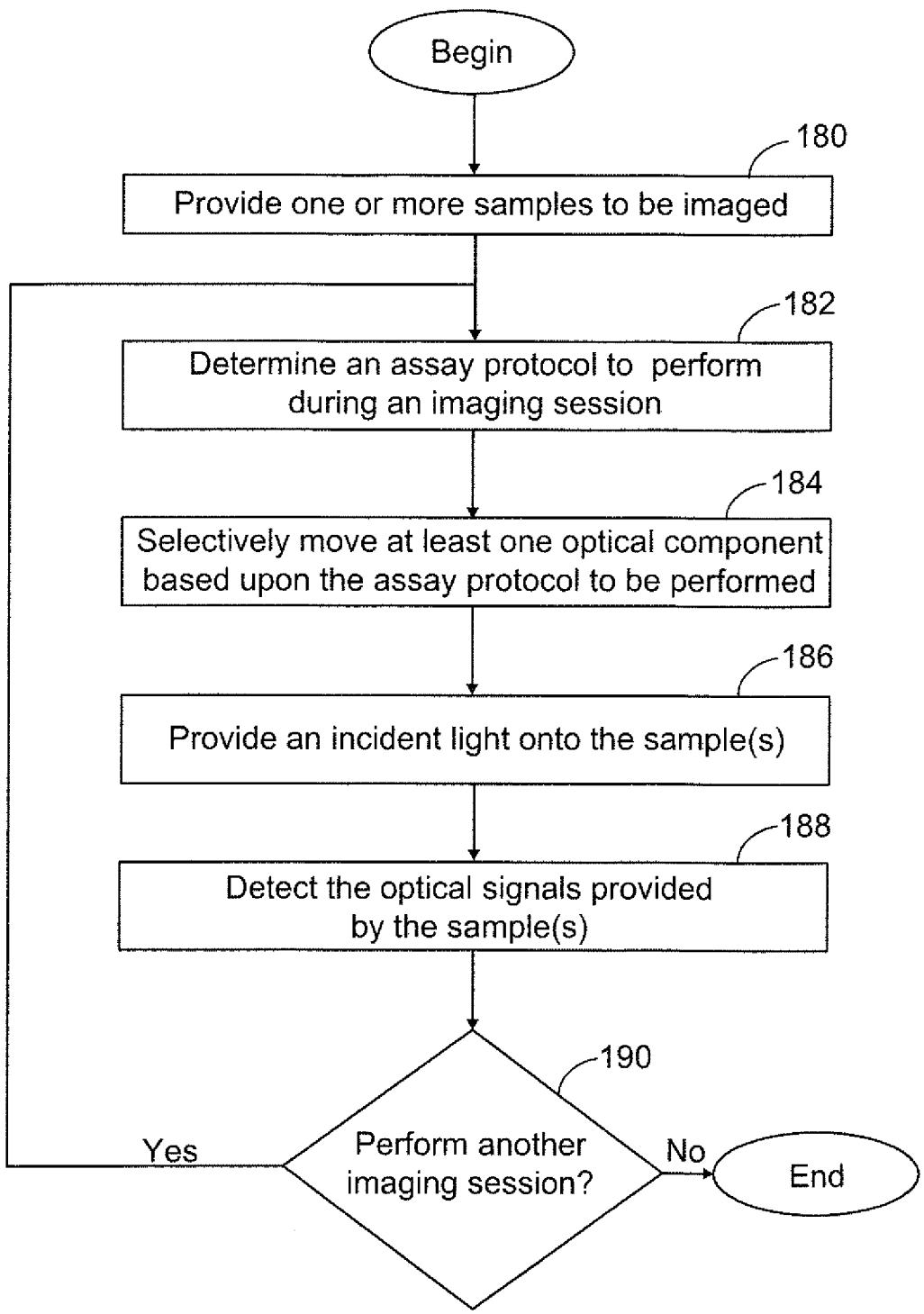
FIG. 2 is a block diagram that illustrates a method of imaging one or more samples.

FIG. 2 is a block diagram that illustrates a method of imaging one or more samples. The method may be performed by various systems, such as the assay system 100 (FIG. 1) and the workstation 200, which is described in greater detail below. The method includes providing at 180 one or more samples to be imaged. The samples may be placed onto a common sample stage of a docking system. In some embodiments, the samples may be of the same type. For example, the samples may be different microarrays for studying one or more analytes. However, the samples may also be of different types. As described above, one sample may include a flow cell where sequencing-by-synthesis may occur. The other sample may be, for example, a microarray.

The method also includes determining at 182 an assay protocol to perform during an imaging session. In some embodiments, the assay protocol includes only imaging the sample. In other embodiments, the assay protocol may also include controlling a flow of fluids through the sample to conduct desired reactions. The assay protocol may be determined by the assay system. For example, the assay system may identify the sample and determine the assay protocol appropriate for the identified sample. In addition, the assay protocol may be determined by a user of the assay system. For example, the user may enter user inputs that request the assay system to perform a particular assay protocol. After the assay protocol has been determined, the method may include at 184 selectively moving at least one optical component based upon the assay protocol to be performed. By way of example, a path compensator may be inserted into the optical and/or an optical component may be repositioned.

The method also includes providing at 186 an incident light (or input optical signals) onto the sample(s). The incident light may include one or more excitations wavelengths. The incident light may be configured to excite one or more labels in the sample or the incident light may be configured to be reflected and/or refracted by the sample. As such, the sample may provide optical signals that are received by an optical system and directed toward a detector assembly of the assay system. The method also includes detecting at 188 the optical signals provided by the sample. After the imaging session has completed, the assay system may determine at 190 if another imaging session should be performed on one or more of the samples presently within the assay system. If so, the previously described steps 182, 184, 186, and 188 may be performed again.

Figure 3:
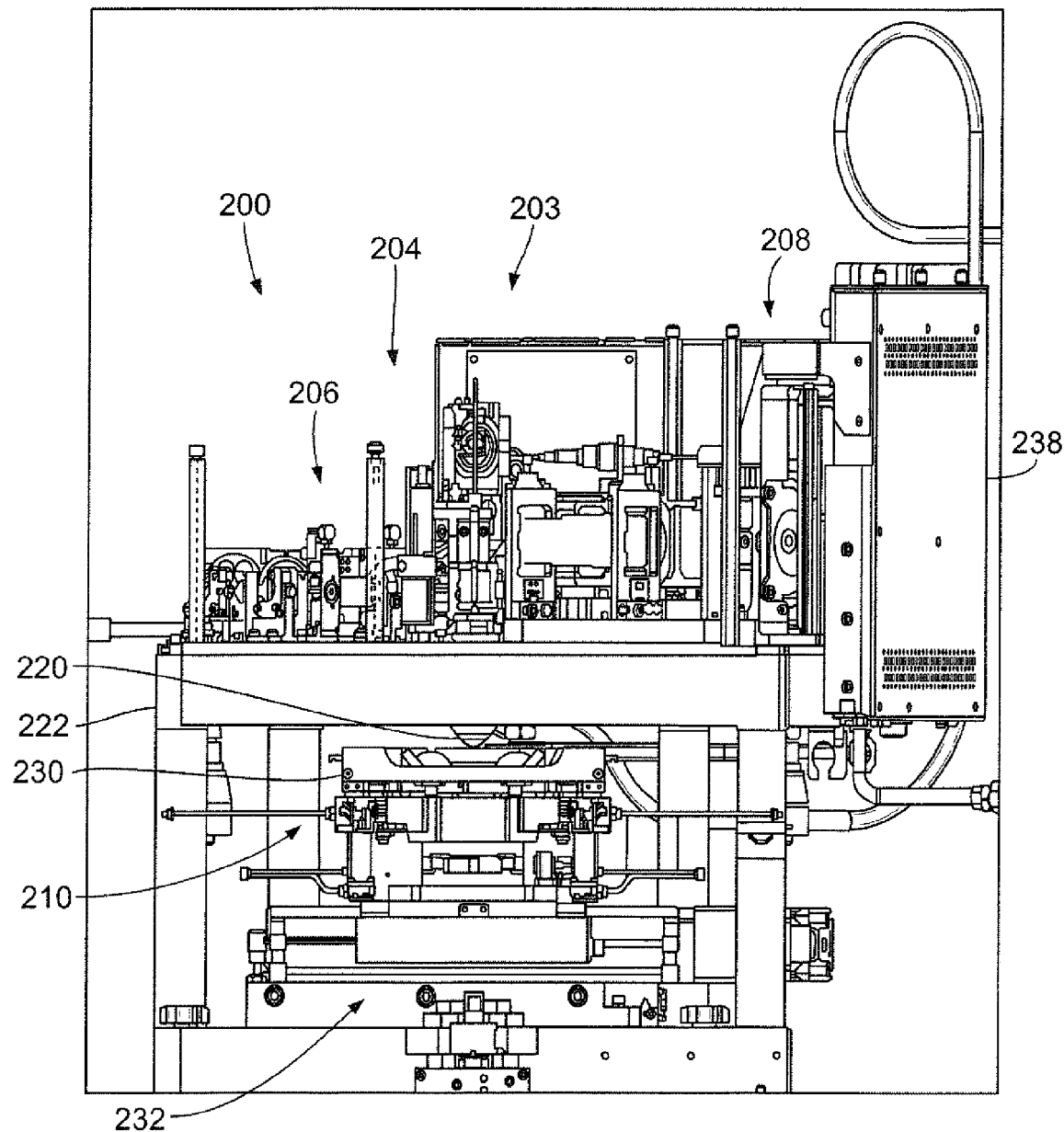
FIG. 3 is an exposed front view of a workstation for biological or chemical analysis formed in accordance with one embodiment.

FIG. 3 is a front view of a workstation 200 configured for biological or chemical analysis formed in accordance with one embodiment. The workstation 200 may have similar systems and components as the assay system 100. In particular embodiments, the workstation 200 is a stand-alone unit such that all (or nearly all) of the components described above with respect to FIG. 1 may be held within a workstation housing (not shown). The workstation 200 permits a user to perform one or more assay protocols. As shown, the workstation 200 includes an optical system 203 that includes an optical assembly 204 having an objective lens 220, a detector assembly 208, and an excitation source assembly 206. The workstation 200 also includes a docking system 210 and a fluidic control system 238. The docking system 210 includes a sample stage 230 and a motor assembly 232 that moves the sample stage 230 in x-y direction and also along a z-direction to and from the objective lens 220. The workstation 200 also includes a station frame 222 that supports all of the components with respect to each other. For example, the optical system 203 may be positioned over the docking system 210.

Figure 4:
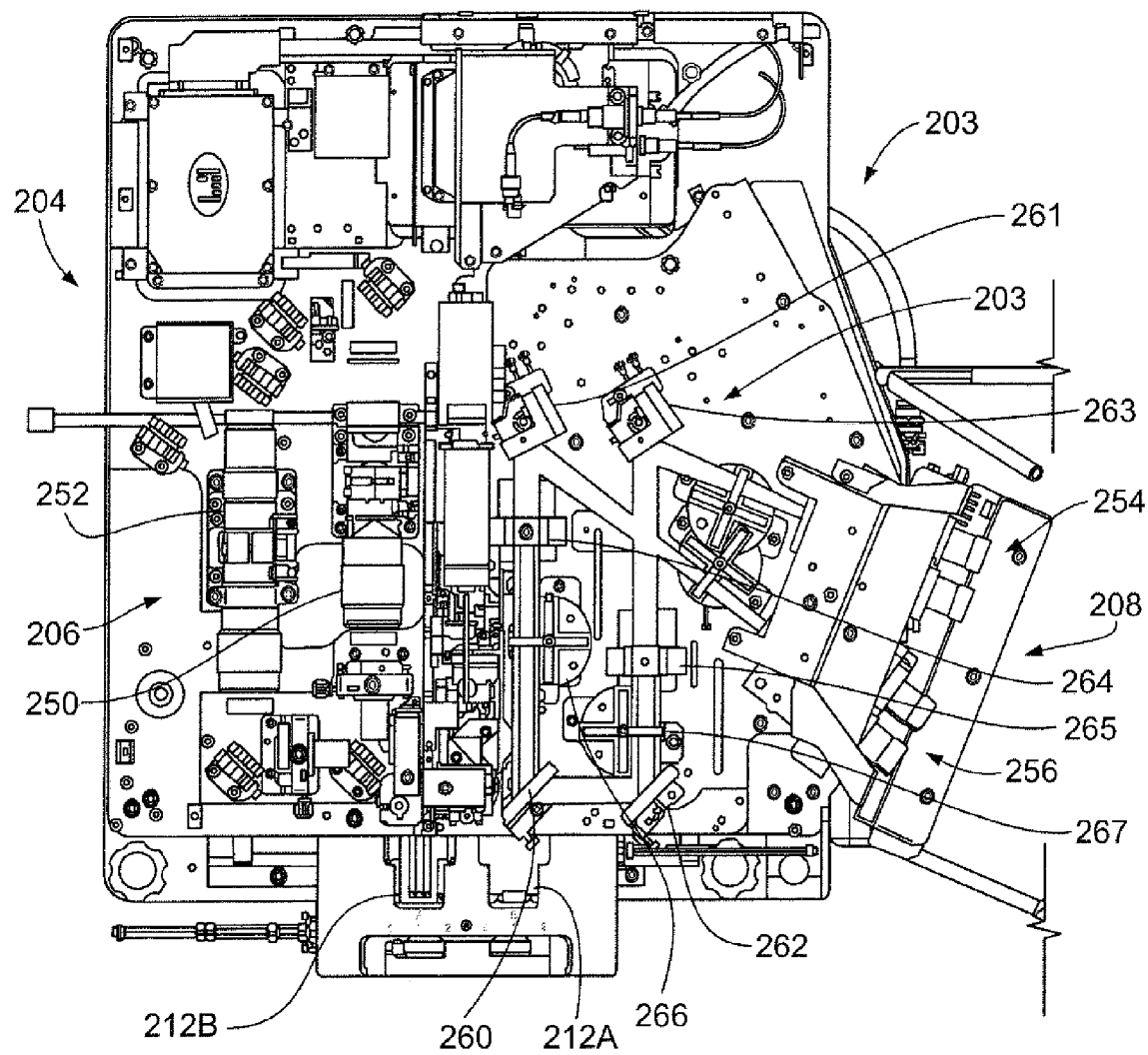
FIG. 4 is a top view of the workstation shown in FIG. 3 illustrating an optical system formed in accordance with one embodiment.

FIG. 4 is a top view of the workstation 200 (FIG. 3) and illustrates the optical system 203 in greater detail. The optical system 203 includes the excitation source assembly 206, the detector assembly 208, and the optical assembly 204. The excitation source assembly 206 includes first and second excitation light sources 250 and 252. The first and second excitation light sources may be, for example, lasers provided incident light of 660 nm and 532 nm, respectively. The optical assembly 204 includes a plurality of optical components, such as the objective lens 220 (FIG. 3), that direct the incident radiation onto samples 212. The sample 212A may be a microarray and the sample 212B may be a flow cell. The detector assembly 208 may include first and second sample detectors 254 and 256. The optical assembly 204 includes a plurality of optical components that are collectively arranged to direct the optical signals from the sample 212 to the sample detectors 254 and 256. For example, the optical assembly 204 may include a beamsplitter 260, reflectors 261-263, projection lenses 264 and 265, and optical devices 266 and 267.

Figure 5:
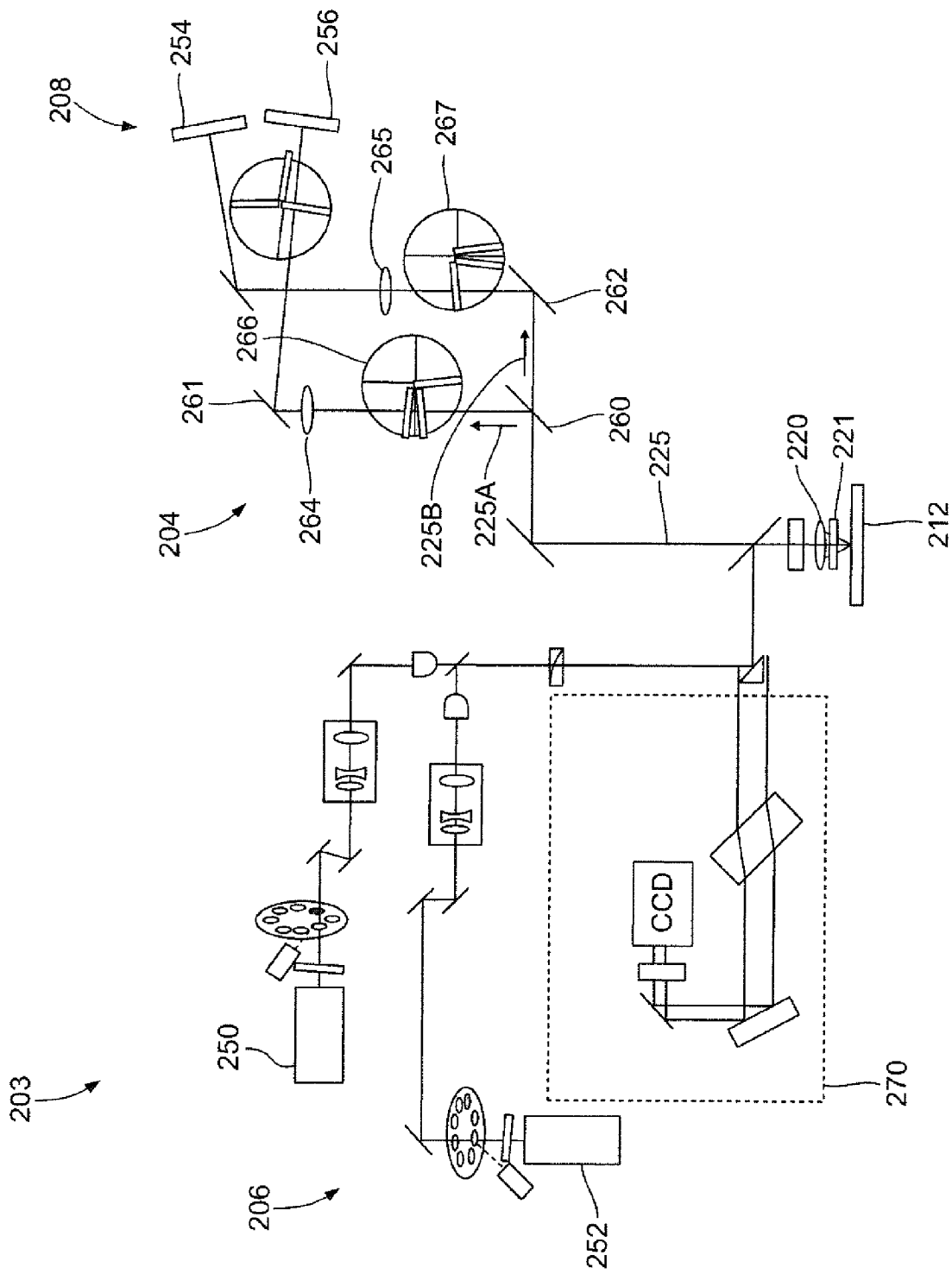
FIG. 5 is a diagram illustrating the various optical components of the optical system of FIG. 4.

FIG. 5 is a diagram illustrating the optical system 203 of the workstation 200. The first and second excitation light sources 250 and 252 may separately or simultaneously provide input optical signals that are directed by the optical components as shown (not enumerated) to the objective lens 220. As will be described in greater detail below, a path compensator 221 may be optionally located between the objective lens 220 and the sample 212. The path compensator 221 may adjust an optical path of the optical signals 225 that are provided by the sample 212. As shown, the optical signals 225 are then directed to the optical assembly 204 that is configured to direct the optical signals 225 to the detector assembly 208. The beamsplitter 260 may separate the optical signals 225 by reflecting a portion of the optical signals 225A along a first optical path toward the reflector 261 and transmitting a portion of the optical signals 225B along a second optical path toward the reflector 262.

As will be described in greater detail below, the optical devices 266 and 267 may, optionally, at least one of filter and redirect the optical signals. For example, the optical signals 225A may be filtered to one of optical signals $225A_1$ and $225A_2$, and the optical signals 225B may be filtered to one of optical signals $225B_1$ and $225B_2$. The optical signals may then be shaped or redirected by respective projection lenses 264 and 265 so that the corresponding optical signals are incident upon the respective reflectors 261 and 263. The optical signals are then directed by the reflectors 261 and 263 to be incident upon the second and first sample detectors 254 and 256. Also shown in FIG. 5, the optical system 203 may include a focus-control system 270. The focus-control system 270 may be similar to the focus-control system described in U.S. Provisional Application No. 61/300,300, filed on Feb. 1, 2010 and entitled "Focusing Methods and Optical Systems and Assemblies Using the Same," which is incorporated by reference in the entirety. Embodiments described herein may also use a dynamic autofocus method as described in U.S. application Ser. No. 12/638,770, which is incorporated by reference in the entirety.

Figure 6:
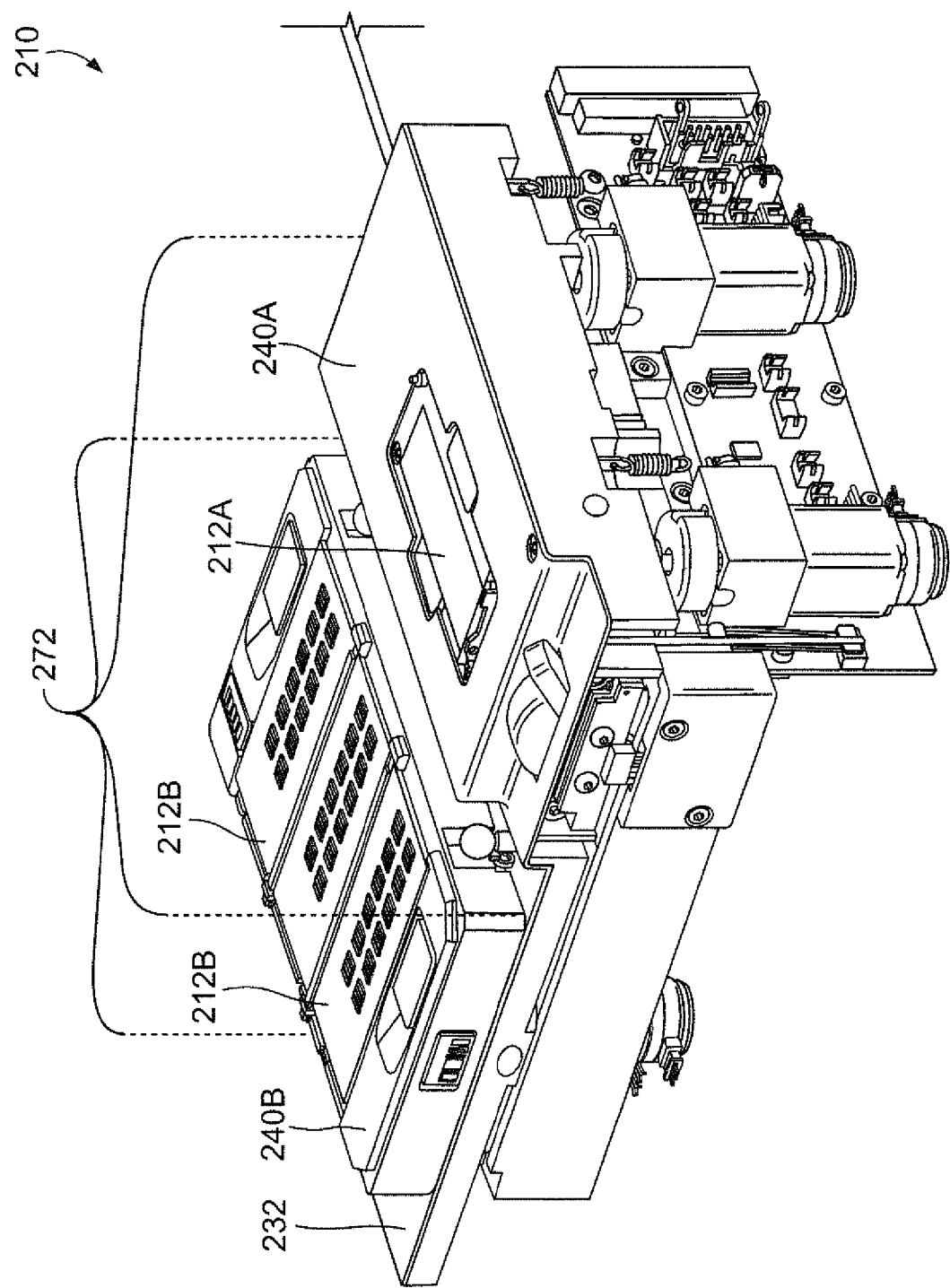
FIG. 6 is a perspective view of a docking system that may be used with the workstation shown in FIG. 3.

FIG. 6 is a perspective view of the docking system 210. As described above, the docking system 210 may be configured to support a plurality of samples 212A and 212B that may or may not be of the same type. As shown, the docking system 210 includes the sample stage 230 having a plurality of sample receptacles or interfaces 240A and 240B. The sample interface 240A is configured to support the sample 212A, and the sample interface 240B is configured to support a plurality of samples 212B. In the illustrated embodiments, the sample 212A is a flow cell and the samples 212B include microarrays. The samples 212B may include optical substrates having an array of sites or wells that include microspheres. Exemplary arrays include, without limitation, a BeadChip Array available from Illumina® Inc. (San Diego, Calif.) or others including beads in wells such as those described in U.S. Pat. Nos. 6,266,459, 6,355,431, 6,770,441, 6,859,570, and 7,622,294; and PCT Publication No. WO 00/63437, each of which is hereby incorporated by reference. Other arrays having particles on a surface include those set forth in US 2005/0227252; WO 05/033681; and WO 04/024328, each of which is hereby incorporated by reference. Other arrays set forth herein or otherwise known in the art can be used as well.

The docking system 210 includes a scan area 272 that extends along surfaces of the sample stage 230 and the sample interfaces 240A and 240B. A collecting end 294 (shown in FIG. 9) of the objective lens 220 may be relatively moved along the scan area 272 during an imaging session. For example, the sample stage 230 may be moved by the workstation 200 (FIG. 4) and/or the collecting end 294 of the objective lens 220 may be moved. Although not shown, the workstation 200 may include a guidance system that tracks the positional relationships of the objective lens 220 and the samples 212 with respect to each other. The guidance system may communicate with the focus-control system 270 (FIG. 5).

The samples 212 may be removably mounted to the sample stage 230. Furthermore, the sample interfaces 240 may be affixed to or removable from the sample stage 230. In the illustrated embodiment, the sample interface 240A is integrated with or affixed to the sample stage 230 and, as such, is not easily removed or replaced. In such cases, the sample 212A may be removably coupled to the sample interface 240. Also shown, the sample interface 240B may be removably coupled to the sample stage 230. In particular embodiments, the sample interface 240B is replaced or substituted with another sample interface having a plurality of samples thereon.

Figure 7:
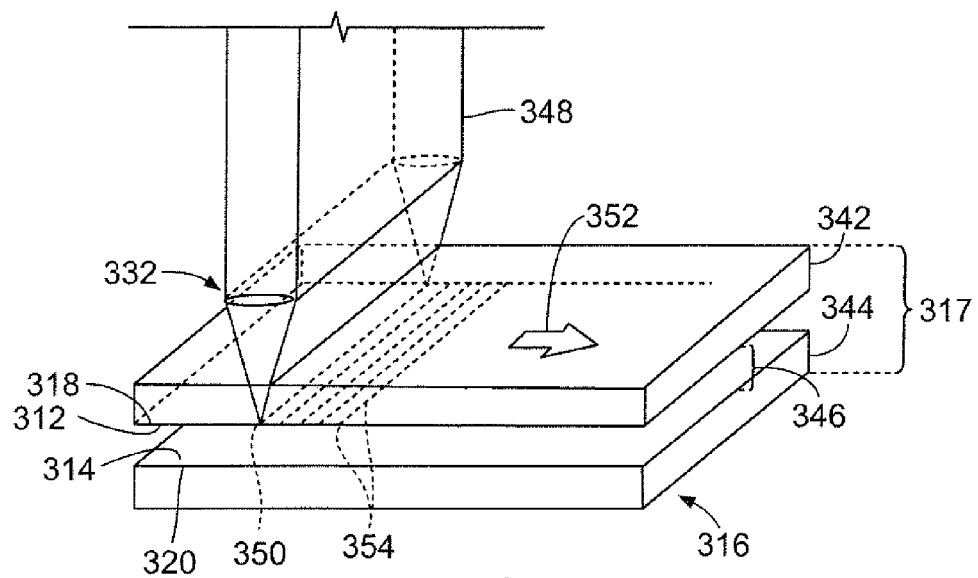
FIG. 7 is a diagram showing a perspective view of imaging a sample in accordance with one embodiment.
Figure 8:
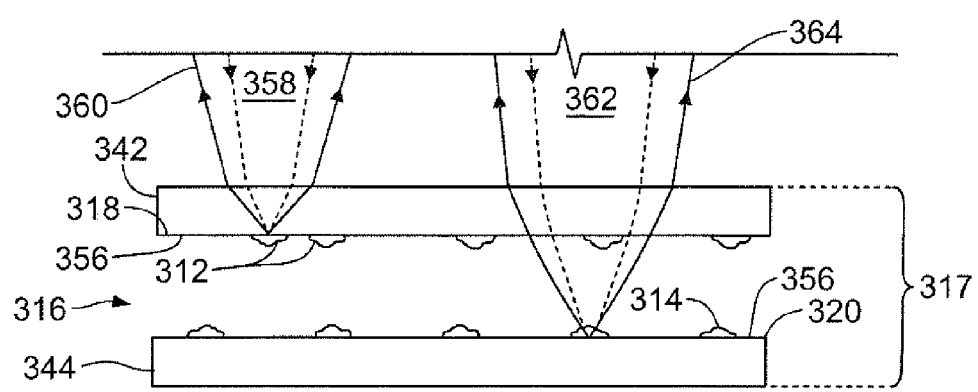
FIG. 8 is a side cross-sectional view of the diagram in FIG. 7.

FIGS. 7 and 8 are diagrams showing a perspective view and a side cross-sectional view, respectively, of imaging a sample 316 in accordance with one embodiment. In the illustrated embodiment, the sample 316 includes an optical substrate 317 that is represented as a flow cell. However, in alternative embodiments, the sample 316 may include a microarray as described above. As shown, the optical substrate 317 may include a first plate or layer 342 and a second plate or layer 344 with an interior volume or channel 346 extending between the first and second layers 342 and 344. The interior channel 346 may be configured to permit a flow of reagents therethrough. The first and second layers 342 and 344 may be formed from a variety of substrate materials. The substrate materials may be substantially transparent to wavelengths of the incident light and the optical signals that are provided from the sample. For example, the substrate materials may be substantially transparent to the optical signals emitted by one or more labels in the sample or may be substantially transparent to the optical signals that are reflected and or refracted by the sample. The first and second layers 342 and 344 may have biological components 312 and 314, respectively, on their corresponding interior surfaces 318 and 320.

In various embodiments, the sample 316 may be irradiated by excitation radiation 348 along a linear focal region 350 (also called a radiation line). However, in other embodiments, the focal region may have other configurations (e.g., point, oval). The focal region 350 may be formed by the excitation radiation 348 from one or more excitation light sources through an objective lens 332. The excitation light sources may generate light beams that are processed and shaped to provide a focal region 350 on the sample 316. The focused light beams may include optical signals having different emission spectra that excite associated fluorophores of the biological components 312 and 314. When excited, the fluorophores emit optical signals that may have different emission spectra. In some embodiments, the optical system may first direct the excitation radiation 348 toward the interior surface 318 of the optical substrate 317 to irradiate the biological components 312. In addition, the optical substrate 317 and the objective lens 332 may be moved in a relative manner with respect to each other such that the sample 316 is translated in a direction as indicated by the arrow 352. As such, the focal region 350 may progressively irradiate the biological components along the interior surface 318. As the focal region 350 translates along the interior surface 318, the focused light beams may successively scan regions 354 thereby scanning the entire interior surface 318 of the optical substrate 317. After scanning the interior surface 318, the objective lens 332 and the sample 316 may be moved with respect to each other and the same process may be repeated to scan the interior surface 320 of the optical substrate 317.

In particular embodiments, an apparatus or method can detect features on a surface at a rate of at least about 0.01 mm/sec. Depending upon the particular application, faster rates can also be used including, for example, in terms of the area scanned or otherwise detected, a rate of at least about 0.02 mm$^2$/sec, 0.05 mm$^2$/sec, 0.1 mm$^2$/sec, 1 mm$^2$/sec, 1.5 mm$^2$/sec, 5 mm$^2$/sec, 10 mm$^2$/sec, 50 mm$^2$/sec, 100 mm$^2$/sec, or faster. If desired, for example, to reduce noise, the detection rate can have an upper limit of about 0.05 mm$^2$/sec, 0.1 mm$^2$/sec, 1 mm$^2$/sec, 1.5 mm$^2$/sec, 5 mm$^2$/sec, 10 mm$^2$/sec, 50 mm$^2$/sec, or 100 mm$^2$/sec.

In some embodiments, biological material may be immobilized on the multiple surfaces of the optical substrate 317. For instance, FIG. 8 illustrates the optical substrate 317 having biological components 312 and 314 attached to the interior surfaces 318 and 320, respectively. In the illustrated embodiment, an attachment layer 356 may be formed on both interior surfaces 318 and 320. The attachment layer 356 may facilitate immobilizing the biological components 312 and 314 thereto. As shown, a first excitation radiation 358 may be used to irradiate biological components 312 on the interior surface 318 of the optical substrate 317. Light emissions 360 from the irradiated biological components 312 may return through layer 342. Simultaneously or sequentially, a second excitation radiation 362 may be used to irradiate the biological components 314 on the interior surface 320 of the optical substrate 317. Light emissions 364 may return from the irradiated biological components 314 through the channel 346 and the layer 342.

In particular embodiments, path compensators may be used when imaging samples through objective lenses having high numerical aperture (NA) values. Exemplary high NA ranges include NA values of at least about 0.6. For example, the NA value may be at least about 0.65, 0.7, 0.75, 0.8, 0.85, 0.9, 0.95, or higher. Those skilled in the art will appreciate that NA, being dependent upon the index of refraction of the medium in which the lens is working, may be higher including, for example, up to 1.0 for air, 1.33 for pure water, or higher for other media such as oils. The compensator may also find use in objectives having lower NA values than the examples listed above. In general, the NA value of an objective lens is a measure of the breadth of angles for which the objective lens may receive light. The higher the NA value, the more light that may be collected by the objective lens for a given fixed magnification. As a result, multiple objects may be distinguished more readily when using objective lens with higher NA values because a higher feature density may be possible.

Figure 9:
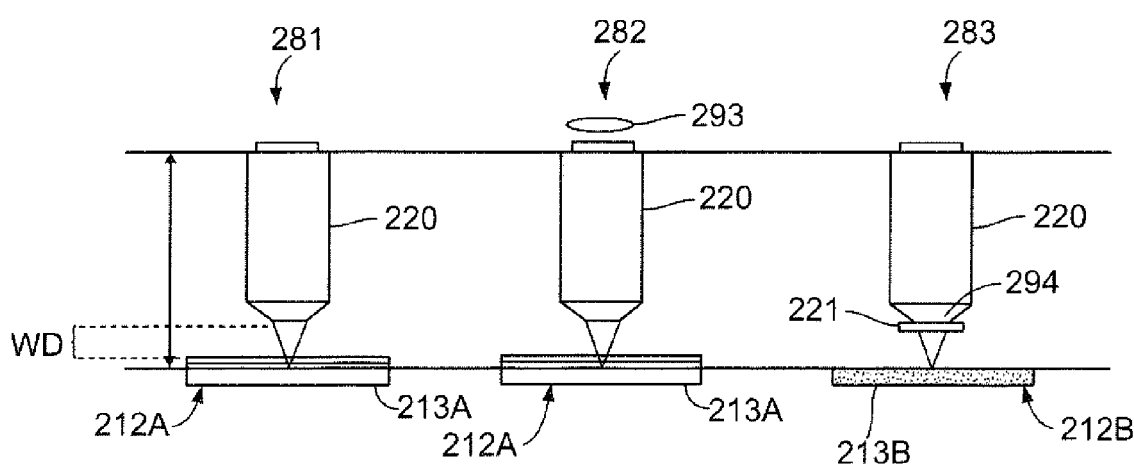
FIG. 9 illustrates various optical configurations that may be used for different imaging sessions.

FIG. 9 illustrates different optical configurations 281-283 of the optical assembly 204 that may be used during different imaging sessions. As will be described in greater detail below, embodiments described herein include adjustable or modifiable optical systems and assemblies. For example, a collective arrangement of the optical components that affect the optical signals provided by the sample may be changed for different imaging sessions. Changing a collective arrangement of the optical components causes a change in the propagation of the optical signals from the sample or a change in the spectrum of optical signals detected. The collective arrangements may be modified by removing or repositioning one or more of the optical components. Furthermore, the collective arrangements may be modified by exchanging filters along the optical path so that different optical signals are detected by the detector assembly 208.

As shown, a working distance WD may exist between the sample 212A and collecting end 294 of the objective lens 220. In some embodiments, the working distance is less than about 5000 microns. In particular embodiments, the working distance WD is less than about 2000 microns and, more particularly, less than about 1000 microns.

In FIG. 9, the samples 212A and 212B have different support structures 213A and 213B. The support structure 213A includes a flow cell having flow channels that are at least partially defined by first and second layers of material. The optical signals propagate from labels within the flow channels through one or more layers and possibly fluid to the exterior surface of the flow cell. The optical signals then propagate from the exterior surface to the objective lens. However, the support structures 213B are open-face substrates such that the labels are located proximate to corresponding exterior surfaces of the open-face substrates and provide optical signals therefrom. Thus, the optical signals that are emitted from the labels of the samples 212A and 212B will be affected differently before reaching the objective lens 220 due to the different support structures 213A and 213B. Accordingly, embodiments described herein may change the collective arrangement of the optical assembly so that the optical signals may be suitably detected.

The different optical configurations 281-283 shown in FIG. 9 represent specific examples of how path compensators 293 and 221 may be selectively moved to provide different collective arrangements. The path compensators 293 and 221 adjust the optical path of the optical signals that are provided by the sample 212. In various embodiments, optical components may be selectively moved so that a path compensator 221 may be located between the sample 212 and the objective lens 220 and/or a path compensator 293 may be located in an afocal position with respect to the objective lens 220.

As shown, the optical configuration 281 includes the objective lens 220 without any optical components (e.g., path compensators) located in the afocal position or between the objective lens 220 and the sample 212A. By way of example, the optical configuration 281 may be used during imaging sessions in which it is desired to image a bottom surface of a flow channel in the flow cell as shown in FIG. 9. When imaging a bottom surface of the flow channel, the input optical signals are transmitted through a top layer of the flow cell and then through the cavity defined between the top and bottom layers. After imaging the bottom surface of the flow channel, the assay system may move to image other surfaces of the sample (e.g., a top surface of the flow channel or an exterior surface of the flow cell or another sample). In such cases, the optical signals are no longer being transmitted through the top layer and the cavity. More specifically, if the assay system subsequently images a top surface of the flow channel or an exterior surface of a different sample, then it may be desirable to adjust the optical path or focal region to compensate for the reduced layers.

As such, the optical configuration 282 includes the path compensator 293 located at the afocal position with respect to the objective lens 220. The path compensator 293 may be selectively moved to the afocal position by a transfer device, such as transfer devices that are similar to the transfer devices described elsewhere herein or in US 2009/0272914, which is incorporated herein by reference. The optical configuration 282 may be used during imaging sessions in which it is desired to image a top surface of a flow channel in the flow cell.

The optical configuration 283 includes the path compensator 221 being located between a collecting end 294 of the objective lens 220 and the sample 212 at an imaging position. In the imaging position, the path compensator 221 and the collecting end 294 may be spaced apart from each other by a fixed distance. However, the path compensator 221 and the sample 212B may be spaced apart by an adjustable distance. More specifically, the sample 212B and the objective lens 220 may be movable to and from each other during imaging sessions.

The path compensator 221 may be selectively moved to the imaging position by a transfer device (discussed further below). The path compensator 221 may have a fixed position with respect to the objective lens 220 during imaging sessions. In some embodiments, the path compensator 221 is operatively coupled to the objective lens 220 through one or more intervening components. In alternative embodiments, the path compensator 221 is directly attached to the collecting end 294 of the objective lens 220. The optical configuration 283 may be used to scan, for example, an exterior surface of a microarray.

In an alternative embodiment, a substrate layer 227 (indicated by dashed lines in FIG. 9) may be positioned above the support structure 213B. The substrate layer 227 may be configured to allow input light signals from the excitation light source(s) and light emissions from the sample 212B to propagate therethrough. For example, the substrate layer 227 may be positioned immediately over and rest on the support structure 213B. A surface of the substrate layer 227 may interface with a surface of the support structure 213B or sample 212B. The substrate layer 227 may have a uniform thickness. In particular embodiments, the substrate layer 227 is a coverslip or slide. In embodiments that use the substrate layer 227, one or both of the path compensators 293 and 221 may be removed. In particular embodiments, the substrate layer 227 is used without the path compensators 293 and 221.

In some embodiments, the substrate layer 227 may be removeable and configured to be placed upon the support structure 213B (e.g., by a user of the system). The substrate layer 227 may be positioned by an individual or by an automated machine using, for example, a transfer device similar to those described herein. Alternatively, the sample 212B may be provided to the user with the substrate layer 227 coupled to the support structure 213B (e.g., the substrate layer 227 may be a part of the support structure 213B).

Figure 10:
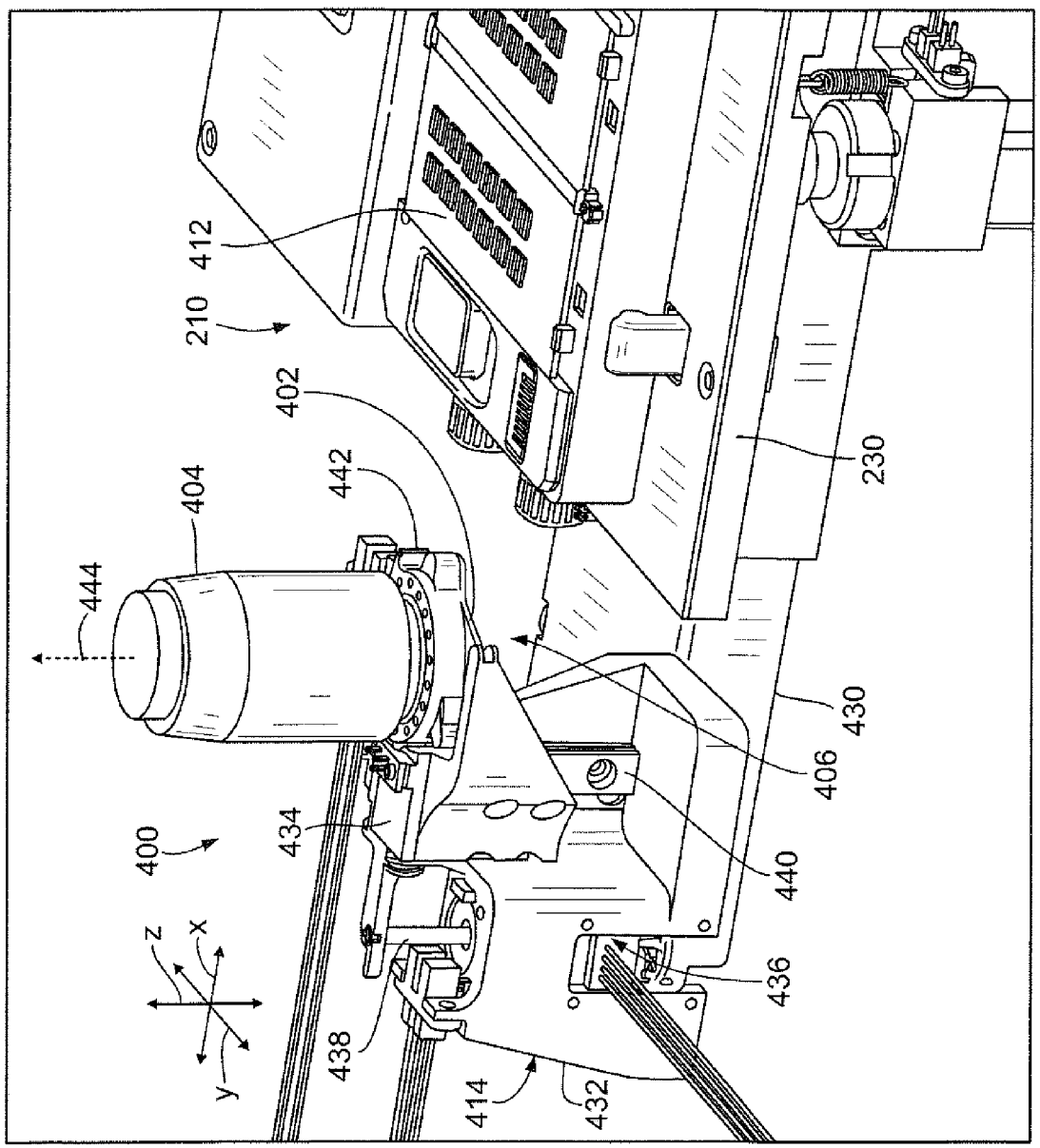
FIG. 10 is a perspective view of a transfer device for removably coupling a path compensator to an objective lens in accordance with one embodiment.

FIG. 10 is a perspective view of a transfer device 400 of the workstation 200 (FIG. 3) that is operatively coupled to or may be an assembly of the docking system 210. In the illustrated embodiment, the transfer device 400 has a fixed relationship with respect the sample stage 230 such that the transfer device 400 moves with the sample stage 230. The transfer device 400 is configured to removably locate an optical path compensator 402 with respect to an objective lens 404. The path compensator 402 adjusts an optical path of the optical signals when the path compensator 402 is located in an imaging position between the objective lens 404 and the sample 412. The path compensator 402 may adjust a focal region associated with the objective lens 404 when in the imaging position.

The sample stage 230 and the objective lens 404 may be moveable relative to each other so that the sample stage 230 and the objective lens 404 have different positional relationships. As such, the sample stage 230 may move from a first positional relationship proximate to a collecting end of the objective lens 404 to a second positional relationship (shown in FIG. 10) where an open space exists proximate to the collecting end. The open space may permit access to the objective lens so that the transfer device 400 may removably locate the path compensator 402.

In the illustrated embodiment, the transfer device 400 includes a platform assembly 414, the motor assembly 232

(FIG. 3), and a bridge member 430 that operatively couples the platform assembly 414 to the motor assembly 232. In some embodiments, the bridge member 430 may be a part of or operatively coupled to a system motor assembly (not shown) for moving the docking system and the transfer device along the Y-axis. In the illustrated embodiment, the objective lens 404 remains in a substantially fixed position while the transfer device 400 and the docking system 210 are moved by the motor assembly 232. Alternatively or in addition to, the objective lens 404 may move with respect to the transfer device 400 and the docking system 210.

The transfer device 400 is configured to selectively move the path compensator 402 to and from the imaging position. In the imaging position, the path compensator 402 is positioned such that the optical signals propagate through the path compensator during the imaging sessions. In particular embodiments, the path compensator 402 is operatively coupled to the objective lens 404 in the imaging position such that the path compensator 402 has a fixed relationship with respect to the objective lens 404. As such, the transfer device 400 may locate the path compensator 402 with respect to the objective lens 404. The transfer device 400 may locate the path compensator 402 at the imaging position for a first imaging session and remove the path compensator 402 from the imaging position for a second imaging session. The transfer device 400 may locate the path compensator 402 at the imaging position to detect optical signals from one type of sample and remove the path compensator 402 from the imaging position to detect optical signals from another type of sample.

In the illustrated embodiment, the platform assembly 414 includes a base 432 that is mounted onto the bridge member 430 and a movable holder or platform 434 that is supported by the base 432. The platform assembly 414 may also include an actuator assembly 436 that is operatively coupled to the movable platform 434 through a rod or piston 438. The base 432 includes a guide rail 440 that slidably engages the movable platform 434. When the actuator assembly 436 is activated, the actuator assembly 436 drives the movable platform 434 in a direction along a z-axis. The movable platform 434 slides along the guide rail 440. As shown, the direction along the z-axis may be parallel to a viewing axis 444 of the objective lens 404. As such, the platform assembly 414 may control a height or elevation of the movable platform 434. As will be described in greater detail below, the platform assembly 414 is configured to removably couple the path compensator 402 to the objective lens 404. However, the transfer device 400 shown in FIG. 10 illustrates only one embodiment for removably coupling a path compensator to the objective lens. Various other configurations, devices, and mechanical assemblies may be made to facilitate locating the path compensator.

Also shown in FIG. 10, the objective lens 404 has a collecting end 406 that is substantially level with the sample 412. The collecting end 406 is configured to receive the optical signals that are provided by the sample 412 during an imaging session. In the illustrated embodiment, the path compensator 402 is located with respect to the collecting end 406. For example, the objective lens 404 may have a collar 442 that directly attaches to the path compensator 402 when the path compensator 402 is removably coupled to the objective lens 404.

Figure 11:
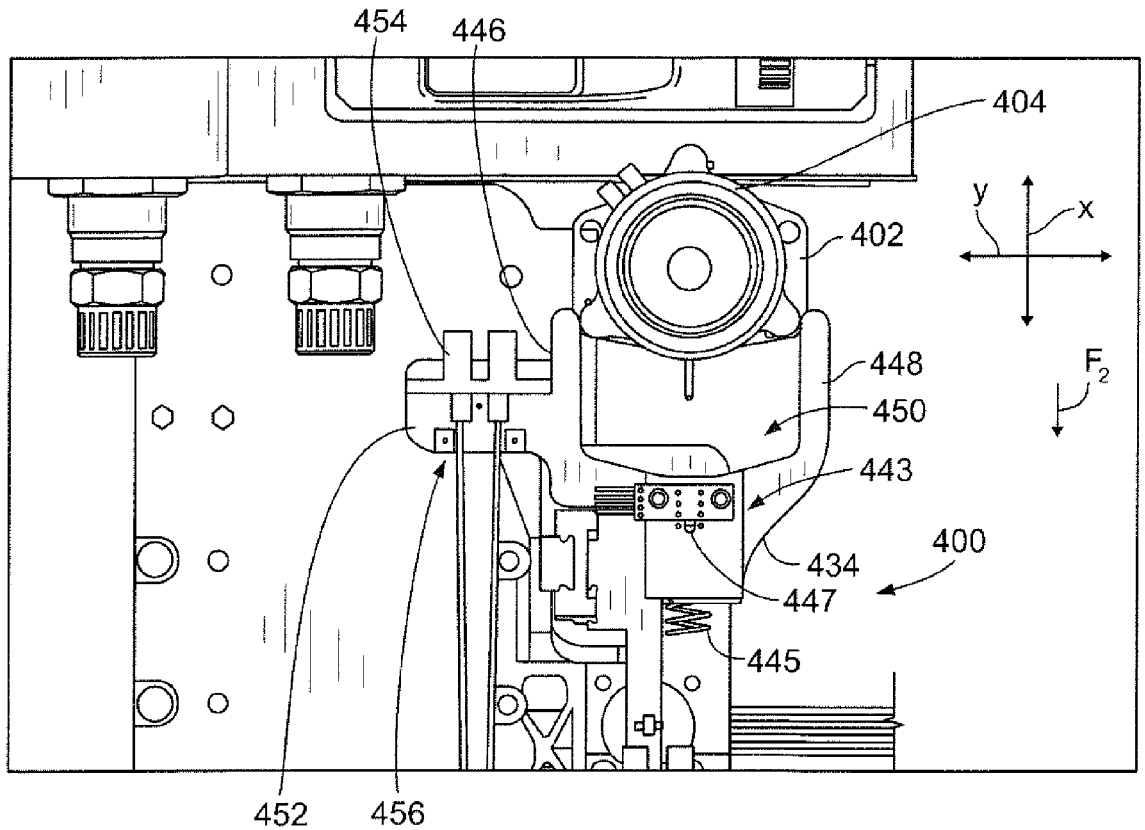
FIG. 11 is a top plan view of the transfer device of FIG. 10 when the transfer device is in a withdraw position.

FIG. 11 is a top plan view of the transfer device 400. The movable platform 434 is in a withdrawn or retracted position with respect to the path compensator 402, which is operatively coupled to the objective lens 404. The movable platform 434 may include a pair of arms 446 and 448 that are spaced apart from each other and define a component-reception region 450 therebetween. The component-reception region 450 is sized and shaped to receive and hold the path compensator 402. In some embodiments, the component-reception region 450 is sized and shaped to permit the path compensator 402 to float or move freely within a confined space defined by the component-reception region 450.

Also shown in FIG. 11, the movable platform 434 may include a wing member 452 that includes a confirmation sensor 454 attached thereto. The confirmation sensor 454 may have other positions in alternative embodiments. In the illustrated embodiment, the wing member 452 also includes a plurality of fiducial markers 456 that are located in a fixed position with respect to the movable platform 434 to facilitate determining a spatial position of the movable platform 434 with respect to other components, such as the path compensator 402. The fiducial markers 456 may be spaced apart from each other in a predetermined manner and located in a viewable position. For example, the fiducial markers 456 may be viewed by looking down the z-axis from above the movable platform 434. In alternative embodiments, the fiducial markers 456 may be positioned elsewhere on the movable platform 434 or in a fixed position with respect to the movable platform.

The fiducial markers 456 may comprise an inorganic material that fluoresces when excited by light. In one embodiment, the fiducial markers 456 include rubies. In another embodiment, the fiducial markers 456 may include a filler material comprising inorganic fluorescent powder mixed with an adhesive and cured. The filler material may be deposited into cavities or etchings along a surface of e.g., the movable platform 434. In addition, the fiducial markers 456 and a viewing device may form an alignment mechanism that facilitates controlling the movement of the transfer device 400. For example, the optical system may view the fiducial markers 456 through the objective lens 404 or a separate viewing device.

Also shown in FIG. 11, the transfer device 400 may include a retention mechanism 443 comprising a spring 445 and a magnet 447. In the illustrated embodiment, the magnet is located between the arms 446 and 448 and provides a magnetic force $F_2$ in a direction away from the objective lens 404 along the X-axis. Alternatively, the magnetic force $F_2$ may extend in a direction along the Y-axis thereby resisting movement along the X-axis toward the objective lens 404 and out of the component-reception region 450. The retention mechanism 443 operates to retain the path compensator 402 within the component-reception region 450 so that the path compensator 402 is not inadvertently removed from a desired position or dropped during operation of the workstation.

Figure 12:
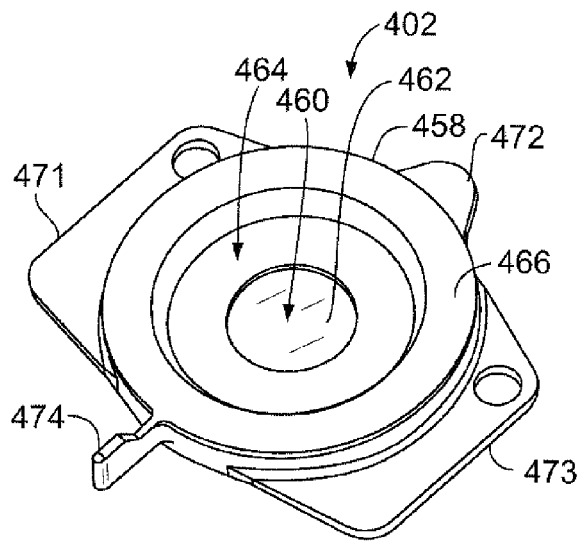
FIG. 12 is an isolated perspective view of the path compensator.

FIG. 12 is an isolated perspective view of the path compensator 402. In the illustrated embodiment, the path compensator 402 includes an element frame 458 that includes an aperture 460 where an optical element 462 is located. The optical element 462 is configured to permit optical signals to propagate therethrough and is sized and shaped to have a desired effect on the optical signals. For example, the optical element 462 may have a thickness configured to adjust the optical path of the optical signals. In particular embodiments, the optical element 462 is an optical flat having a substantially uniform thickness. Also shown, the element frame 458 includes a recess 464 that is defined by a ridge 466 configured to interface with or engage the collecting end 406 (FIG. 10) of the objective lens 404 (FIG. 10). The ridge 466 may have a substantially annular shape that surrounds the recess 464. The recess 464 and ridge 466 may be sized and shaped to locate the optical element 462 in a desired position with respect to the collecting end 406. Also shown in FIG. 12, the element frame 458 may have radial projections or wings 471-474 that project in a radial manner from the ridge 466.

Figure 13:
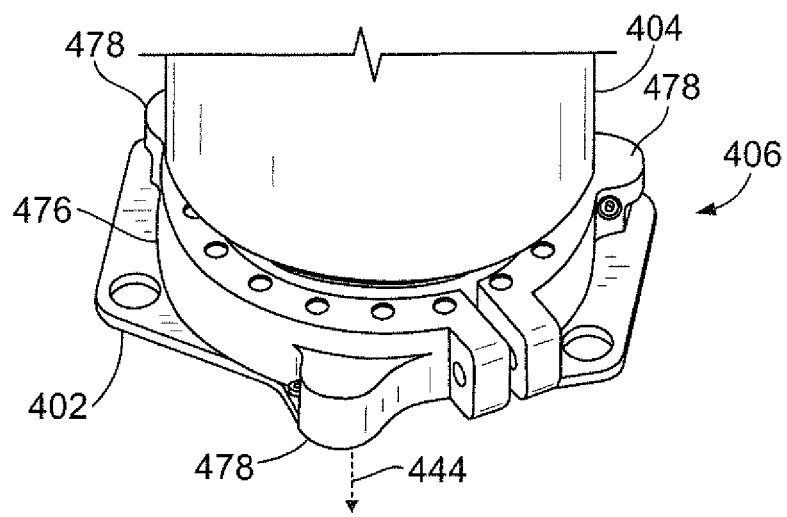
FIG. 13 is a perspective view of a collecting end of the objective lens having the path compensator removably coupled thereto.

FIG. 13 is a perspective view of the collecting end 406 of the objective lens 404 having the path compensator 402 removably coupled thereto. In the illustrated embodiment, the path compensator 402 is operatively coupled to the objective lens 404 such that the path compensator 402 has a fixed position with respect to the objective lens 404. For example, the objective lens 404 may include a collar 476 that surrounds the collecting end 406. The path compensator 402 may directly attach to the collar 476 thereby operatively coupling to the objective lens 404. However, in alternative embodiments, the path compensator 402 may directly attach to the objective lens 404 or may have additional intervening components that facilitate coupling the path compensator 402 and the objective lens 404. Also shown, the collar 476 may include fastener protrusions 478 that project in a radial manner away from the viewing axis 444 of the objective lens 404.

Figure 14:
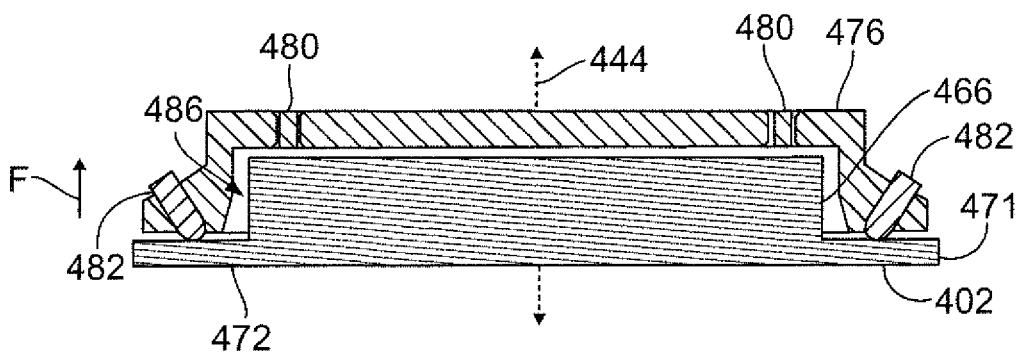
FIG. 14 is a cross-sectional view of the path compensator taken along the lines 14-14 shown in FIG. 15.
Figure 15:
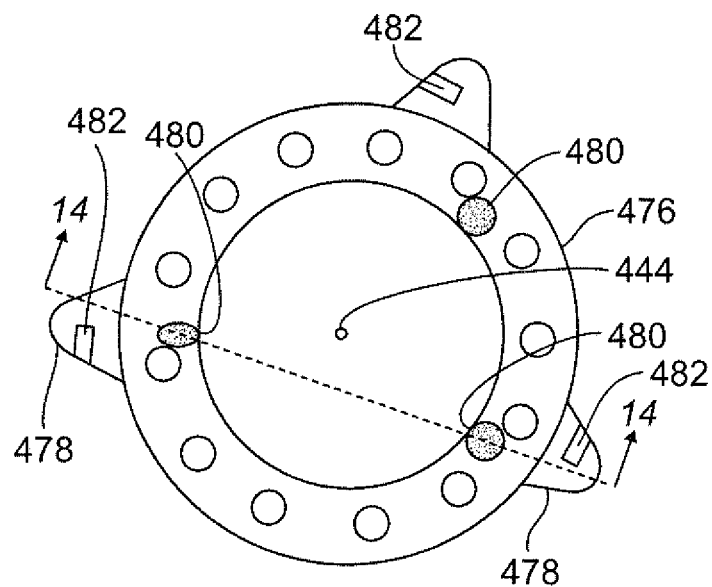
FIG. 15 is a top plan illustration of a collar that may be used to removably couple the path compensator to the objective lens.

FIGS. 14 and 15 provide greater detail of the interaction between the collar 476 and the path compensator 402. FIG. 14 is a cross-sectional view of the path compensator 402 and the collar 476 taken along the lines 14-14 shown in FIG. 15. FIG. 15 is a schematic plan view of the collar 476 when attached to the path compensator 402 (not shown in FIG. 15). In the illustrated embodiment, the collar 476 may include a component cavity 486 that is configured to receive the ridge 466 of the path compensator 402. The component cavity 486 and the ridge 466 may be sized and shaped with respect to each other to facilitate orienting the path compensator 402 in the desired imaging position.

In the illustrated embodiment, the path compensator 402 comprises a magnetic material. As shown, the collar 476 may include a plurality of magnets 480 that are distributed about the viewing axis 444. In the exemplary embodiment, the magnets 480 include permanent magnets. However, in alternative embodiments, the magnets may include electromagnets. The magnets 480 may be evenly distributed about the viewing axis 444 as shown in FIG. 15. As will be described in greater detail below, the magnets 480 provide a coupling force F that attracts the path compensator 402 toward the collecting end 406 of the objective lens 404 (FIG. 13). Furthermore, the coupling force F may be sufficient to support a weight of the path compensator 402 so that the path compensator 402 remains operatively coupled to the objective lens 404 and does not inadvertently disengage from the collar 476 or move from the imaging position during an imaging session.

Also shown in FIGS. 14 and 15, the collar 476 may include a plurality of adjustable orientation elements 482, which are illustrated as set screws. When calibrating or providing maintenance to the workstation 200 (FIG. 3), the adjustable orientation elements 482 may be moved to adjust the imaging position of the path compensator 402 or, more specifically, the optical element 462. For example, the set screws may be rotated to adjust an orientation of the path compensator 402 relative to the viewing axis 444 of the objective lens 404. As a specific example, one or more of the set screws maybe rotated so that the optical element 462 is normal to the viewing axis 444. In addition, the set screws may be rotated to increase or decrease a distance that the set screw projects from a bottom surface of the collar 476. Although the adjustable orientation elements 482 are shown as set screws, alternative orientation elements 482 may be used that cooperate with one another to adjust an orientation or location of the path compensator 402. In the illustrated embodiment, the adjustable orientation elements 482 are configured to engage the projection 471-473.

Figure 16:
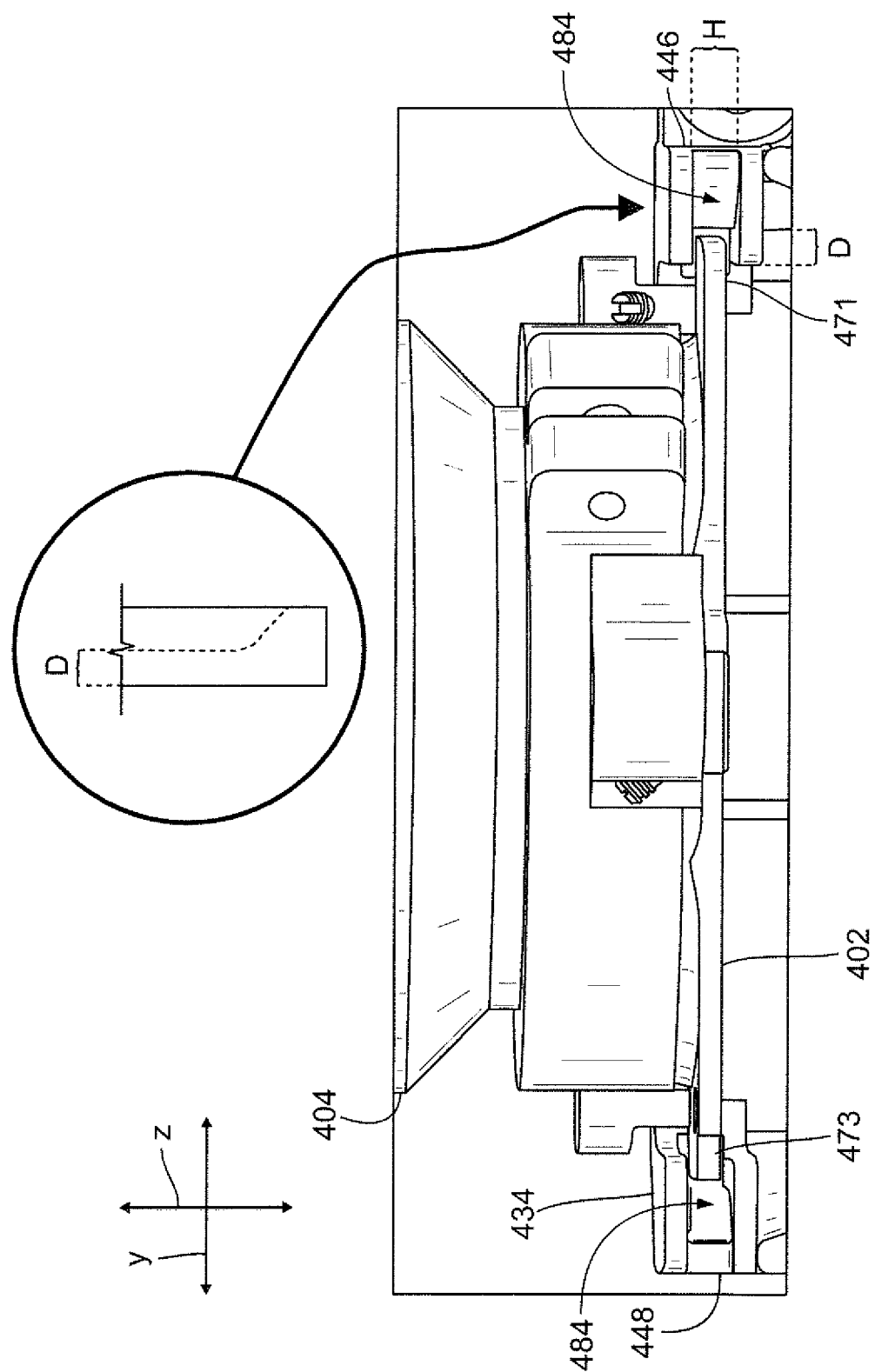
FIG. 16 is a front view showing a movable platform of the transfer device in an engaged position with respect to the path compensator.

FIG. 16 illustrates the path compensator 402 operatively engaged to the objective lens 404 and the movable platform 434 in an engaged position with respect to the path compensator 402. As shown, the arms 446 and 448 include corresponding grooves or channels 484 that are sized and shaped to receive the projections 471 and 473 of the path compensator 402, respectively. The channels 484 are sized and shaped to permit the path compensator 402 to float with respect to the arms 446 and 448 and, as such, at least partially define the component-reception region 450. More specifically, the channels 484 have a height H and a depth D. The height H is greater than a thickness of the projections 471 and 473 thereby allowing the path compensator 402 to float in a vertical manner along the z-axis. Furthermore, the depth D is sized with respect to the projections 471 and 472 extending from the ridge 466 (FIG. 12) to permit the path compensator 402 to float in a horizontal manner along the y-axis.

As such, the path compensator 402 may be floatable with respect to the movable platform 434 (or transfer device 400) and within a confined space of the component-reception region 450. By permitting the path compensator 402 to float with respect to transfer device 400, the transfer device 400 may tolerate minor misalignments between the arms 446 and 448 and the path compensator 402. Thus, if the path compensator 402 is misaligned with the collecting end 406 of the objective lens 404, the collar 476 may engage and center the path compensator 402 as the two mate with each other. Furthermore, by allowing the path compensator 402 to float within the component-reception region 450, the path compensator 402 may be capable of engaging the collecting end 406 through magnetic forces as described in greater detail below.

Figure 17:
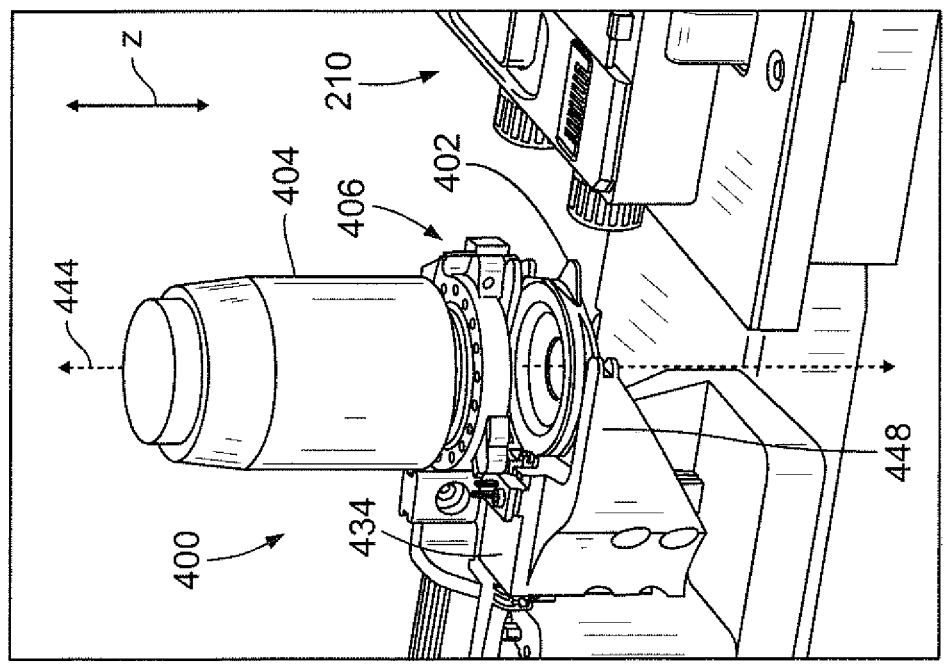
FIG. 17 is a perspective view of the transfer device before the path compensator is removably coupled to the objective lens.

FIGS. 17-20 illustrate the transfer device 400 at various stages with respect to the objective lens 404. FIG. 17 is perspective view of the transfer device 400 before the path compensator 402 is removably coupled to the objective lens 404. As shown, the transfer device 400 and the docking system 210 have fixed positions with respect to each other. Thus, when the transfer device 400 is moved to removably couple the path compensator 402 to the objective lens 404, the docking system 210 or the sample stage 230 is also moved away from the objective lens 404 thereby providing access for the path compensator 402 to the collecting end 406 of the objective lens 404. As shown in FIG. 17, the path compensator 402 is located below the collecting end 406 and aligned with the viewing axis 444. The movable platform 434 has been moved to an elevation in the Z-axis that prevents the transfer device 400 from inadvertently snagging or otherwise bumping the objective lens 404 or other components of the workstation 200. In some embodiments, when the movable platform 434 is supporting the path compensator 402, the path compensator 402 is freely held by the arms 446 (FIG. 16) and 448 of the movable platform 434. More specifically, the path compensator 402 may be substantially held in position by a gravitational force and resulting friction between the arms 446 and 448 and the projections 471 and 473 (FIG. 11) of the path compensator 402.

Figure 18:
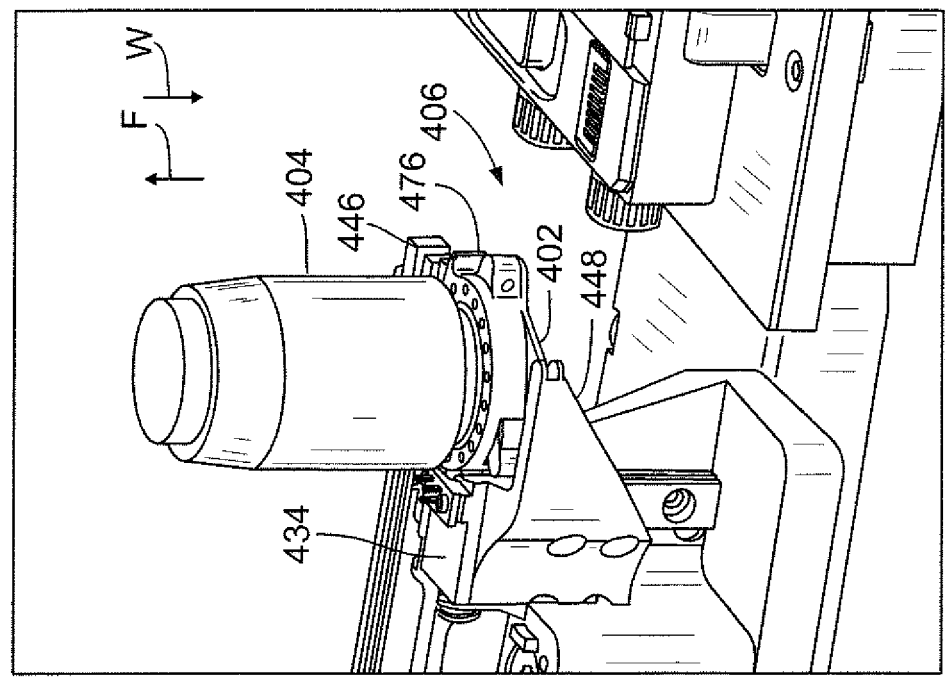
FIG. 18 is a perspective view of the transfer device when the path compensator is removably coupled to the objective lens.

FIG. 18 shows the path compensator 402 removably coupled to the objective lens 404 and directly attached to the collar 476. The actuator assembly 436 (FIG. 10) may raise the movable platform 434 along the z-axis (and the viewing axis 444) toward the objective lens 404 so that path compensator 402 is received by the component cavity 486 (FIG. 14) of the collar 476. If the path compensator 402 is misaligned with the collecting end 406 as the path compensator approaches the collar 476, the collar 476 may engage and center the path compensator 402 as the path compensator 402 and the collar 476 mate with each other. Furthermore, in the illustrated embodiment, as the path compensator 402 approaches the collar 476, the coupling force F increases. More specifically, as a distance between the magnets 480 (FIG. 14) of the collar 476 and the magnetic material of the path compensator 402 decreases, the coupling force F increases. The coupling force F may be configured to exceed a weight W of the path compensator 402 (or the gravitational force G on the path compensator 402) when the path compensator 402 is a located less than a predetermined distance away from the collar 476. When the coupling force F exceeds the weight W of the path compensator 402 (or the gravitational force G), the path compensator 402 may be lifted from the movable platform 434 and brought toward the collar 476.

In some embodiments, the coupling force F is the only force that couples the path compensator 402 and the collar 476. As such, negative effects caused by the path compensator 402 reaching the collecting end 406 are minimized or reduced since the total momentum that impacts the objective lens 404 may be substantially limited to the mass of the path compensator 402 and the velocity at which the path compensator 402 contacts the collecting end 406. In such embodiments, the objective lens 404 may not sustain a substantial force from the transfer device 400, which may damage or otherwise negatively affect the objective lens 404. However, in other embodiments, the arms 446 and 448 press the path compensator 402 against the collar 476.

Figure 19:
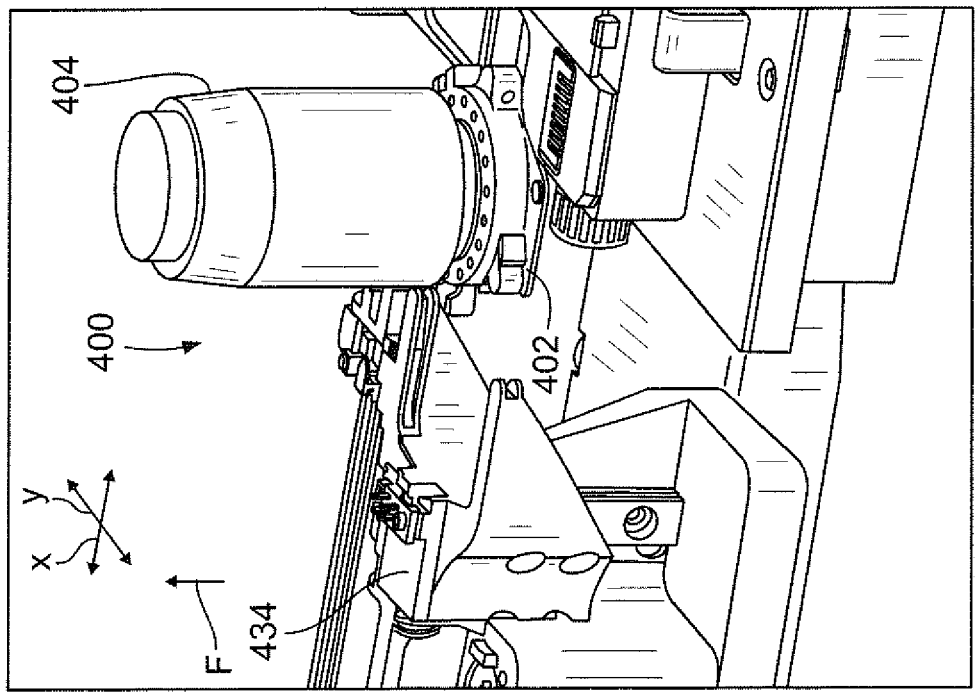
FIG. 19 is a perspective view of the transfer device in a withdrawn position with respect to the path compensator.

FIG. 19 illustrates the transfer device 400 in a withdrawn stage with respect to the objective lens 404 and the path compensator 402. When the movable platform 434 is withdrawn, the transfer device 400 is moved in an axial direction along the x-axis away from the objective lens 404. More specifically, the transfer device 400 may be moved in a direction that is substantially perpendicular to the viewing axis 444 after the path compensator 402 is operatively coupled to the objective lens 404. The path compensator 402 remains coupled to the collar 476 through the coupling force F.

Figure 20:
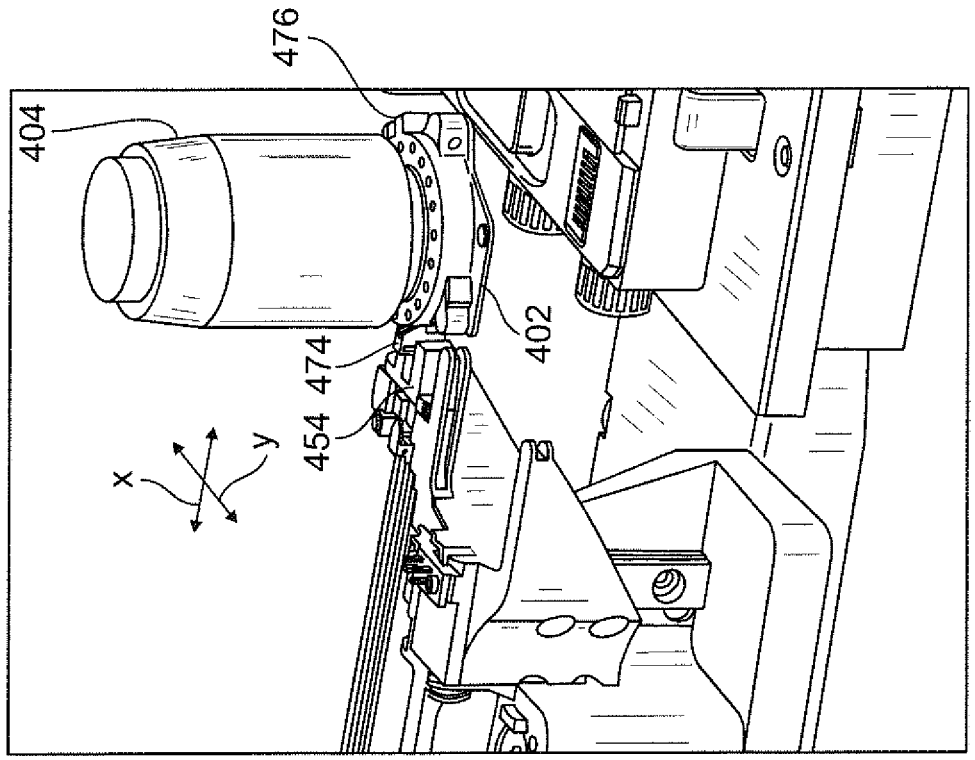
FIG. 20 is a perspective view of the transfer device and illustrates a mechanism for confirming that the path compensator has been removably coupled to the objective lens.

FIG. 20 illustrates a mechanism for confirming that the path compensator 402 has been removably coupled to the objective lens 404 and is properly placed in the imaging position. After removably coupling the path compensator 402 to the collar 476, the transfer device 400 may be relatively moved along the x- and y-axes. The transfer device 400 may be moved so that the projection 474 is detected by the confirmation sensor 454. Once confirmed, the objective lens 404 may then scan the sample 412 during an imaging session.

To remove the path compensator 402, the transfer device 400 may be moved to the engaged position shown in FIG. 16. The movable platform 434 may be moved in an axial direction along the viewing axis 444. The arms 446 and 448 may grip the projections 471 and 473 respectively and provide a separating force in a direction that is opposite to the coupling force F. The separating force exceeds the coupling force F and pulls the path compensator 402 away from the collecting end 406 of the objective lens 404. When the weight W of the path compensator 402 exceeds the coupling force F, the path compensator 402 may fall within the component-reception region 450 and be freely held by the arms 446 and 448 once again.

Figure 21:
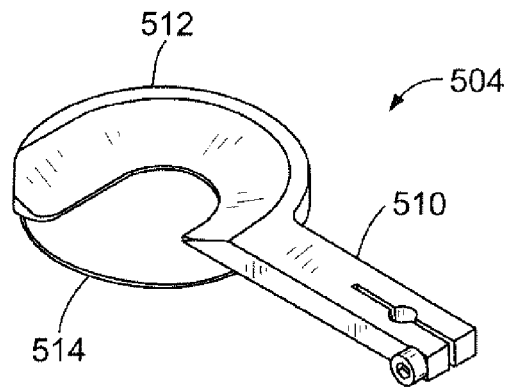
FIGS. 21-23 illustrate a transfer device formed in accordance with an alternative embodiment.
Figure 22:
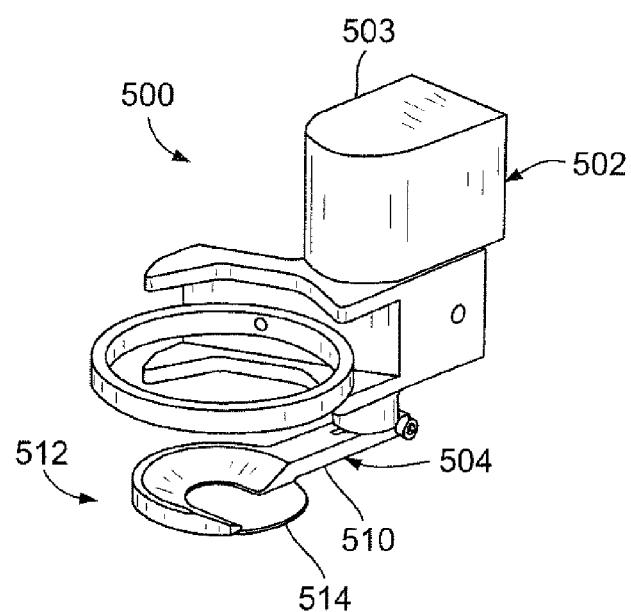
Figure 23:
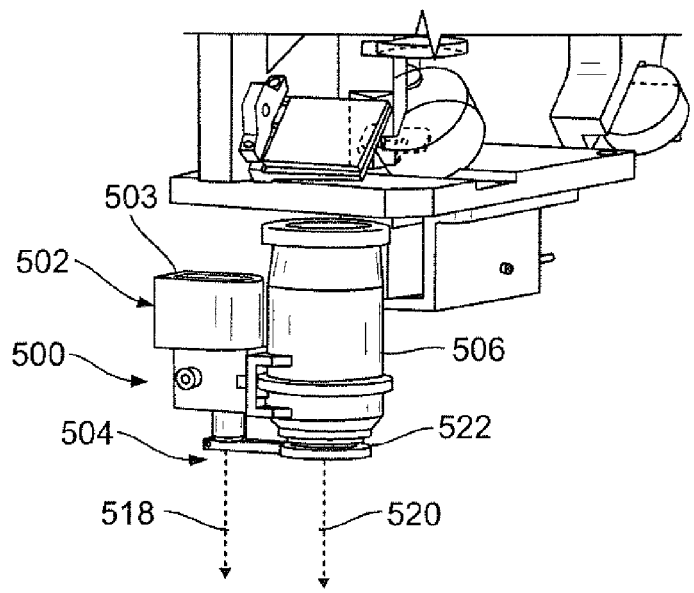

FIGS. 21-30 provide alternative transfer devices for locating a path compensator between an objective lens and a sample. FIGS. 21-23 illustrate a transfer device 500 (FIG. 22) that includes a shoulder assembly 502 and a path compensator 504 that is rotatably coupled to the shoulder assembly 502. The shoulder assembly 502 is configured to be directly attached to the objective lens 506 (FIG. 23). The shoulder assembly 502 may include a motor 503 that provides a rotational motion for the path compensator 504. As shown in FIG. 21, the path compensator 504 includes a rotatable arm 510 that extends to a distal end and a holder 512 that extends from the distal end of the arm 510. The holder 512 is configured to hold an optical element 514 of the path compensator 504. In the illustrated embodiment, the holder 512 is substantially C-shaped. The optical element 514 may be, for example, an optical flat having a substantially uniform thickness.

As shown in FIG. 23, the path compensator 504 may be rotated about an axis 518 that may extend substantially parallel to a viewing axis 520 of the objective lens 506. In the illustrated embodiment, the optical element 514 moves in a common plane when the path compensator 504 is rotated. The holder 512 may be sized and shaped to avoid contacting a collecting end 522 of the objective lens 506. In FIG. 23, the transfer device 500 may be directly supported by the objective lens 506. In such embodiments, the path compensator 504 has a fixed elevational position with respect to the collecting end 522. To selectively move the path compensator 504, the path compensator 504 is rotated about the axis 518.

Figure 25:
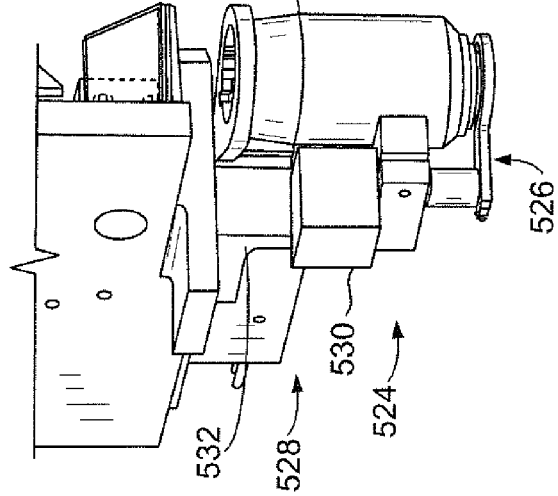
FIGS. 24-25 illustrate another transfer device formed in accordance with an alternative embodiment.
Figure 24:
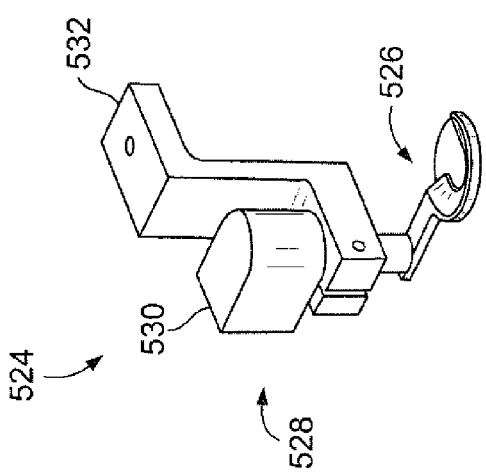

FIGS. 24 and 25 provide a transfer device 524 that is similar to the transfer device 500 (FIG. 21). The transfer device 524 includes a path compensator 526 that is operatively coupled to a shoulder assembly 528 having a motor 530. However, the shoulder assembly 528 also includes a bracket 532 that directly attaches to a frame of the workstation. As such, the path compensator 526 may have a fixed relationship with respect to the objective lens 534 during an imaging session.

Figure 26:
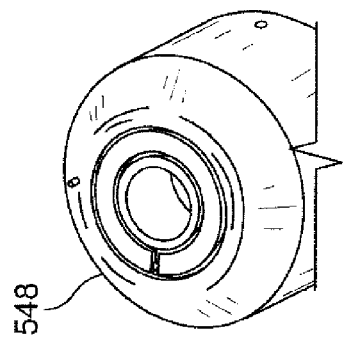
FIGS. 26-28 illustrate another transfer device formed in accordance with an alternative embodiment that utilizes pneumatic forces.
Figure 28:
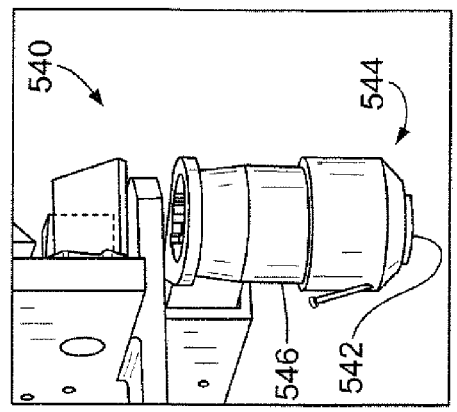
Figure 27:
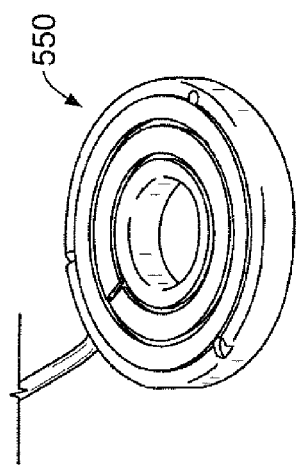

FIGS. 26-28 illustrate a transfer device 540 (FIG. 28) formed in accordance with an alternative embodiment. The transfer device 540 locates and removes a path compensator 542 with respect to a collecting end 544 of an objective lens 546 using pneumatic forces. The path compensator 542 is an optical element that may have, for example, opposite surfaces that define a substantially uniform thickness of the optical element. In the illustrated embodiment, the transfer device 540 includes a vacuum cap 548 (FIG. 26) and a holder 550 (FIG. 27). The opposite surfaces of the optical element may interface with the vacuum cap 542 and the holder 550. The vacuum cap 542 and the holder 550 include respective channels that open up to the surrounding environment. The channels are configured to direct a substantially uniform airflow therethrough. Depending upon the direction of airflow, the optical element may be pushed away from or brought toward the vacuum cap 542. Likewise, the optical element may be pushed away from or brought toward the holder 550 depending upon airflow. As such, the vacuum cap 542 and the holder 550 may cooperate with one another in locating the path compensator 542 in the imaging position proximate to the collecting end 544 of the objective lens 546.

Figure 29:
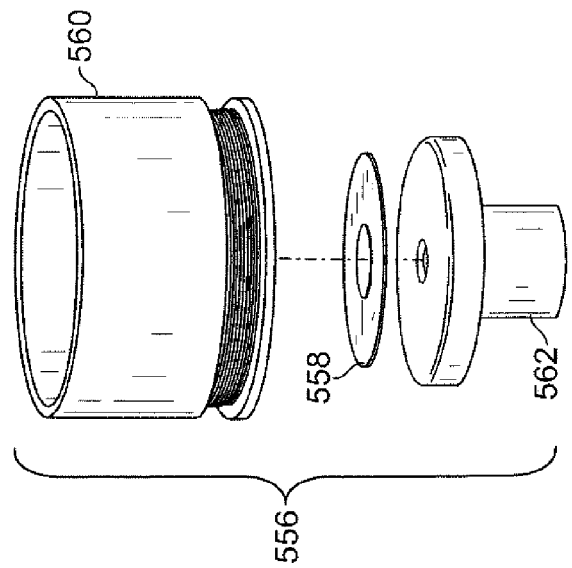
FIG. 29 illustrates another transfer device formed in accordance with an alternative embodiment that uses an electromagnet.

FIG. 29 is an exploded view of a transfer device 556 that may be formed in accordance with an alternative environment. The transfer device 556 uses opposing magnetic forces to locate a path compensator 558 proximate to a collecting end (not shown) of an objective lens (not shown). As shown, the transfer device 556 includes an electromagnetic collar 560 and an electromagnetic holder 562. The electromagnetic collar 560 is configured to attach to the collecting end of the objective lens. When a current flows through an electromagnet, magnetic forces are generated that are a function of an intensity and a direction of the current flowing therethrough. As such, the electromagnetic collar 560 and the electromagnetic holder 562 may cooperate with one another in locating the path compensator 558 in the imaging position proximate to the collecting end.

Figure 30:
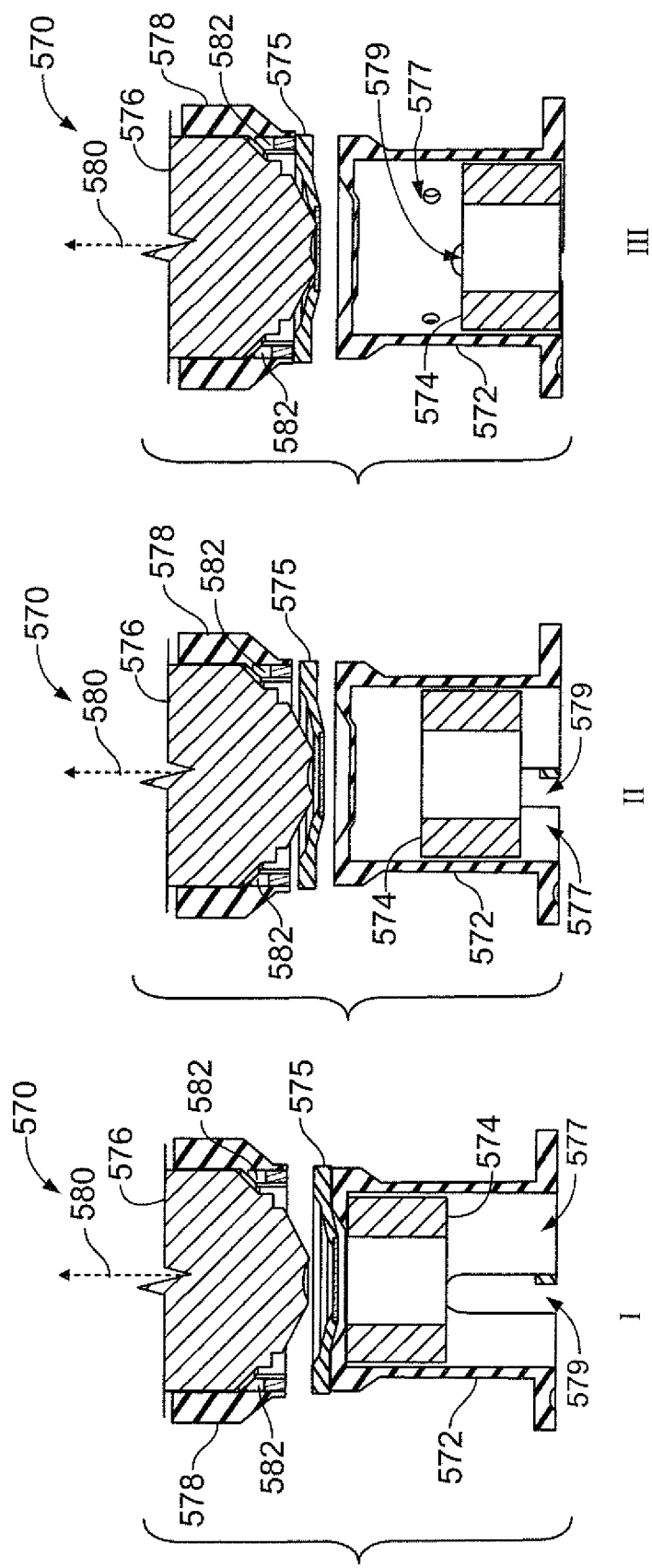
FIG. 30 illustrates another transfer device formed in accordance with an alternative embodiment that uses opposing permanent magnets.

FIG. 30 is a series of cross-sectional views of a transfer device 570 illustrating stages I-III for locating a path compensator 575 with respect to an objective lens 576. The transfer device 570 may be positioned proximate to the objective lens 576 in a similar manner as the transfer device 400 is moved proximate to the objective lens. The transfer device 570 includes a holder 572 that defines a cavity 577 extending along a viewing axis 580 of the objective lens 576. The transfer device 570 also includes a moveable magnet 574 therein that is moveable along the viewing axis 580. The moveable magnet 574 is operatively coupled to an actuator assembly (not shown) through a slot 579 in a wall of the holder 572. Also shown, the objective lens 576 includes a collar 578 that surrounds the objective lens 576 about the viewing axis 580. The collar 578 may have permanent magnets 582 therein.

The path compensator 575 comprises a magnetic material. Accordingly, the transfer device 570 uses magnetic forces to move the path compensator 575 along the viewing axis 580 and locate the path compensator 575 at an imaging position with respect to the objective lens 576. In the imaging position, the path compensator 575 may be removably coupled to the objective lens 576. At stage I, the path compensator 575 is removably coupled to the transfer device 570. More specifically, the moveable magnet 574 is in first position proximate to the path compensator 575 such that the moveable magnet 574 attracts the path compensator 575 away from the objective lens 576 in a direction along the viewing axis 580.

At stage II, the moveable magnet 574 is moved from the first position toward a second position that is further away from the path compensator 575. As the moveable magnet 574 is moved away from the path compensator 575, the magnetic forces between the path compensator 575 and the moveable magnet 574 decrease. At some moment during the transition from the first position to the second position, the magnetic forces that attract the path compensator 575 toward the permanent magnets 582 and the objective lens 576 exceeds a weight of the path compensator and the magnetic forces that attract the path compensator 575 toward the moveable magnet. At such time, the path compensator 575 may move from the holder 572 to the collecting end of the objective lens 576.

At stage III, the moveable magnet 574 is in the second position and the path compensator is removably coupled to the objective lens 576. The transfer device 570 may be moved away from the objective lens 576 to permit the objective lens to image the samples (not shown). To remove the path compensator 575, the transfer device 570 may be positioned proximate to the objective lens 576 and the moveable magnet 574 may move to the first position as shown in stage I. At some moment, the magnetic forces between the moveable magnet 574 and the path compensator 575 exceed the opposing forces and the path compensator 575 is removed from the objective lens 576 onto the holder 572.

Accordingly, transfer devices described herein may reduce or minimize negative effects that could be caused by the objective lens sustaining an impact. The transfer devices may facilitate limiting the total momentum sustained by the objective lens to the mass of the path compensator and the velocity at which the path compensator contacts the objective lens. However, the workstation 200 and other assay systems are not required to use transfer devices that use magnetic or pneumatic forces or that limit the total momentum sustained by the objective lens. Embodiments described herein may use other methods for removably locating the path compensator.

Furthermore, although the various transfer devices have been described with specific reference to removably locating a path compensator with respect to an objective lens, the transfer devices described herein may also be used to removably locate a first optical component with respect to a second optical component. The first optical component may have similar features to one or more of the various path compensators described above and the second optical component may have similar features as the objective lenses described above for removably locating the first optical component with respect to the second optical component. However, the first and second optical components can be different than a path compensator and an objective lens. By way of one example, the first optical component may include a filter and the second optical component may include an optical wedge or lens. The first optical component could also be a mirror. Thus, transfer devices may operatively couple first and second optical components using at least one of, for example, magnetic forces, pneumatic forces, or the pivoting/rotating feature described above.

Figure 31:
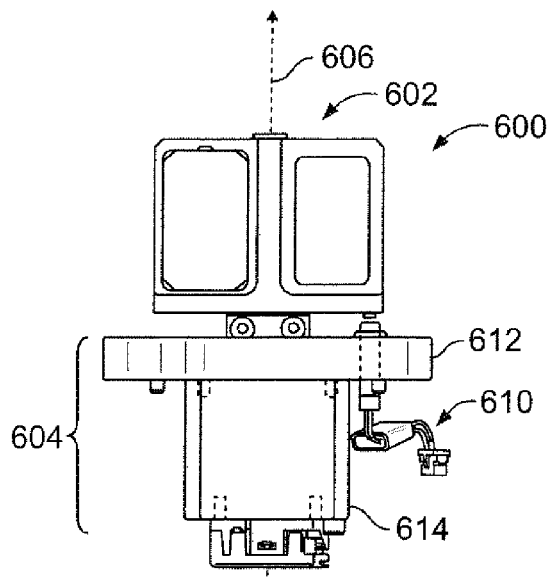
FIG. 31 is a side view of an optical device formed in accordance with one embodiment.

FIG. 31 is a side view of an optical device 600 formed in accordance with one embodiment that may be used in the optical assembly 204 (FIG. 3). The optical device 600 may also be referred to as a filter device since the optical device 600 may be configured to switch-out or exchange filters along an optical path. As described above, embodiments may include modifiable or adjustable optical systems and assemblies. The optical device 600 is an optical component that may facilitate changing a collective arrangement of the optical components. As shown, the optical device 600 includes a device body 602 that is operatively coupled to a motor assembly 604. The motor assembly 604 includes a mounting plate 612 and a motor 614 secured to one another. The device body 602 is rotatable about a rotation axis 606 that extends through the device body 602. When assembled, the rotation axis 606 may extend in a non-parallel manner with respect to a propagation direction of the optical signals. When the device body 602 rotates about the rotation axis 606, the mounting plate 612 may remain stationary. The optical device 600 may also include a position sensor 610 that is configured to facilitate determining a rotational position of the device body 602.

Figure 32:
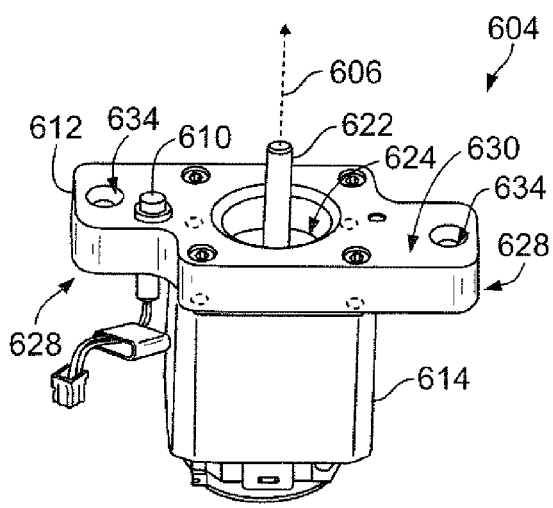
FIG. 32 is a perspective view of a motor assembly that may be used with the optical device of FIG. 31.

FIG. 32 is a perspective view of the motor assembly 604. The motor 614 includes a rod or axle 622 that projects in an axial direction. When the optical device 600 (FIG. 31) is fully assembled, the axle 622 extends along and rotates about the rotation axis 606. In one embodiment, the motor 614 is a stepper motor that rotates about 1.8 degrees per step. However, the motor 614 may also be other types of motors and/or rotate a different amount of degrees/step. Also shown, the mounting plate 612 has a mating surface 630 and includes a bore 624 through which the axle 622 extends. The bore 624 may be sized and shaped to receive a portion of the device body 602. The mounting plate 612 may be secured to the motor 614 through, for example, threaded fasteners such that the mounting plate 612 remains stationary while the device body 602 rotates about the rotation axis 606 (FIG. 31). Also shown, the mounting plate 612 may include extensions 628 that include through-holes 634 for mounting the optical device 600 to stationary components of the workstation 200. Furthermore, the mounting plate 612 may include an opening that is configured to receive the position sensor 610. In one embodiment, the position sensor 610 is a reed sensor (Meder MK11).

Figure 33:
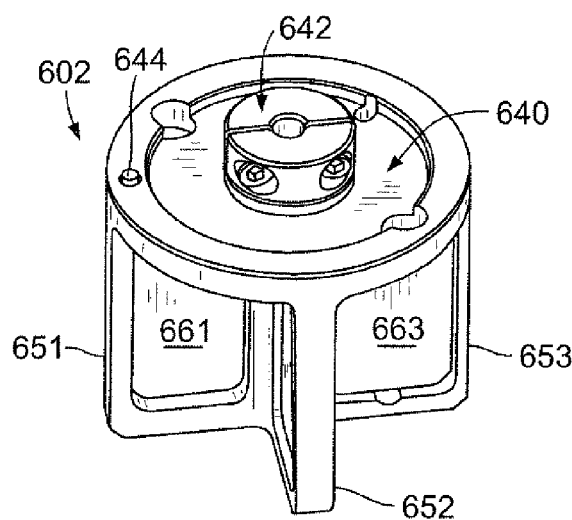
FIGS. 33 and 34 illustrate a bottom perspective view and a side view of a device body that may be used with the optical device of FIG. 31.
Figure 34:
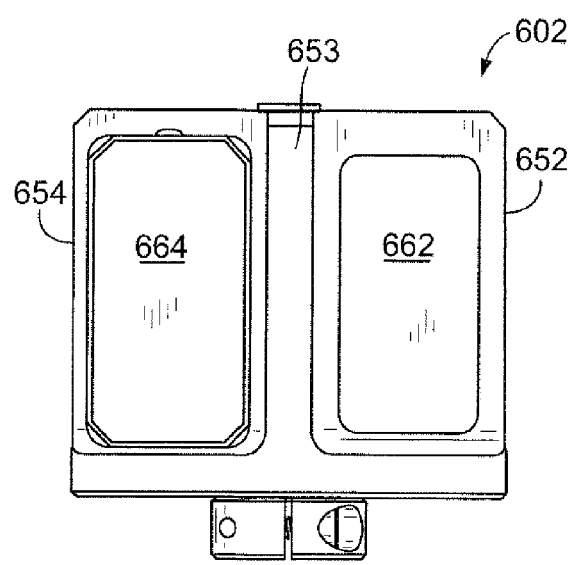

FIGS. 33 and 34 illustrate a perspective view and a side view, respectively, of the device body 602. As shown in FIG. 33, the device body 602 includes a mounting face 640 that is configured to interface with the mating surface 630 when the optical device 600 is fully assembled. The device body 602 may include a mechanism for securing the axle 622 to the device body 602. For example, the device body 602 may have a pair of clamping features 642 that are brought together when the axle 622 is inserted therebetween thereby securing the motor assembly 604 to the device body 602. Also shown, the device body 602 may include a magnetic element 644 attached to the mounting face 640. The magnetic element 644 may interact with the position sensor 610 to indicate to a system controller of the workstation 200 that the device body 602 is in a predetermined or home position.

As shown in both FIGS. 33 and 34, the device body 602 may include a plurality of window frames 651-654 that are affixed to corresponding optical components 661-664. The window frames 651-654 may form a cross-like structure such that adjacent window frames extend perpendicular to each other. The window frames 651-654 are configured to hold the optical components 661-664 in fixed orientations with respect to the rotation axis 606. The optical components 661-664 may include any optical components that are capable of being held by the device body 602. For example, the optical components 661-664 may include bandpass filters, reflectors, beamsplitters, and/or optical wedges. In particular embodiments, the device body 602 includes at least one bandpass filter and at least one optical wedge.

When the optical components 661-664 comprise bandpass filters, the bandpass filters may extend along respective planes. The planes may intersect each other substantially at the rotations axis 606. The respective planes may intersect each other at an angle of at least about 90°. When an optical device selectively rotates about the rotation axis 606 to a rotational position so that at least one bandpass filter is in the optical path, the planes of the bandpass filters may not be perfectly orthogonal to the propagation direction of the optical signals. Such a configuration may reduce reflection of the optical signals back to the excitation light sources.

Figure 35:
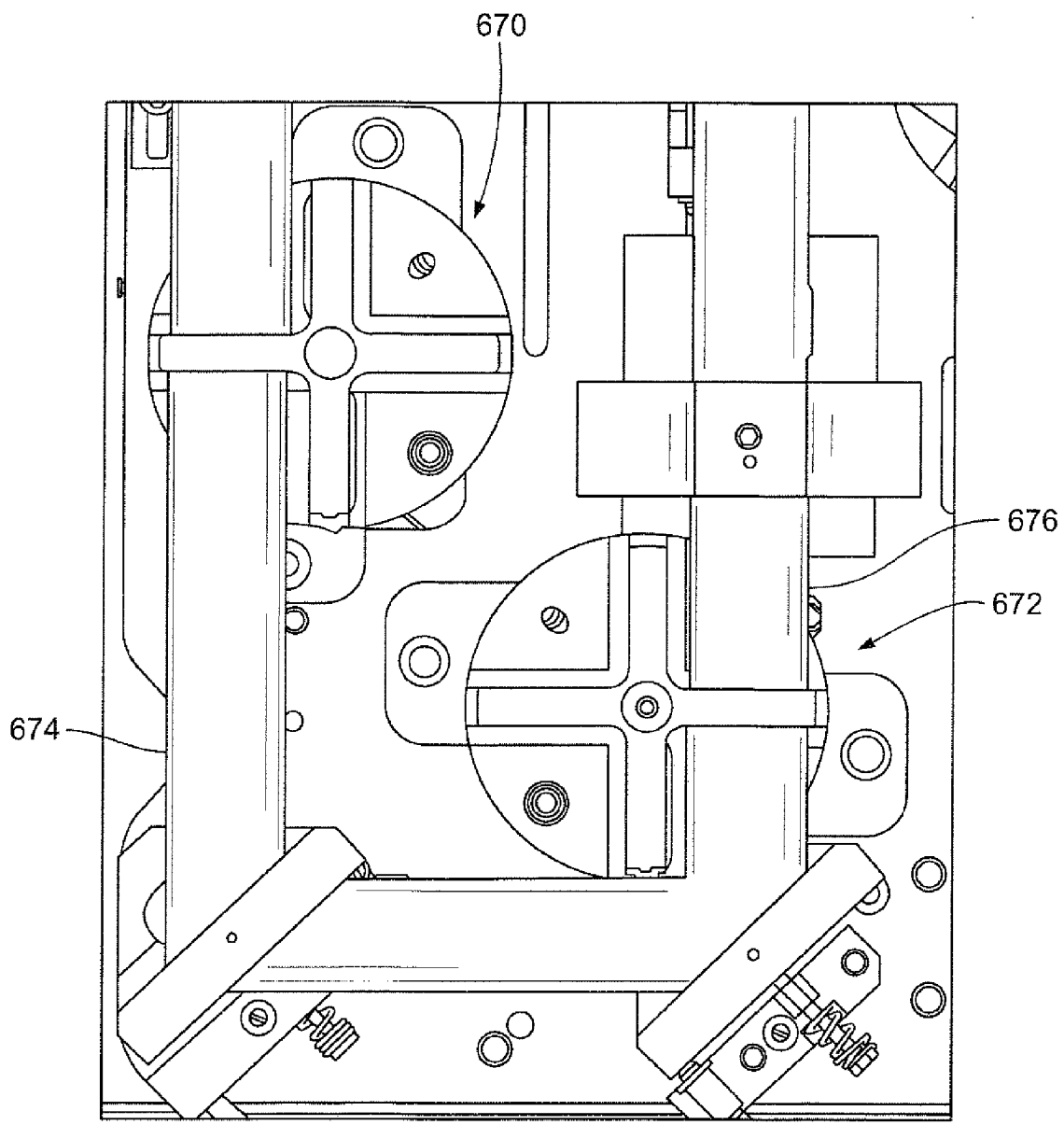
FIG. 35 is a top plan view illustrating rotational positions of the optical devices of FIG. 31.

FIG. 35 illustrates first and second optical devices 670 and 672, which may have similar features and components as the optical device 600 (FIG. 31) described above. As shown, the optical devices 670 and 672 are positioned proximate to different optical paths 674 and 676, respectively. The optical path 674 has a portion of optical signals propagating therealong that have been reflected by a beamsplitter 680, and the optical path 676 has a portion of optical signals propagating therealong that have been transmitted by the beamsplitter 680. As will be described in greater detail below, the first and second optical devices 670 and 672 are configured to selectively rotate about respective rotation axes to predetermined rotational positions. The rotational positions may be based upon a selected assay protocol that the workstation 200 desires to implement. For example, the first optical device 670 may have a rotational position such that the corresponding optical signals propagate through a bandpass filter, and the second optical device 672 may have a rotational position such that the corresponding optical signals propagate through an optical wedge and a bandpass filter. If the assay protocol is changed, one or both of the first and second optical devices 670 and 672 may be selectively rotated to a new rotational position thereby changing the collective arrangement of the optical assembly.

Figure 36:
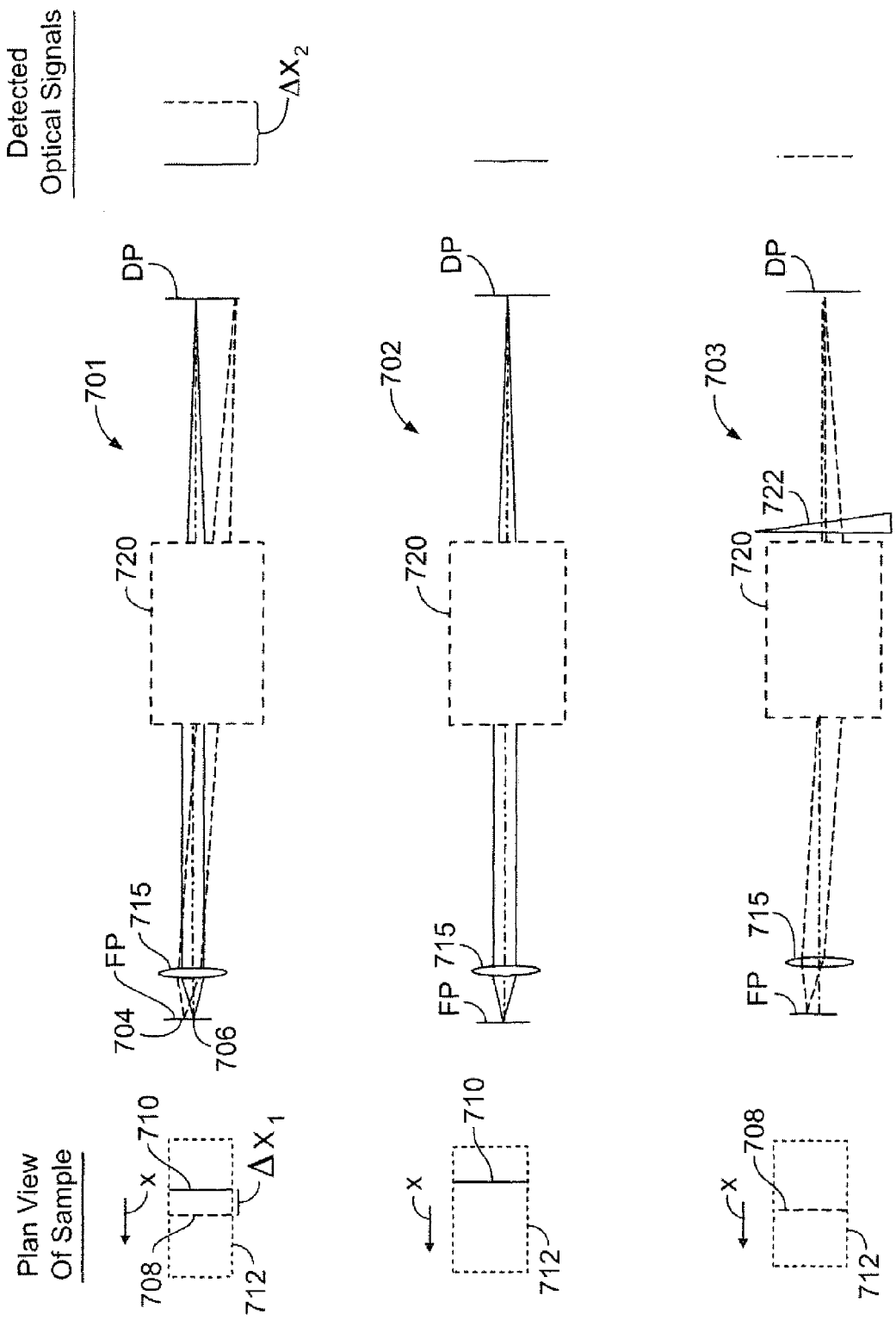
FIG. 36 illustrates different optical configurations that may be used with various embodiments.

FIG. 36 illustrates different techniques 701-703 for providing incident light onto a sample 712. In some embodiments, the excitation source assembly may include at least two different excitation light sources. The different excitation light sources may have different excitation spectra and be configured to illuminate different scan regions 704 and 706 of the sample 712. The different scan regions 704 and 706 may be spatially offset from each other a distance along a focal plane FP of the objective lens 715. Spatially offsetting the scan regions 704 and 706 may facilitate reducing unwanted effects from bleed-through or crosstalk. The sample 712 may be positioned proximate to the focal plane FP. When optical signals are provided (e.g., emitted) by the sample 712, the optical signals propagate through the objective lens 715 and an optical assembly 720. The optical assembly 720 may include a plurality of optical components that are configured to direct the optical signals toward the detection plane DP where sample detectors (not shown) may detect the optical signals.

As shown in FIG. 36, the imaging technique 701 includes simultaneously illuminating scan regions 704 and 706 during an imaging session. The imaging technique may be used, for example, when scanning an exterior surface of a sample (e.g., microarray). In the illustrated embodiment, the scan regions 704 and 706 are linear scan regions that provide lines 708 and 710 of illumination along the sample 712. (For illustrative purposes, the lines and scan regions are distinguished by dashed and solid lines.) In such embodiments, the linear scan regions may move across the sample 712 as indicated by the arrow X such that one scan region illuminates an area of the sample a predetermined time period before the other scan region illuminates the same area. Due to the spatial offset $\Delta X_1$ of the scan regions 704 and 706, the optical signals to be detected by the detector assembly also have a spatially offset $\Delta X_2$ at a detection plane DP. However, the spatial offset $\Delta X_2$ at the detection plane DP of the detector assembly may be greater than the spatial offset $\Delta X_1$ at the focal plane FP due to magnification of the optical signals. In some embodiments, separate sample detectors may be used to detect the separate optical signals. As such, the sample detectors may be spaced apart from each other in a predetermined manner so that the sample detectors detect the spatially offset pair of optical signals from the sample.

However, in some embodiments, it may be desirable to separately illuminate the sample 712 with the different excitation light sources. The imaging technique 702 illustrates the sample 712 being separately illuminated by a first excitation light source. The first excitation light source may have, for example, an excitation wavelength of about 660 nm. The imaging technique 703 illustrates the sample 712 being separately illuminated by a second excitation light source. The second excitation light source may have, for example, an excitation wavelength of about 532 nm. In FIG. 36, the optical signals of the imaging techniques 702 and 703 are incident at the detection plane at only one location. However, in other embodiments, the optical signals from the sample 712 may include first and second optical signals having different emission spectra. In such cases, the optical assembly 720 may be configured to separate the first and second optical signals along different optical paths and direct the first and second optical signals to different locations along the detection plane DP.

In some embodiments, the first excitation light source may illuminate a portion of the sample 712 from a first or start position to a second or stop position. After illuminating the portion with the first excitation light source, the objective lens and the sample 712 may move relative to one another so that the second excitation light source may illuminate the portion of the sample 712 from the start position to the stop position. In other embodiments, the entire sample 712 is illuminated by the first excitation light source and then illuminated by the second excitation light source.

As shown in FIG. 36, the optical signals from the sample 712 in the imaging technique 702 propagate along a common optical path with respect to the same optical signals in the imaging technique 701. However, the optical signals from the sample 712 of the imaging technique 703 are redirected by an optical component 722 so that the optical path of the optical signals is adjusted and the optical signals are incident upon a different location on the detection plane DP. The optical component may be, for example, an optical wedge 722. As will be described in greater detail below, it may be desirable to redirect the optical signals provided by the sample 712 as shown with respect to the imaging technique 703.

Figure 37:
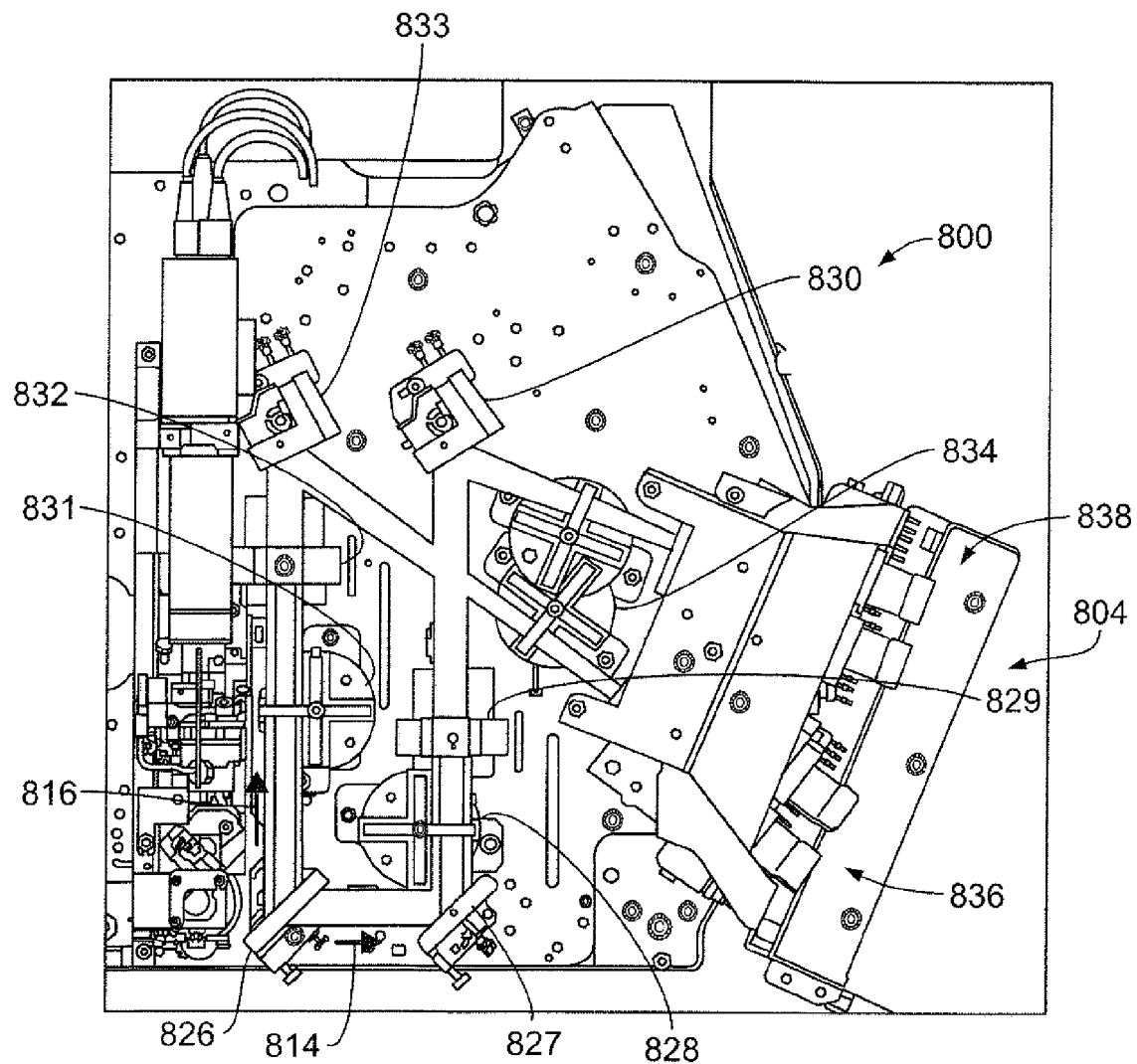

FIGS. 37 and 38 illustrate a top plan view of an optical assembly 800 and a diagram of the optical assembly 800, respectively, formed in accordance with one embodiment. The optical assembly 800 includes a plurality of optical components 821-832 that are located and oriented with respect to one another to form a plurality of optical paths from a sample 802 (FIG. 38) to a detector assembly 804. In some embodiments, optical signals provided by the sample 802 may be affected in different manners based upon a collective arrangement of the optical components 821-832. In particular embodiments, the optical signals provided by the sample 802 may propagate along different optical paths to the detector assembly 804 based upon a collective arrangement of the optical components 821-832.

As shown in FIG. 38, the optical signals provided by the sample 802 may, optionally, propagate through a path compensator 821 before being received by an objective lens 822. The path compensator 821 may be removably positioned between the sample 802 and the objective lens 822 using the various transfer devices described herein. In the illustrated embodiment, the optical signals are light emissions from labels of the sample 802. However, in alternative embodiments, the optical signals may be transmission light that was reflected and/or refracted by the sample 802. Optionally, the optical signals exiting the objective lens 822 may propagate through an afocal compensator 823. The optical signals may then propagate through a dichroic reflector 824 toward a reflector 825. The reflector 825 directs the optical signals toward a beam splitter 826. As shown in FIGS. 37 and 38, the beam splitter 826 may transmit a portion of the optical signals (referred to herein as first optical signals) along a first optical path 814 or reflect a portion of the optical signals (referred to herein as second optical signals) along a second optical path 816. The portions transmitted and reflected (or the first and second optical signals) may have different emission spectra.

As shown in FIGS. 37 and 38, the first optical signals propagating along the first optical path 814 may be redirected by a reflector 827. Optionally, the first optical signals are affected by an optical device 828 that is positioned proximate to the first optical path 814. The optical device 828 may be similar to the optical device 600 described above. The optical device 828 may include a plurality of optical components, such as bandpass filters, compensators, and optical wedges. The first optical signals may then propagate toward a projection lens 829. The projection lens 829 is configured to focus the first optical signals onto a corresponding sample detector 838 of the detector assembly 804. The first optical signals are then redirected by a reflector 830 and projected onto the sample detector 838.

Likewise, the second optical signals propagating along the second optical path 816 may, optionally, be affected by an optical device 831. The optical device 831 may be similar to the optical device 828. However, the optical devices 831 and 828 may have different optical components and/or arrangements of the corresponding optical components. The second optical signals then propagate toward a projection lens 832 that focuses the second optical signals onto a corresponding sample detector 836 of the detector assembly 804. The second optical signals may be redirected by a reflector 833 and directed towards the sample detector 836. Optionally, an optical device 834 may affect the second optical signals before the second optical signals are incident upon the sample detector 836. For example, the optical device 834 may include one or more parallel plates 870 that adjust the optical path of the second optical signals. In the illustrated embodiment, at least one of the parallel plates 870 may be used during imaging of an open-face substrate, such as a beadchip. However, the parallel plates 870 may be used to image other types of samples.

Furthermore, in some embodiments, the optical device 834 may include a plurality of parallel plates 870A-870C in which each parallel plate has a different value for one quality or parameter (e.g., thickness). During operation, the workstation or a user may determine which thickness of the parallel plate 870 provides the optimal results. By providing a plurality of one type of optical component where each optical component is slightly different than the others (e.g., in thickness, angle of surface for incident light), determination can be made as to which optical component works best with respect to the other optical components in the optical assembly. Thus, the tolerance of the optical system can be increased with regard to adjusting for unwanted variations from the desired features of an optical component(s).

FIG. 39 illustrates in greater detail optical paths taken by different optical signals. In particular embodiments, the optical assembly 800 (FIG. 37) may be used in assay protocols that detect numerous optical signals. For example, the optical assembly 800 may be used during a sequencing protocol in which optical signals corresponding to each nucleotide (e.g., A, T, C, G) are detected. As shown in FIG. 39, the sample 802 may be separately illuminated by first and second incident light beams 840 and 842. The incident light beam 840 may have, for example, an excitation wavelength of 660 nm, and the incident light beam 842 may have, for example, an excitation wavelength of 532 nm.

When the sample 802 is illuminated by the first incident light beam 840, the labels associated with the nucleotides A and C may be excited thereby providing light emissions having optical signals associated with the emission spectra of the corresponding labels. The light emissions propagate from the sample 802 through the dichroic 824. The beam splitter 826 reflects the optical signals provided by the label for nucleotide A and transmits the optical signals provided by the label for nucleotide C. Thus, optical signals for A and C can be detected by different detectors. Subsequently, the second incident light beam 842 may illuminate the sample 802 thereby exciting the labels associated with the nucleotides G and T. The excited labels provide light emissions having optical signals associated with the emission spectra of the corresponding labels. The beam splitter 826 reflects the optical signals provided by the label for nucleotide G and transmits the optical signals provided by the label for nucleotide T. In this configuration, G and T signals can be detected by separate detectors.

In alternative embodiments, the first and second incident light beams 840 and 842 may simultaneously illuminate the sample 802. When the sample 802 is simultaneously illuminated by the first and second incident light beams 840 and 842, the labels corresponding with all four nucleotides G, T, A, C provide corresponding light emissions. The light emissions may be subsequently filtered by the optical assembly 800.

In order to perform different assay protocols or different imaging sessions, the assay systems and workstations described herein may selectively move one or more optical components of an optical assembly. By selectively moving at least one optical component, embodiments described herein may effectively change a collective arrangement of the optical assembly. Different collective arrangements may have different effects on the optical signals provided by the sample. For example, with respect to FIG. 38, the optical device 831 may be selectively rotated to change the filter that filters the optical signals propagating along the second optical path 816. As another example, the path compensator 821 may be located between the objective lens 822 and the sample 802 to adjust the focal region along the sample 802. As yet another example, the optical devices 831 and/or 828 may be selectively rotated so that an optical wedge redirects the optical signals propagating along the corresponding optical path. As such, the optical assembly 800 is a reconfigurable optical assembly that is capable of forming a plurality of collective arrangements as desired. Thus, the optical assembly 800 may be used to perform different assay protocols or different imaging sessions.

As described above, in some embodiments, the optical assembly 800 may utilize an optical wedge. As shown in FIG. 38, the optical devices 828 and 831 have window frames 1-4. The window frame 1 of the optical device 831 includes an optical wedge 850 and a bandpass filter 852 attached thereto. The bandpass filter 852 may be attached to the optical wedge 850. Alternatively, the bandpass filter 852 may be coated onto the optical wedge 850. The optical device 831 also includes an optical wedge 854 that is attached to the window frame 2. In some embodiments, the optical wedge 854 is identical to the optical wedge 850 and may be used for calibration or alignment. Window frame 3 of the optical device 831 includes a bandpass filter 856. With respect to the optical device 828, window frames 1 and 4 include optical wedges 860 and 862, respectively, attached thereto. The optical wedge 862 may also be attached to or have a bandpass filter 864 thereon. In some embodiments, the optical wedge 860 is identical to the optical wedge 862 and may be used for calibration or alignment. Window frame 3 of the optical device 828 may have a bandpass filter 866. Also shown in FIG. 38, the optical device 834 only has the parallel plate 870.

Table 1 below provides various collective arrangements for performing different assay protocols or imaging sessions. Each row in Table 1 corresponds to a different collective arrangement. Table 1 describes the position of optical components 821, 823, 828, 831, and 834. (Namely, the path compensator 821, afocal compensator 823, and optical devices 828, 831, and 834.) As described above, the optical devices 831 and 828 have a plurality of optical components that are attached to the window frames 1-4 of each optical device. Table 1 indicates the window frame that is oriented to filter and/or redirect the optical signals for that particular collective arrangement. Table 1 also indicates whether the path and afocal compensators 821 and 823 are located within the associated optical path. In some embodiments, assay protocols may use more than one collective arrangement during operation. For example, the sequencing protocol may use four different collective arrangements. Each collective arrangement corresponds to a separate imaging session.

TABLE 1

| | | Optical Comp 831 | Optical Comp 828 | Optical Comp 834 | Optical Comp 821 | Optical Comp 823 |
|---|---|---|---|---|---|---|
| Sequencing Protocol (Top Surface) | Scan 1 | 4 | 4 | n/a | NO | YES |
| | Scan 2 | 1 | 3 | n/a | NO | YES |
| Sequencing Protocol (Bottom Surface) | Scan 1 | 4 | 4 | n/a | NO | NO |
| | Scan 2 | 1 | 3 | n/a | NO | NO |
| Microarray | — | 4 | 3 | YES | YES | NO |
| Alignment | — | 2 | 1 | In/Out | In/Out | In/Out |

By way of example and with reference to Table 1 and FIG. 38, a sequencing protocol may be performed using the collective arrangements shown in Table 1. More specifically, after the assay system has been calibrated and an appropriate sample has been coupled to the docking system, the assay protocol module may instruct the optical system to perform a first scan of the sample. If the sample includes a flow cell, the assay protocol may instruct the optical system to first scan the top surface of the flow channel. As such, the afocal compensator 823 may be positioned within the optical path between the objective lens 822 and the dichroic 824. During the first scan, a first incident light beam may be incident upon the biological components of the top surface thereby providing optical signals. The optical component 831 has a rotational position such that the bandpass filter 856 of the window frame 4 filters the optical signals propagating along the optical path 816. The optical component 828 has a rotational position such that the optical wedge 862 and the bandpass filter 864 redirect and filter the optical signals propagating along the optical path 814. During the first scan, the light emissions associated with the nucleotides A and C are detected. As such, the labels for the nucleotides A and C may be configured to emit the corresponding optical signals when excited by a common excitation wavelength.

For the second scan of the top surface, the optical device 831 is selectively rotated such that the optical device 831 has a rotational position in which the optical wedge 850 and the bandpass filter 852 redirect and filter the optical signals propagating therethrough. The optical device 828 is selectively rotated to have a rotational position in which the bandpass filter 866 filters the optical signals propagating therethrough. During the second scan, a second incident light beam may be incident upon the biological components of the top surface thereby providing optical signals associated with the nucleotides G and T are detected. The labels for the nucleotides G and T may be configured to emit the corresponding optical signals when excited by a common excitation wavelength. During the first and second scans of the bottom surface, the optical components of the optical assembly 800 may be similarly arranged except that the afocal compensator 823 may be selectively removed. Accordingly, the sequencing protocol uses four different collective arrangements to image the flow cell.

As shown in Table 1, when the assay system images a microarray, such as a beadchip, the assay system performs a single scan of the microarray having the path compensator 821 located within the optical path between the objective lens 822 and the sample 802. The other optical components may be arranged as shown in Table 1. Alternatively, a substrate layer (e.g., coverslip or slide) similar to the substrate layer 227 described above may be used.

Figure 40:
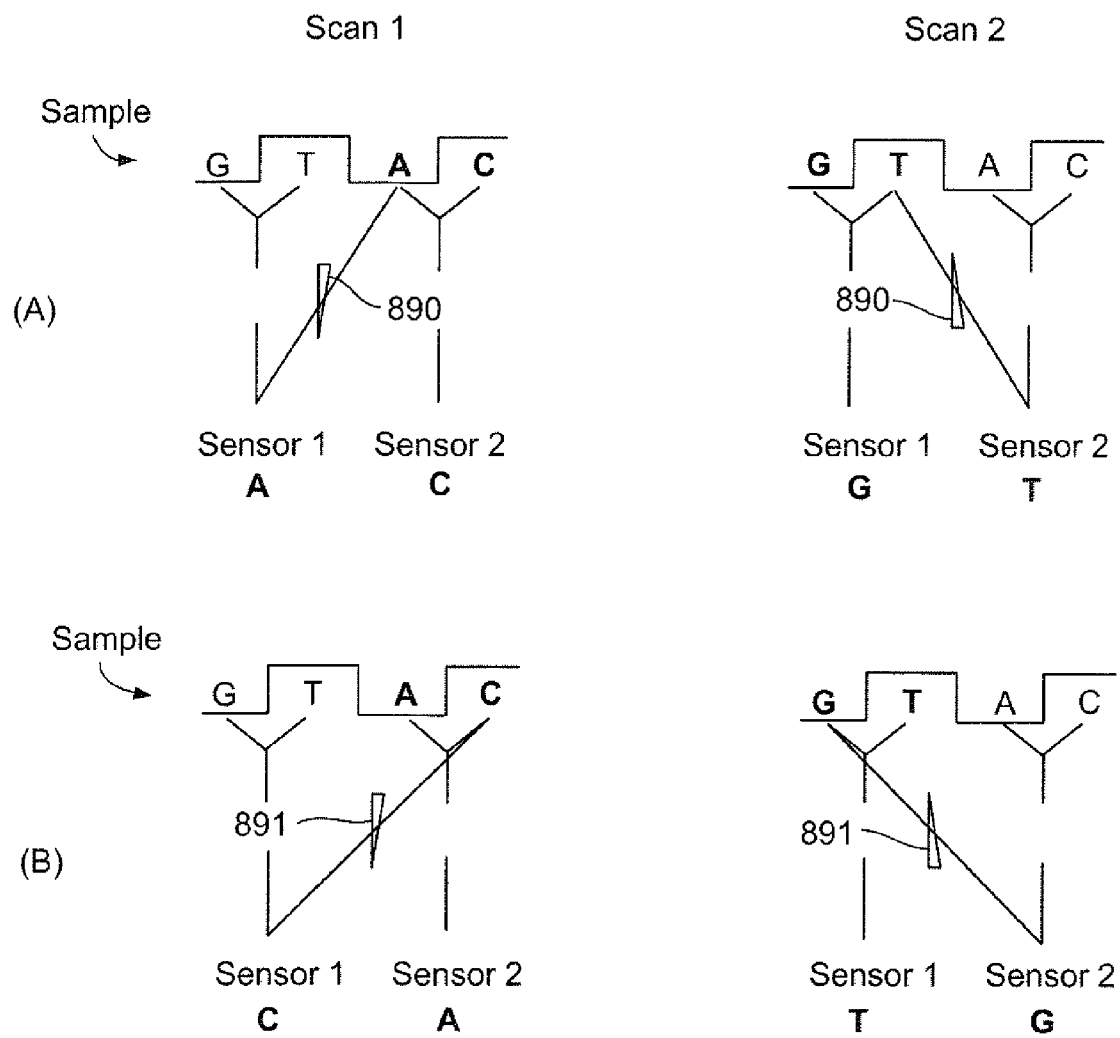
FIG. 40 illustrates various optical configurations that may be used with embodiments described herein.
Figure 41:
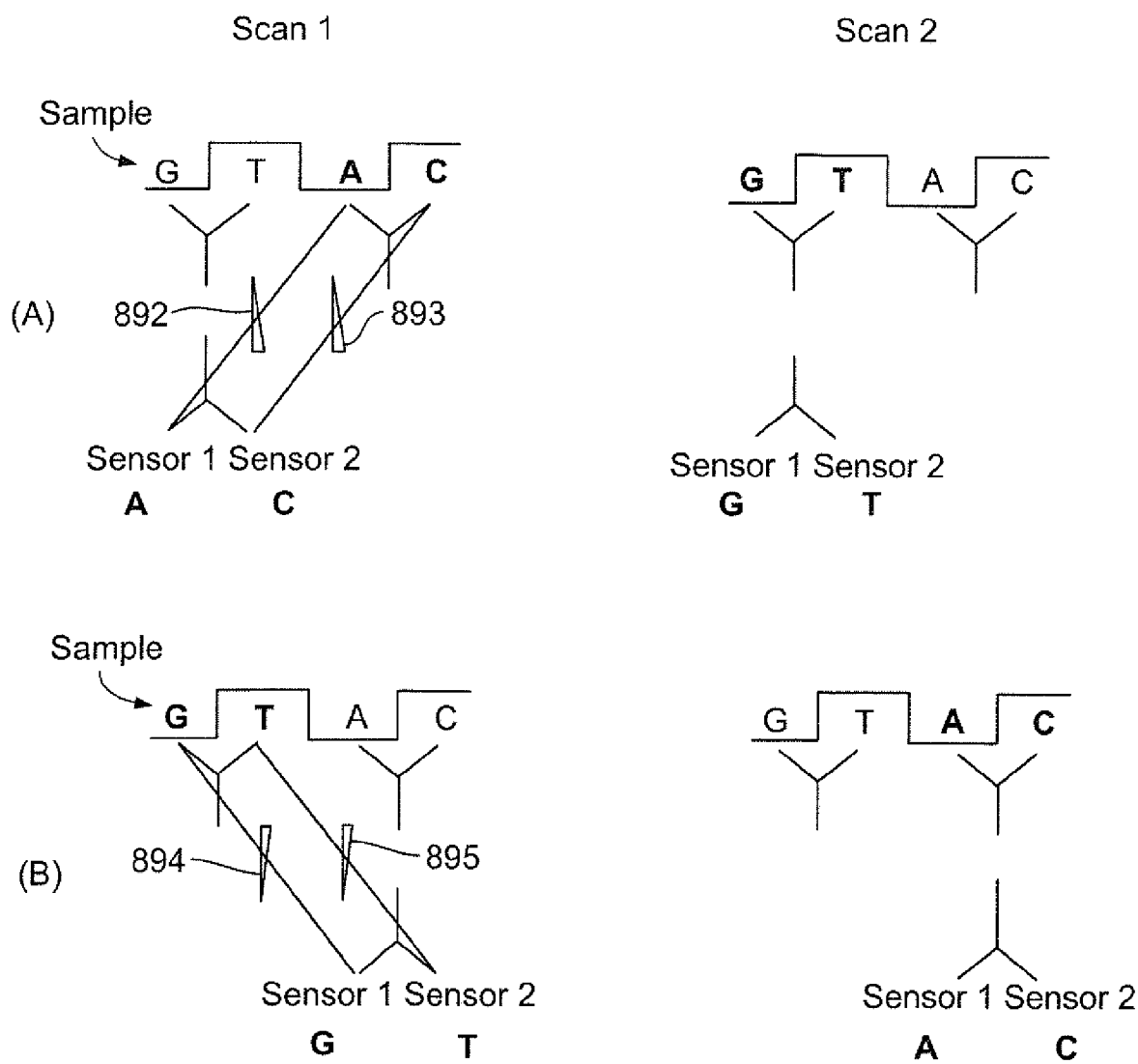
FIG. 41 also illustrates various optical configurations that may be used with embodiments described herein.

FIGS. 40A and 40B illustrate diagrams representing various optical assemblies that may use an optical wedge as shown. FIGS. 41A and 41B also illustrate diagrams representing various optical assemblies that may be used with embodiments described herein. In particular embodiments, as shown in FIGS. 40 and 41, the sample may include nucleotides G, T, A, and C that have associated labels. When the sample is illuminated with an excitation light source, each label fluoresces optical signals that are indicative of the corresponding nucleotide. The optical signals propagate from the sample along an optical assembly (or train) to one of the sensors. The optical assembly may be configured in different ways to direct the optical signals to the sensors. As shown in FIG. 40A, an optical wedge 890 may be used to redirect the optical signals associated with the nucleotide A during a first scan and the same optical wedge 890 may be used to redirect the optical signals associated with the nucleotide T during a second scan. Alternatively, as shown in FIG. 40B, an optical wedge 891 may be used to redirect the optical signals associated with the nucleotide C during a first scan and the same optical wedge 891 may be used to redirect the optical signals associated with the nucleotide G during a second scan.

FIG. 41 illustrates embodiments where a plurality of optical wedges may be used during a single scan and selectively removed from a second scan. Specifically, optical wedges 892-893 may be used to redirect the optical signals associated with the nucleotides A and C during a first scan and the optical wedges 892-893 may be removed from the optical assembly when detecting the optical signals associated with the nucleotides G and T in a second scan. With respect to FIG. 41B, optical wedges 894-895 may be used to redirect the optical signals associated with the nucleotides G and T during a first scan and the optical wedges 894-895 may be removed from the optical assembly when detecting the optical signals associated with the nucleotides A and C in a second scan.

In addition to the various systems, assemblies, apparatuses, and optical components, other embodiments include methods of detecting optical signals or imaging, operating the optical systems and assemblies, and using the various systems, assemblies, apparatuses, and optical components. FIGS. 42-46 provide exemplary methods. The methods of FIGS. 42-46 may be performed by assay imagers and workstations, such as the assay system 100 and the workstation 200. FIG. 42 is a block diagram of a method of operating an optical system that has an objective lens configured to receive optical signals from a sample stage. The method may also be used in operating an assay system or workstation. The sample stage may be configured to receive first and second types of samples. In some embodiments, the different types of sample may be received differently by the sample stage. For example, one type of sample may fluidicly couple to ports of the sample stage to control a flow of fluid through the support structure of the sample. Another type of sample may only mechanically couple to the sample stage.

The method includes locating at 902 an optical path compensator at an imaging position proximate to a collecting end of the objective lens. The path compensator may adjust a focal region associated with the objective lens when in the imaging position. The path compensator may be located at the imaging position using various transfer devices, such as the transfer devices described herein. The path compensator may be operatively coupled such that the path compensator has a fixed relationship with respect to the objective lens. The path compensator may be removably coupled using magnetic and/or pneumatic forces. Optionally, other optical components may be selectively moved to direct the optical signals to the detector assembly. The method also includes performing at 904 a first imaging session to detect optical signals from the first type of sample and removing at 906 the path compensator from the imaging position. The path compensator may be removed by the transfer device. The method also includes performing at 908 a second imaging session to detect optical signals from the second type of sample.

FIG. 43 is a block diagram of a method of detecting light emissions from a sample. The method includes directing at 920 light emissions from a sample along an optical path between an objective lens and a sample detector of the optical system. The method also includes selectively rotating at 922 an optical device about a rotation axis. The optical device is located along the optical assembly or train that directs the optical signals to the sample detector. The optical device may include first and second bandpass filters that filter optical signals differently. The first and second bandpass filters may have fixed orientations with respect to the rotation axis. At least one of the first and second bandpass filters may be positioned within the optical path to filter the light emissions. The light emissions propagate along a beam direction that is non-parallel with respect to the rotation axis.

FIG. 44 is a block diagram of a method of operating an optical system. The method includes illuminating at 930 a sample to generate light emissions that include first and second light emissions having different emission spectra and directing at 932 the first and second light emissions along a common optical path. The method also includes positioning at 934 an optical wedge in the common optical path when the first light emissions propagate therealong. The optical wedge directs the first light emissions so that the first light emissions are incident upon the sample detector. The method also includes removing at 936 the optical wedge from the common optical path when the second light emissions propagate therealong. The second light emissions are incident upon the sample detector when the optical wedge is removed from the optical path.

Figure 45:
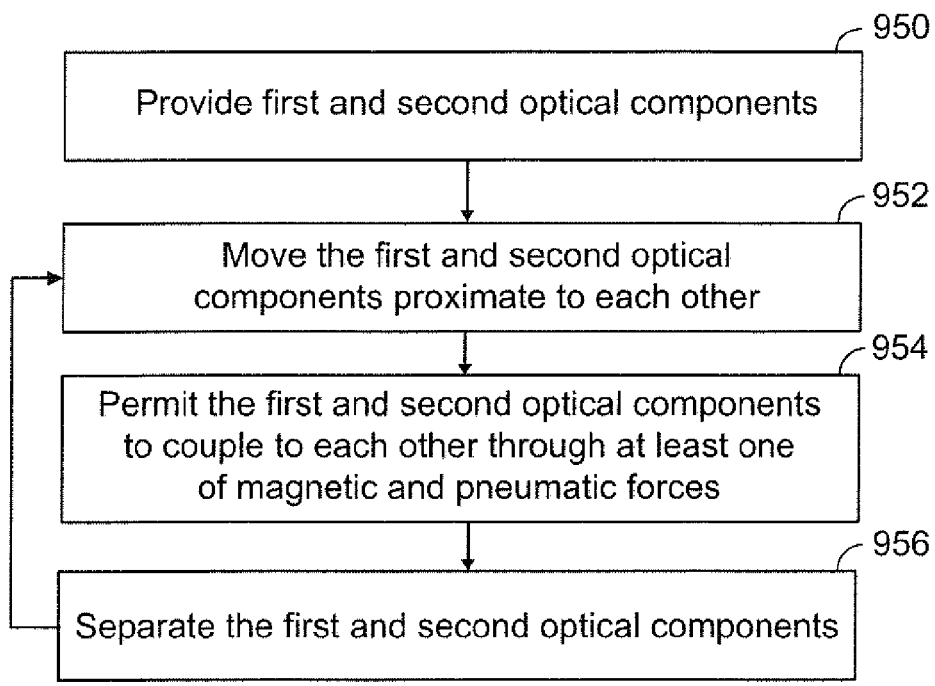
FIG. 45 is a block diagram of a method of operatively coupling two optical components.

FIG. 45 is a block diagram of a method of operatively coupling two optical components. The method includes providing at 950 first and second optical components. In some embodiments, the first optical component is a removable optical component and the second optical component is a stationary optical component. In particular embodiments, the first optical component is a path compensator and the second optical component is an objective lens. The method also includes moving at 952 the first and second optical components proximate to one another and permitting at 954 the first and second optical components to couple to each other through at least one of magnetic and pneumatic forces. The first and second optical components may operatively couple to each other such that the first and second optical components have a fixed relationship. The method may also include separating at 956 the first and second optical components. In some embodiments, the moving at 952, permitting at 954, and separating at 956 may be repeated during, for example, the operation of an assay system or workstation.

Figure 46:
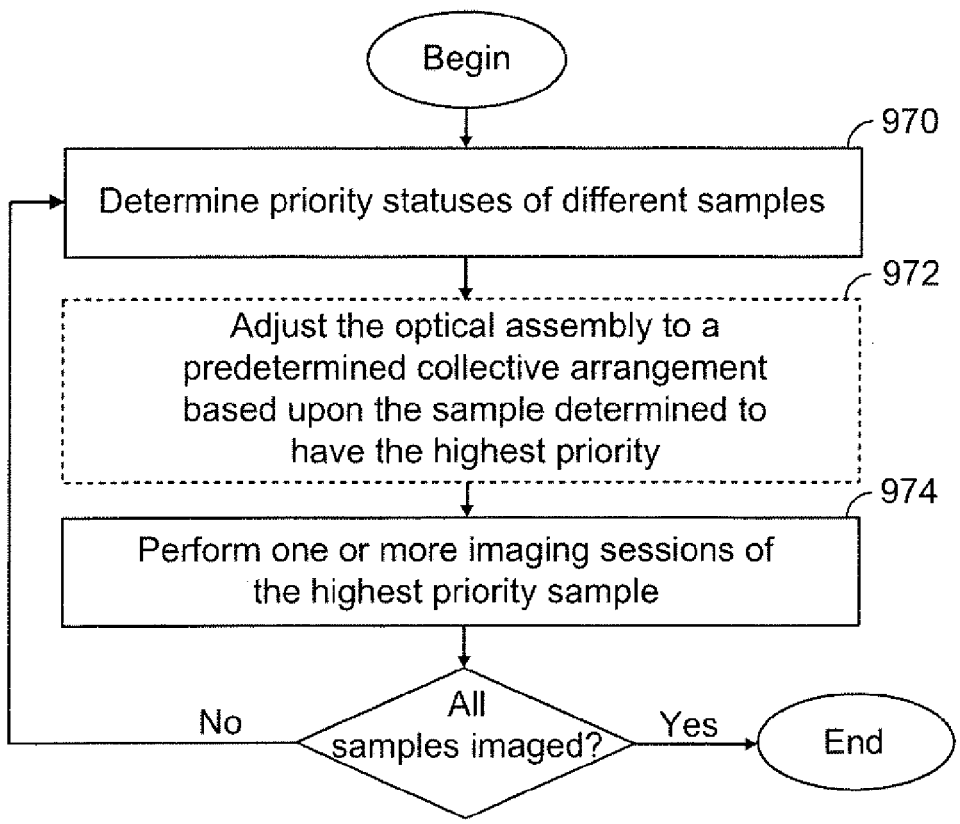
FIG. 46 is a method of operating an assay system that is configured to image at least two different samples.
Figure 47:
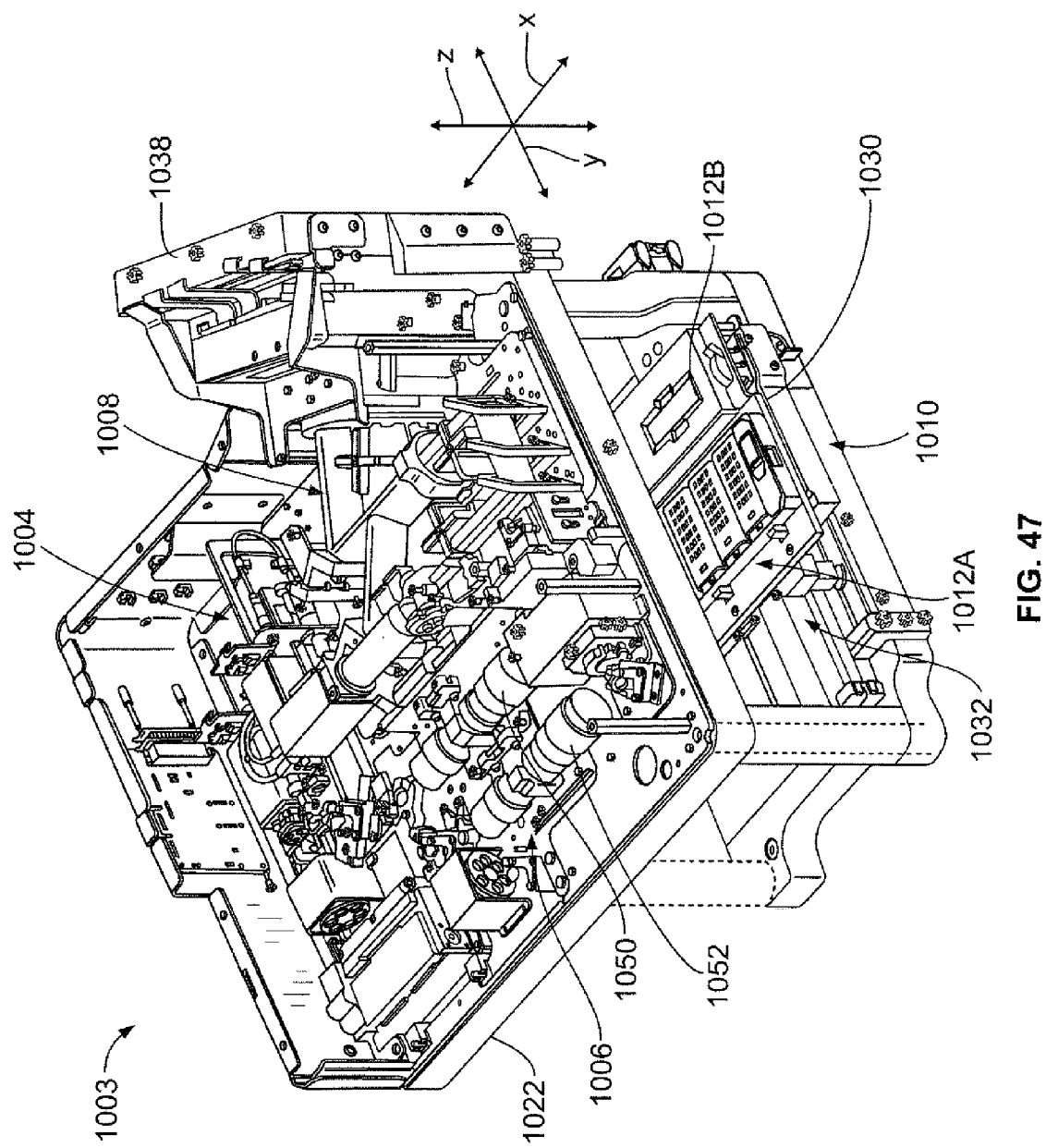
FIG. 47 is an exposed perspective view of a workstation formed in accordance with another embodiment.

FIG. 46 is a method of operating an assay system, such as a workstation, that is configured to image at least two different samples. The method includes determining at 970 priority statuses of different samples loaded into the assay system. The determining operation may be performed by one or more modules of a system controller. In some embodiments, the assay system may automatically identify the samples by, for example, scanning the support structure. Additionally or alternatively, a user of the assay system may provide user inputs to establish a priority status of at least one of the samples.

If the optical assembly is not prepared to image the sample having the highest priority, the assay system may adjust at 972 the optical assembly to a predetermined collective arrangement based upon the sample that is determined to have the highest priority. The collective arrangement may be determined based upon instructions embedded within the system controller. For example, the system controller may have a table, such as Table 1 shown above, stored therein to facilitate determining the collective arrangement to be used. Alternatively or additionally, the user of the assay system may enter user inputs to establish the collective arrangement to be used to image the sample.

The method also includes performing at 974 one or more imaging sessions of the highest priority sample using the collective arrangement. After performing the samples at 974, the assay system may query if all of the loaded samples have been imaged. If not, the assay system may repeat steps 970, 972, and 974. It should be noted that the priority status of a sample may change based upon the state of the sample. For example, if a sample is undergoing a wash cycle for a predetermined time period, the priority status of this sample may be lowered below the priority status of other loaded samples.

By way of example, the assay system may perform a sequencing protocol of a flow cell. After imaging the flow cell for a predetermined time period, the flow cell may undergo a wash cycle. At this time, the priority status of the flow cell may be lowered below the priority statuses of other loaded samples (e.g., open-face substrates, microarrays). In such cases, the assay system may determine that there is sufficient time to image one or more samples while the flow cell is undergoing a wash cycle. The assay system may then image the next sample that has the highest priority status.

FIGS. 47-50 provide an exposed perspective view, front view, and top view, and side view, respectively, of a workstation 1000 formed in accordance with another embodiment. The workstation 1000 may include similar features, components, systems, and assemblies as those described above. As shown, the workstation 1000 includes an optical system 1003 that includes an optical assembly 1004 having an objective lens 1020, a detector assembly 1008, and an excitation source assembly 1006. The workstation 1000 also includes a docking system 1010 and a fluidic control system 1038. The docking system 1010 includes a sample stage 1030 and a motor assembly 1032 that moves the sample stage 1030 in x-y direction and also along a z-direction to and from the objective lens 1020. The workstation 1000 also includes a station frame 1022 that supports all of the components with respect to each other. For example, the optical system 1003 may be positioned over the docking system 1010.

Figure 48:
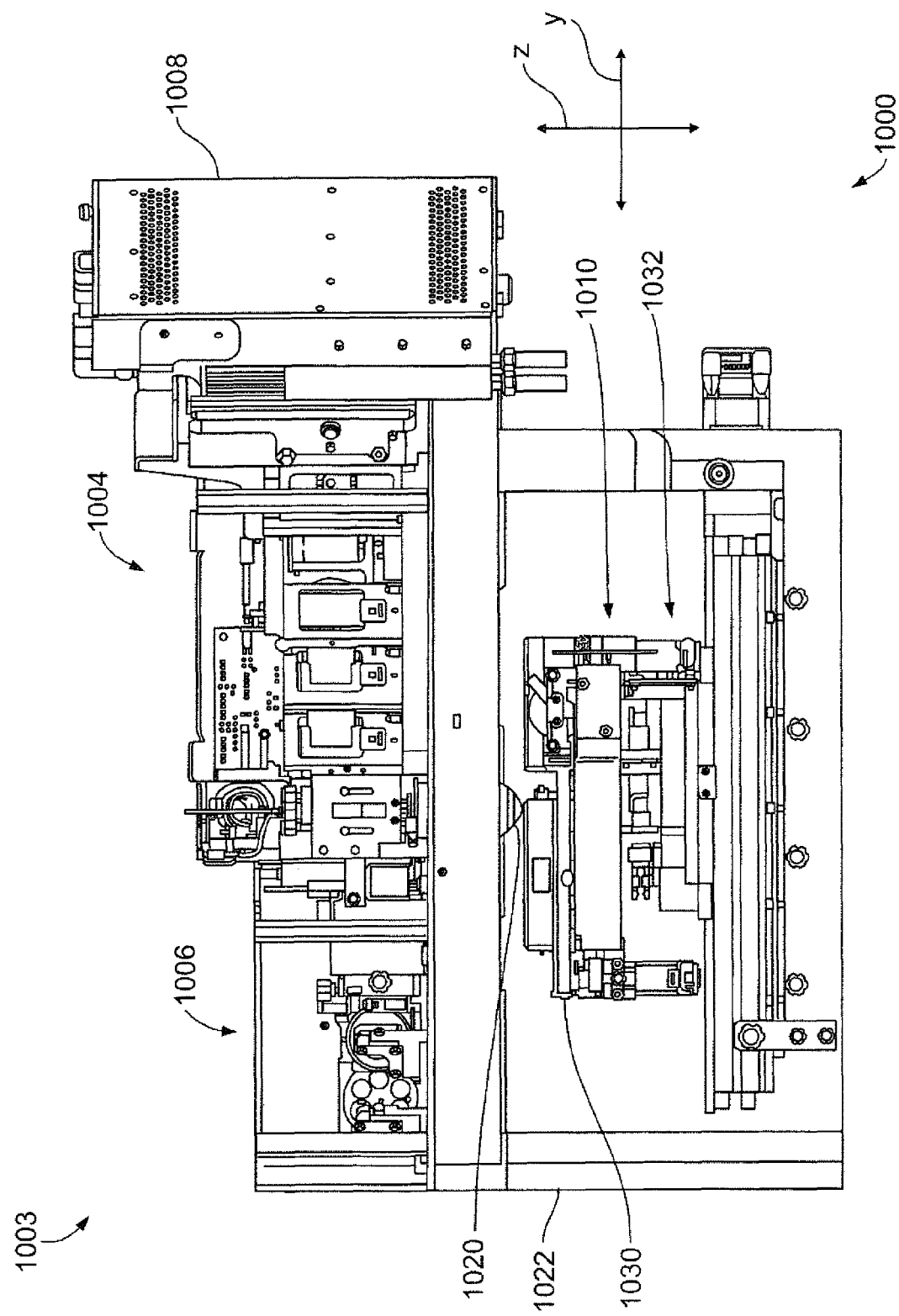
FIG. 48 is an exposed front view of the workstation shown in FIG. 47.
Figure 49:
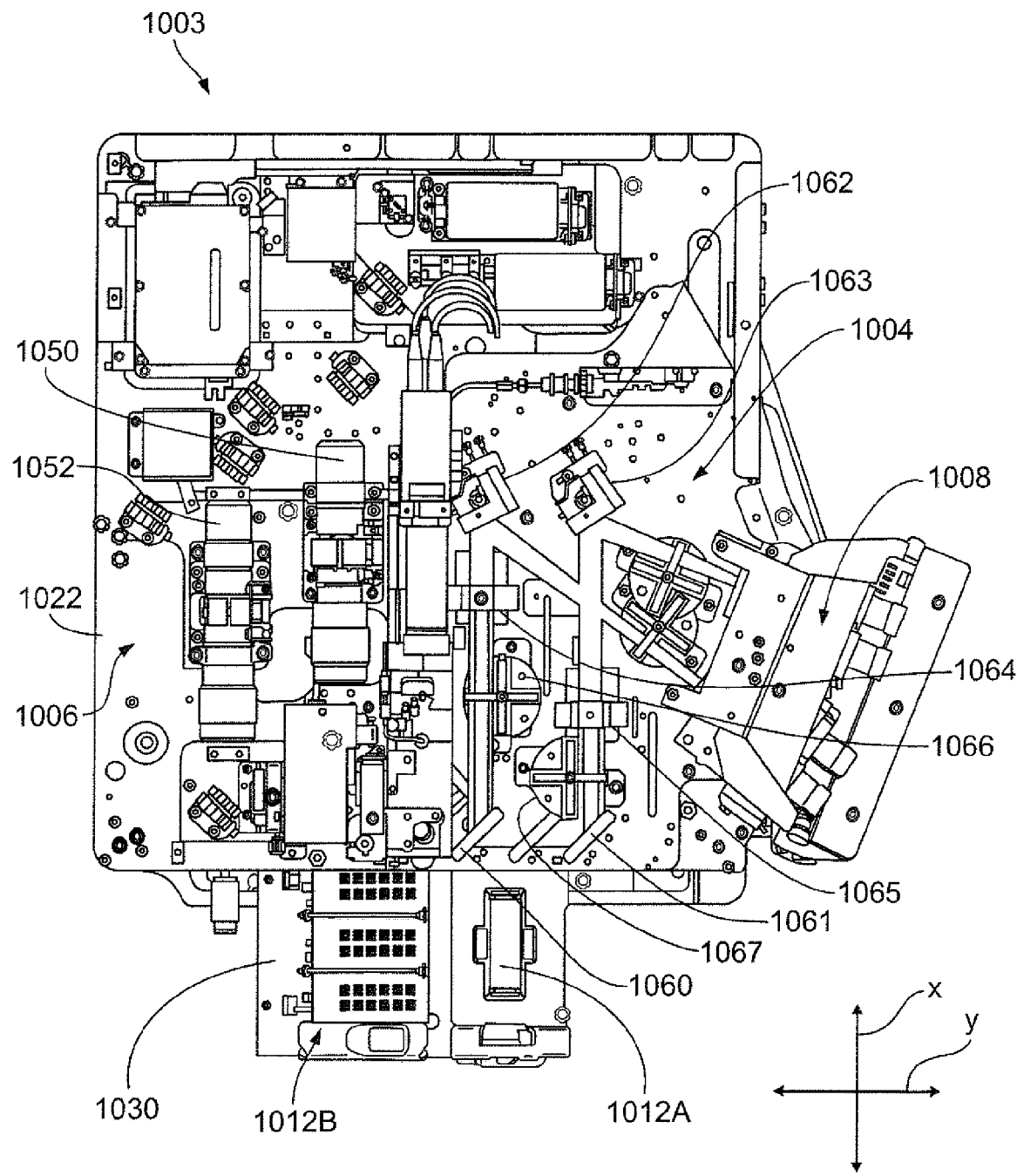
FIG. 49 is an exposed top view of the workstation shown in FIG. 47.

FIG. 49 is a top view of the workstation 1000 and illustrates the optical system 1003 in greater detail. The optical system 1003 includes the excitation source assembly 1006, the detector assembly 1008, and the optical assembly 1004. The excitation source assembly 1006 includes first and second excitation light sources 1050 and 1052. The first and second excitation light sources may be, for example, lasers provided incident light of 660 nm and 532 nm, respectively. The optical assembly 1004 includes a plurality of optical components, such as the objective lens 1020 (FIG. 48), that direct the incident radiation onto samples 1012. The sample 1012A may be a microarray and the sample 1012B may be a flow cell. The detector assembly 1008 may include a plurality of sample detectors. The optical assembly 1004 includes a plurality of optical components that are collectively arranged to direct the optical signals from the sample 1012 to the sample detectors. For example, the optical assembly 1004 may include a beamsplitter 1060, reflectors 1061-1063, projection lenses 1064 and 1065, and optical devices 1066 and 1067.

Figure 50:
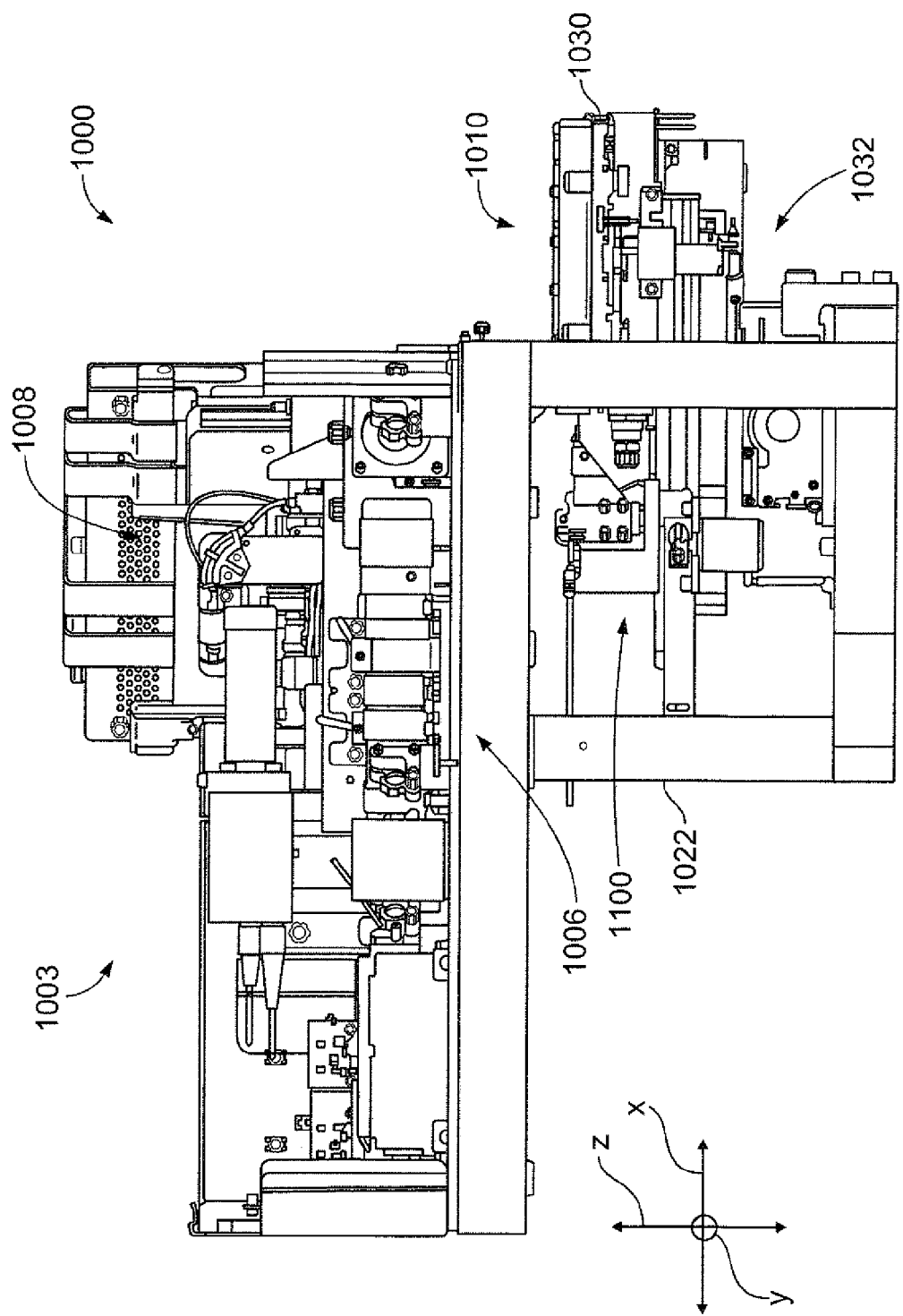
FIG. 50 is an exposed side view of the workstation shown in FIG. 47.

As shown in FIG. 50, in the illustrated embodiment, the docking system 1010 is moveable along a plane formed by the X and Y axes under the objective lens 1020 (FIG. 48). The objective lens 1020 may be stationary and fixed to the frame 1022. As shown, the docking system 1010 may include a transfer device 1100 that has a fixed relationship with respect to the sample stage 1030. The transfer device 1100 may be configured to removably locate a path compensator as described above with respect to the objective lens 1020 during operation of the workstation 1000. When the sample stage 1030 and the transfer device 1100 are moved by the motor assembly 1032, the workstation 1000 may change the positional relationship between the objective lens 1020 and the samples stage 1030. The motor assembly 1032 may move the sample stage 1030 to provide access to the collecting end of the objective lens 1020 so that the transfer device 1100 may removably locate the path compensator.

Figure 51:
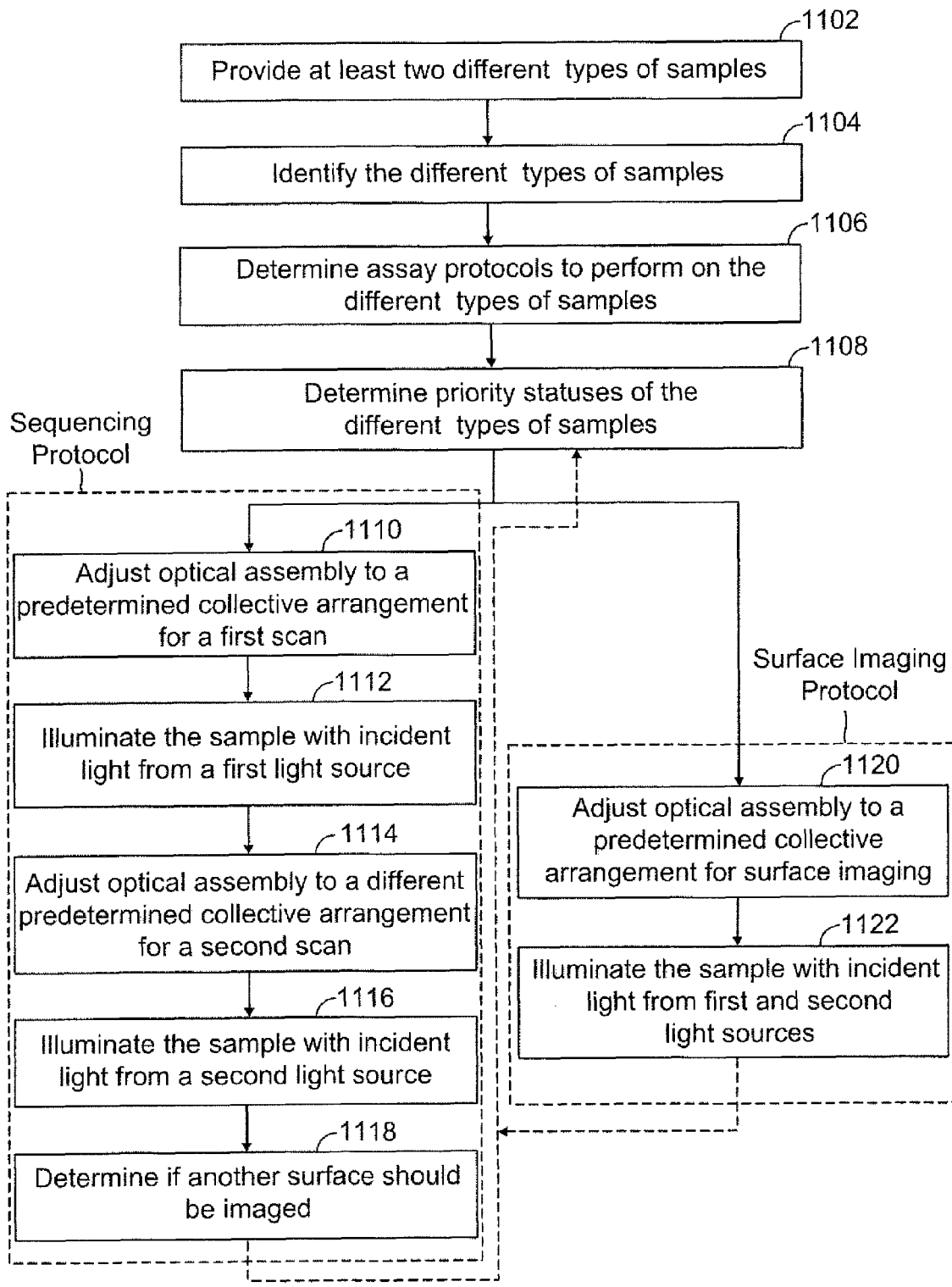
FIG. 51 is a block diagram illustrating a method for operating an assay system or performing a plurality of different assay protocols with a common system.

FIG. 51 is a block diagram illustrating a method of operating an assay system or performing a plurality of different types of assay protocols with a common system or workstation. The method may be performed by, for example, the assay system 100 or the workstations 200 and 1000 and may include at least some steps from the methods described in FIGS. 2 and 42-46. The method may include adjusting optical components of an optical assembly to different collective arrangements, such as those described with reference to Table 1. The assay system may include an excitation source assembly having a plurality of excitation light sources having different excitation wavelengths. The different excitation light sources may be configured along with the optical assembly to illuminate different scan regions that are spatially offset from one another. The optical assembly may include a beamsplitter that is configured to reflect a plurality of different emission spectra (e.g., light emissions of A and G) and also transmit a plurality of different emission spectra (e.g., light emissions of C and T). The assay system may also include a detector assembly having a plurality of sample detectors positioned to detect optical signals that propagate along separate optical path portions.

As shown, the method includes providing at 1102 at least two different types of samples to an assay system. The providing operation 1102 may include mounting the samples onto a sample stage of a docking system. By way of example, the first type of sample may include an open-face support structure having biological or chemical substances immobilized on a surface. The open-face support structure may comprise a microarray. In some embodiments, the different types of samples may engage different interfaces or receptacles.

The second type of sample may include a fluidic support structure that fluidicly couples to the sample stage of the docking system. For instance, the fluidic support structure may comprise a flow cell having a plurality of flow channels. The fluidic support structure may be mounted to an interface on the sample stage that has fluidic ports for engaging the fluidic support structure. The fluidic ports may be in fluid communication with a fluid storage system and operatively controlled by a fluidic support system, such as those described above. When the fluidic support structure is mounted onto a corresponding interface, the fluidic ports of the interface may engage fluidic ports of the support structure. The fluidic control system may control a flow of one or more fluids through the fluidic support structure. Thus, the sample stage may be configured to hold different types of samples.

The method also includes identifying at 1104 the different types of samples. The identifying operation 1104 may occur before or after mounting the different types of samples onto the sample stage. The types of samples may be identified by, for example, a reading device that reads an identifiable feature of the samples. The identifiable feature may be, for instance, a bar code. The samples may also be identified by user inputs entered by a user. The method also includes determining at 1106 assay protocols to perforin on the different types of samples. It may be determined that the first type of sample be subjected to surface imaging and the second type of sample be subjected to a sequencing protocol.

The determining operation 1106 may be performed by a system controller or a protocol module of the assay system. Alternatively or additionally, the determining operation 1106 may include receiving user inputs relating to the assay protocols to perform. The method may also include determining at 1108 priority statuses of the different types of samples as described above. The priority statuses may be determined by a user that is operating the assay system or the priority statuses may be determined by the assay system.

Depending upon the priority status, the assay system may perform the assay protocol for one type of sample or the different assay protocol for another type of sample. In some embodiments, light emissions during the different assay protocols may be directed by a substantially common set of optical components (also referred to as an optical assembly or train). The sequencing protocol begins with adjusting at 1110 the optical assembly to a predetermined collective arrangement for a first scan. The first scan may be for imaging a top surface of one or a plurality of the flow channels at one time. The system controller or an optics adjustment module may instruct the various devices within the optical system to selectively move one or more optical components of the optical assembly for the first scan. For example, the optics adjustment module may instruct a transfer device to insert an afocal compensator as described in International Publication No. WO 2009/137435, which is incorporated by reference in the entirety. The transfer device may also be similar to the transfer devices described herein.

After adjusting the optical assembly to the predetermined collective arrangement for the first scan, the assay system may illuminate at 1112 the sample with incident light having an excitation wavelength. In the illustrated embodiment, the excitation wavelength may be configured to excite two labels (e.g., labels corresponding to A and C nucleotides). The light emissions of A nucleotides and C nucleotides may be directed by the optical train from the sample to different sample detectors. The light emissions may share an optical path from the sample to a beamsplitter that, for example, reflects the light emissions of the A nucleotides and transmits the light emissions of the C nucleotides. The light emissions of the A nucleotides may propagate along a first optical path portion in a propagation direction from the beamsplitter. A bandpass filter located downstream from the beamsplitter and affixed to a rotatable device body of an optical device may filter the light emissions of the A nucleotides. The device body may selectively rotate about a rotation axis that is non-parallel to the propagation direction so that the bandpass filter is located within the first optical path portion. Similarly, the light emissions of the C nucleotides may propagate along a different second optical path portion in a propagation direction from the beamsplitter. An optical device similar to those described above may selectively position an optical component within the second optical path portion where the light emissions of the C nucleotides propagates therealong. The optical component may comprise a bandpass filter and an optical wedge. The bandpass filter filters the light emissions and the optical wedge redirects the light emissions so that the light emissions are incident upon the respective sample detector.

After the first scan, the method may include adjusting at 1114 the optical assembly to a different predetermined collective arrangement for a second scan of the top surface. For example, the system controller (or the optics adjustment module) may instruct the optical devices to selectively rotate to a different rotational position. The optical device proximate to the first optical path portion may selectively rotate so that an optical component having a bandpass filter and an optical wedge is located within the first optical path portion. The optical device proximate to the second optical path portion may selectively rotate so that a bandpass filter is located within the second optical path portion.

The method includes illuminating at 1116 the sample with incident light having an excitation wavelength for the second scan. The scan region of the second scan may have a different location that is spatially offset from the other scan region during the first scan. In the illustrated embodiment, the excitation wavelength may be configured to excite two labels (e.g., labels corresponding to G and T nucleotides). The light emissions of G nucleotides and T nucleotides may be directed by the optical train that directed the light emissions of the A and C nucleotides. Again, the light emissions may share an optical path from the sample to a beamsplitter that, for example, reflects the light emissions of the G nucleotides and transmits the light emissions of the T nucleotides. The light emissions of the G nucleotides may propagate along the first optical path portion in a propagation direction from the beamsplitter. The bandpass filter of the optical device may filter the light emissions and the optical wedge may redirect the light emissions so that the light emissions are incident upon the respective sample detector. Similarly, the light emissions of the T nucleotides may propagate along the second optical path portion in a propagation direction from the beamsplitter. The bandpass filter may filter the light emissions before the light emissions are incident on the respective sample detector. Accordingly, in the illustrated embodiment, the method may include detecting light emissions from four different labels with two separate scans and using a common set of optical components. In some cases, at least two of the optical components may be rotatable to selectively move optical sub-components, such as optical wedges and bandpass filters. The sub-components may be moved into and out of the respective optical path portions.

At 1118, the assay system may determine if another surface should be imaged. For example, the assay system may determine that the bottom surface of the fluidic support structure should be imaged and repeat steps 1110, 1112, 1114, and 1116. For example, during the adjusting operation 1110 for the bottom surface, the optics adjustment module may remove the afocal compensator. After removing the afocal compensator, the method includes re-performing the operations of 1112, 1114, and 1116 to scan the bottom surface.

During the first and second scans of the sequencing protocol, the sample detectors transmit the detection data to the system controller, which may be communicatively coupled to a data storage unit of the assay system or a remote data storage unit through a communication network. In some embodiments, the detection data is analyzed by a detection data analysis module. The analysis module, in some embodiments, may provide a preliminary sample image and/or analysis of the sample image.

After performing the sequencing protocol, the method may re-determine at 1108 the priority statuses of the different types of samples. If the highest priority sample is of the second type then the method may perform a surface-imaging protocol of the second type of sample. As such, the method includes adjusting at 1120 the optical assembly to a predetermined collective arrangement for surface imaging. For example, the optics adjustment module may remove the afocal compensator from the optical path or confirm that the afocal compensator has been removed. The optics adjustment module may also selectively move a path compensator between a collecting end of the objective lens and the sample to be imaged. The path compensator may be removably located by a transfer device as described above. In some embodiments, the transfer device may move the path compensator proximate to the collecting end of the objective lens. The path compensator may be at least one of magnetically and pneumatically moved to an imaging position. The imaging position may be configured for the surface imaging of the sample.

The optics adjustment module may also selectively rotate the optical devices so that each of the first and second optical path portions includes a bandpass filter configured to filter the light emissions propagating therethrough. In the illustrated embodiment, the collective arrangement for surface imaging does not include utilizing optical wedges to redirect the light emissions. However, optical wedges may be used in alternative embodiments.

The method also includes illuminating at 1122 the sample with incident light from the first and second light sources. In the exemplary embodiment, the first and second light sources simultaneously illuminate the sample such that the two spatially offset scan regions illuminate the sample. The labels excited by the first and second light sources during the surface-imaging protocol are configured to be excited by the same excitation wavelengths that excite the labels during the sequencing protocol. In some embodiments, the labels corresponding to the A nucleotides and the labels corresponding to the T nucleotides may be the same labels used during the surface-imaging protocol.

The optical assembly may direct the light emissions from two different labels to separate sample detectors. For example, the light emissions from one label may be reflected by the beamsplitter along the first optical path portion and the light emissions from the other label may be transmitted along the second optical path portion. Both light emissions may be filtered by the corresponding filters and incident upon the corresponding sample detectors. The sample detectors transmit the detection data to the system controller. After performing the surface-imaging protocol, the method may re-determine at 1108 the priority statuses of the different types of samples.

In addition, the assay instrument, optical assembly, and workstation may be formed in accordance with the above description. The following refers to elements from the above description that the elements below may be similar to. However, these references are for illustrative purposes only and are not intended to be limiting. In one embodiment, an assay instrument for detecting optical signals from samples is provided. The assay instrument may be, for example, similar to the assay system 100, the workstation 200, or the workstation 1000 described above. The assay instrument may include a sample stage (e.g., the sample stages 130, 230, or 1030) that comprises a first interface (e.g., the sample interface 240B) and a second interface (e.g., the sample interface 240A). The first interface may include a platform for holding a sample (e.g., the sample 212B) on an open-faced support (e.g., the support structure 213B) and for imaging of an external surface and the second interface comprising a platform for holding a sample (e.g., the sample 212A) in a flow cell for imaging of at least one internal surface. The sample stage is coupled with the flow cell with fluidics connectors.

The assay instrument may also include an optical detector (e.g., the sample detectors 254, 256, 836, 838) for detecting optical signals from the open-faced support and the flow cell. Furthermore, the assay instrument may include a moving mechanism (e.g., the optics adjustment system 120, the transfer devices 400, 500, 524, 540, 556, 570, 1100, the rotatable optical device 600, 670, 672, the motor assembly 232, 1032) for selectively moving one or more optical components including an objective lens (220, 332, 404, 506, 534, 546, 576, 715, 822, 1020). In addition to the objective lens, the one or more optical components may be similar to those described above, such as the path compensators 122, 221, 293, 402, 504, 526, 542, 558, 575, 821; the afocal compensator 823; the optical wedges 722, 850, 854, 860, 862, 890-895; the optical components 821, 823, 828, 831, 834; the bandpass filters 852, 856, 864, 866; and other optical components or devices, such as reflectors and beamsplitters. The one or more optical components can be moved into the optical pathway between the sample stage and the optical detector to either a first configuration for surface-imaging of the open-faced support or a second configuration for imaging the flow cell. FIG. 9 illustrates different configurations, and Table 1 lists examples of such first and second configurations.

The assay instrument may include a fluidic network (e.g., the fluidic network 135) that is coupled with the flow cell with fluidics connectors. The fluidic network may include a fluid storage system (e.g., the fluid storage system 136) that includes reagents for sequencing by synthesis.

In addition, the assay instrument may include a protocol module (e.g., the protocol module 156) for instructing the assay instrument to perform a sequencing by synthesis protocol for the flow cell and for instructing the assay instrument to perform a microarray scanning protocol for the open-faced support. The protocol module can be configured to operate according to priority statuses of the samples whereby lower priority samples are paused when a schedule conflict arises and resumed upon resolving the schedule conflict. A sample in the flow cell may have a higher priority than a sample on the open-faced support.

The assay instrument can have a working distance that exists between the sample stage and the objective lens. The working distance can be less than 1000 microns. The assay instrument may have a resolution that is sufficient to individually resolve the features or sites that are separated by a distance of less than 15 μm.

The objective lens can include (i) a collecting end (e.g., the collecting ends 294, 406, 522, 544) that is positioned proximate to a sample interface on a sample stage and configured to receive optical signals therefrom and (ii) an afocal end, which could be opposite the collecting end of the objective lens, that is configured to transmit the optical signals to a detector. The one or more optical components may also include a first removable path compensator (e.g., the path compensator 821 and others described above) for adjusting an optical path of the optical signals when positioned between the collecting end of the objective lens and the sample and a second removable path compensator (e.g., the afocal compensator 823) for adjusting an optical path of the optical signals when located at an afocal position with respect to the objective lens.

The assay instrument may also include a transfer device (e.g., the transfer devices 400 and others described above) that can be located at a fixed position with respect to the sample stage for moving the first removable path compensator into and out of an imaging position between the collecting end of the objective lens and the sample interface on the sample stage. The transfer device can include a platform assembly (e.g., the platform assembly 414) that can be configured to removably couple the first path compensator to the objective lens. The transfer device may also include a motor assembly (e.g., the motor assembly 232) that is configured to move the sample stage in an x-y direction and also along a z-direction to and from the objective lens and also a bridge member (e.g., the bridge member 430) that is configured to couple the platform assembly to the motor assembly. The first removable path compensator may be configured to adjust the optical path between a configuration for imaging the flow cell and a configuration for imaging the open-faced support. The second path compensator may be configured to adjust the optical path between a configuration for imaging a top surface of the flow cell and a configuration for imaging a bottom surface of the flow cell.

The assay instrument may also include an excitation light source assembly (e.g., the excitation source assemblies 106, 206) comprising first and second excitation light sources. The first and second excitation light sources can be configured to excite the sample during separate first and second imaging sessions, respectively. The sample can generate corresponding light emissions when excited by each of the first and second excitation light sources. The one or more optical components may include a beam splitter (e.g., the beamsplitters 260, 680, 826, 1060) that separates the corresponding light emissions of each of the first and second excitation light sources into reflected and transmitted portions. The transmitted portions of the first and second light emissions being directed along a common transmitted optical path. The reflected portions of the light emissions being directed along a common reflected optical path.

The one more optical components may also include a plurality of optical wedges (e.g., the optical wedges 722, 850, 854, 860, 862, 890-895). Each of the transmitted and reflected optical paths having an optical wedge that is selectively moveable. The optical wedge of the reflected optical path can redirect the reflected portion during the first imaging session, and the optical wedge of the transmitted optical path can redirect the transmitted portion during the second imaging session.

In another embodiment, an optical assembly is provided that may be similar to the optical assemblies 104, 204, 720, 800, 1004. The optical assembly may be used in an assay instrument to assist the detection of optical signals from a sample during imaging sessions. For example, the optical assembly may include an objective lens (e.g., the objective lenses 220, 332, 404, 506, 534, 546, 576, 715, 822, 1020) that includes (i) a collecting end that is positioned proximate to a sample interface on a sample stage and configured to receive optical signals therefrom and (ii) an afocal end configured to transmit the optical signals to a detector. Similar to those described above, the optical assembly may include a first removable path compensator for adjusting an optical path of the optical signals when positioned between the collecting end of the objective lens and the sample and also a second removable path compensator for adjusting an optical path of the optical signals when located at an afocal position with respect to the objective lens.

The optical assembly may include a transfer device (e.g., the transfer devices 400 and others described above) located at a fixed position with respect to the sample stage for moving the first path compensator into and out of an imaging position between the collecting end of the objective lens and the sample interface on the sample stage. The optical assembly may also include another transfer device that is operatively coupled to the second path compensator for moving the second path compensator into and out of an afocal position with respect to the objective lens. This other transfer device can be similar to the transfer devices 400, 500, 524, 540, 556, 570, 1100 described above. The second path compensator may be configured to adjust the optical path between a configuration for imaging a top surface of the flow cell and a configuration for imaging a bottom surface of the flow cell.

In another embodiment, a workstation is provided that is configured to detect optical signals from samples. The workstation may be similar to the workstation 200 or 1000, or the assay system 100 or 1200 (described below). The samples include first and second types of samples. For example, the workstation may include a detector assembly (e.g., the detector assemblies 108, 208, 804, 1008) that is configured to detect the optical signals from first and second types of samples at different sample interfaces on a sample stage. The workstation may also include an optical assembly that includes an objective lens that is positioned proximate to the sample stage. The optical assembly may be configured to receive and direct the optical signals to the detector assembly. The optical assembly may have one or a plurality of selectively moveable optical components. The workstation may also include an excitation light source assembly that is positioned proximate to the objective lens. The excitation light source assembly may include one or more light sources.

Optionally, the light source assembly may include two excitation light sources having different excitation spectra. The workstation may comprise a protocol module that is configured to subject the first and second types of samples to first and second imaging protocols, respectively. Each of the first and second imaging protocols may include illuminating the corresponding sample with at least one of the two excitation light sources and detecting the corresponding optical signals. Furthermore, the workstation may include a moving mechanism for selectively moving the optical components of the optical assembly. The moving mechanism is configured to selectively move the optical components to a first configuration for the first imaging protocol and a different second configuration for the second imaging protocol. Optionally, the first imaging protocol may be a sequencing-by-synthesis protocol and the second imaging protocol is an array scanning protocol.

The moving mechanism may include a device that is rotatable about a rotation axis to position a corresponding optical wedge and/or a corresponding bandpass filter into and out of a corresponding optical path. The moving mechanism could also include a transfer device that is capable of moving the path compensator into and out of an optical path.

Each of the first and second imaging protocols may include illuminating the corresponding sample with no more than two excitation light sources and detecting the corresponding optical signals with no more than two optical detectors. The first imaging protocol may include distinguishing at least two colors simultaneously. The second imaging protocol may include distinguishing at least two colors simultaneously.

Figure 52:
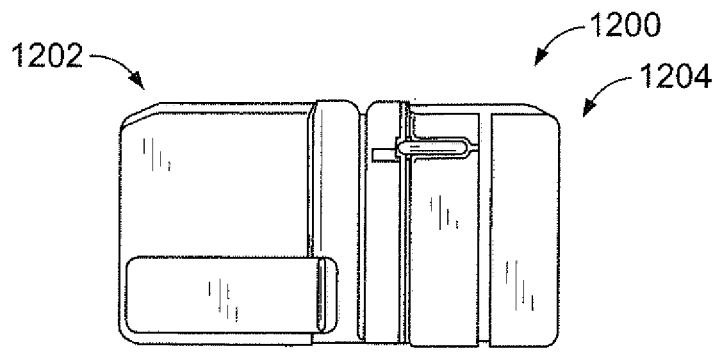
FIG. 52 shows the exterior of an exemplary assay system known as the HiScan SQ assay system.
Figure 53:
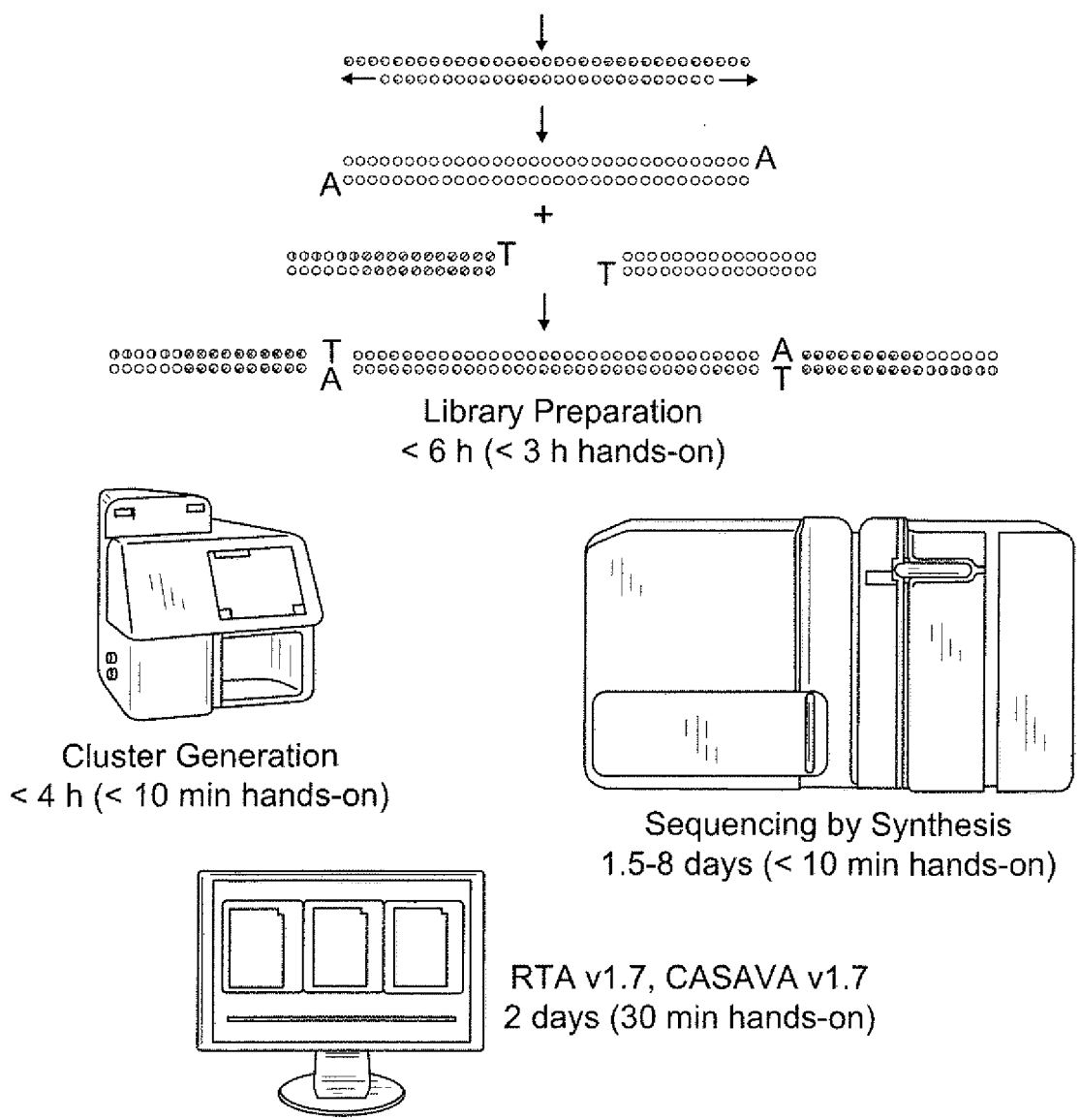
FIG. 53 shows an exemplary sequencing protocol.

FIGS. 52-54 show an assay system (or instrument) 1200 that uses at least some of the various methods, systems, and apparatuses described above. However, it should be noted that the assay system 1200 is merely illustrative of one embodiment and that many other embodiments will be apparent to those of skill in the art upon reviewing the above description. The assay system 1200 shown in FIGS. 52-54 may be configured to perform (a) genotyping and gene expression arrays and (b) sequencing-by-synthesis. The assay system 1200 is commercially known as the HiScan SQ developed by Illumina, Inc. of San Diego, Calif. The assay system 1200 may include a scanner (or reader) 1202 for scanning microarrays and also a fluidics device 1204 that enables sequencing. For example, the scanner 1202 may be the HiScan Reader and the fluidics device 1204 may be the SQ Module. The scanner 1202 may be able to function independently as a microarray scanner that is configured to scan, for example, Illumina's BeadArray™ products. The scanner 1202 is also capable of scanning flow cells for sequencing. With the fluidics device 1204, the assay system 1200 is capable of rapidly switching to perform sequencing-by-synthesis. The fluidics device 1204 may be configured to store and deliver SBS reagents.

The assay system 1200 may allow researchers to (A) leverage targeted resequencing as the ultimate follow-on to genome-wide association studies (GWAS); (B) transition between array-based and sequencing-based gene expression analysis; (C) validate array-based expression and splice variant data; and (D) identify target SNPs from sequencing experiments to design custom genotyping panels.

As described above, the scanner 1202 may be able to function independently to scan microarrays, such as, BeadArray™ products. Microarrays may provide array-based solutions for genotyping, gene expression profiling, and methylation analyses. Such BeadArray™ products include GoldenGate® and Infinium® Genotyping Assays, DASL® and DirectHyb Assays. The assay system 1200 may be configured to scan BeadChips associated with these assays.

Furthermore, the scanner 1202 may be capable of submicron resolution using lasers, optics, and detection systems (Table 2) resulting in reduced scan times while maintaining quality and reproducibility. Exemplary high density BeadChips that may be analyzed by the scanner 1202 are provided in Table 3.

TABLE 2

Scanner Performance Parameters

| | |
|---|---|
| Lasers | A two-laser system with wavelengths at 532 and 660 nm |
| Optical System | Time Delayed Integration (TDI) line scanning and two CCD sensors for high-resolution performance and fast data rate |
| Scanner Resolution | 0.375 micron spatial resolution with dual-channel collection |

TABLE 3

Scanner Array Scan Times

| BeadChip | Scan Time (per sample) | Manual Loading (samples/week) | Automated Loading (samples/week) |
|---|---|---|---|
| HumanOmni1-Quad | 12.5 minutes | 160 | 576 |
| HumanOmniExpress | 5 minutes | 480 | 1,440 |
| Human660W-Quad | 9 minutes | 160 | 800 |
| HumanCytoSNP-12 | 2.9 minutes | 480 | 1,1720 |
| iSelect ® HD | 1.7 minutes | 480 | 3,456 |
| Universal-32* | 0.3 minutes | 1,440 | 1,440 |

*For GoldenGate Indexing ™

The assay system 1200 may provide a streamlined workflow. The assay system 1200 may automate and streamline experimental setup and processing procedures. A sequencing protocol is illustrated in FIG. 53. Libraries can be prepared from nucleic acid samples. The libraries may be prepared in less than six hours with standardized kits. Clonal amplification can be accomplished using a fully automated cBot cluster generation system. The clonal amplification may be completed in less than four hours, with less than 10 minutes of hands-on time. The protocol does not require emulsion PCR. The protocol provides a self-contained system that minimizes handling errors and contamination concerns, eliminating the need for robotics or clean rooms.

FIG. 54 shows various features of the assay system 1200 that may simplify and reduce the hands-on time for user interaction. A touch screen 1206 may provide an interface for setup, including on-screen step-by-step instructions with embedded multimedia help. Pre-configured, plug-and-play reagents 1208 can be loaded into the instrument's chiller compartment. The reagent loading may require only two minutes of hands-on time. Real-time progress indicators provide at-a-glance status reports, and remote monitoring allows progress checks on multiple systems from any browser or internet-enabled phone. A combo drawer 1210 contains dual compartments for array and flow cell loading.

The fluidics device 1204 may be added to an existing microarray scanner 1202 to enable sequencing capabilities. Table 4 lists sequencing performance parameters in accordance with the assay system 1200 of FIGS. 52-54. The fluidics device 1204 may provide the components for performing SBS chemistry, including an integrated paired-end fluidics system. The integrated paired-end fluidics system eliminates the need for a separate external module, and provides seamless second-read sequencing. As such, labs interested in adding sequencing to their research can have greater control over experiments and scheduling without having to rely on large centralized instruments,

TABLE 4

Sequencing Performance Parameters

| | Performance Specification |
|---|---|
| Data Generation | >50 Gb of high-quality data per paired-end flow cell |
| Run Times | 1.5 days for a 36-bp single-read run<br>4 days for a 2 × 50-bp paired-end run<br>8 days for a 2 × 100-bp paired-end run |
| Daily Throughout | Minimum of 6 Gb of high-quality filtered bases per day |
| Samples per Flow Cell | 1-12 samples per flow cell lane (8-96 samples per flow cell) |
| Cluster Density | 260,000-347,000 clusters/mm$^2$<br>250M clusters passing filter per flow cell |

The assay system 1200 may enable several array- and sequencing-based applications. The microarray scanner 1202 may support a number of genotyping, gene expression profiling, and methylation assays. The combination of both short and long-insert paired-end sequencing, coupled with 2×100 bp read lengths and SBS chemistry expands the range of sequencing experiments (Table 5). Low input requirements for both technologies enable a number of applications where sample is limited. Table 6 lists a number of applications that the assay system 1200 may be used to perform.

TABLE 5

Sequencing Application Examples

| Read Length | Small Genome Sequencing | Targeted Resequencing | mRNA-Seq (Discovery) | mRNA-Seq (Profiling) | ChIP-Seq | Small RNA Sequencing |
|---|---|---|---|---|---|---|
| Example | 4 Mb Bacterium >50x coverage | 5 Mb region >75x coverage | 40M* reads per sample | Avg. 5M reads per sample | Avg. 2M reads per sample | 2.5M reads per sample |

TABLE 5-continued

Sequencing Application Examples

| Read Length | 2 × 50 bp | 2 × 75 bp | 2 × 75 bp | 1 × 50 bp | 1 × 35 bp | 1 × 35 bp |
|---|---|---|---|---|---|---|
| Samples per Run | 96 | 96 | 6 | 48 | 96 | 96 |
| Samples per Run | ≤4.5 days | ≤6.5 days | ≤6.5 days | ≤4.5 days | ≤2.5 days | ≤2.5 days |

*Double the reads for paired-end runs

TABLE 6

Diverse Array and Sequencing Applications

| Research Areas | BeadArray Applications | Sequencing Applications |
|---|---|---|
| Whole-Genome Analysis | Whole-Genome Genotyping | Whole-Genome Discovery |
| Copy Number Variation (CNV) | CNV Analysis | CNV Discovery |
| Targeted Genome Analysis | Custom and Focused Genotyping | Targeted Resequencing |
| Gen Regulation and Epigenetic Analysis | Whole-Genome DNA Methylation Profiling | ChIP-Seq, Small RNA Analysis, and Methylation Discovery and Analysis |
| Gene Expression | Whole-Genome Expression Profiling and FFPE Sample Analysis | Transcriptome Discovery and Profiling |
| Cytgenetics | Cytogenetic Analysis | Digital Karyotyping |

The assay system 1200 has a modular configuration that is customizable. The assay system 1200 may allow researchers to modularly build out the system so that it can be customized to meet evolving research needs. Starting with the microarray scanner 1202, the fluidics device 1204, and the cluster generation system can be added to enable next-generation sequencing. For labs that want to optimize sample throughput for array-based studies, the Autoboader2.x and liquid handling robots automate sample loading and preparation to maximize the number of samples that can be processed in a given time frame.

The assay system 1200 includes analysis software and hardware. The analysis software and hardware may contribute to an end-to-end approach. The assay system 1200 may enable researchers to rapidly move from raw data acquisition to publishable, biologically results. The analysis software (e.g., Illumina's GenomeStudio®) provides graphical analysis and interaction with DNA and RNA data. The software includes analytical tools for both sequencing and array-based experiments. The tools may be used in an intuitive user environment.

For primary sequencing data analysis, Illumina's Sequencing Control Software (SCS) may offer real-time analysis processing that automatically produces image intensities and quality-scored base calls directly on the instrument computer. The reads can be aligned to a reference sequence and analyzed using the Pipeline analysis software. For secondary analysis, Consensus Assessment of Sequence and Variation (CASAVA) software allows for rapid alignment, counting, and variant discovery. Secondary data analysis software can be installed on an existing IT infrastructure.

Accordingly, the assay system 1200 of FIGS. 52-54 provides an integrated system for microarray analysis and sequencing thereby enabling a range of applications and flexibility for experimental design. The modular design may allow the system to be built out to evolve with user needs.

In some embodiments, the microarray scanner 1202 and the fluidics device 1204 are coupled to each other through one or more umbilical cables (not shown). An umbilical cable may comprise fluidic lines and/or communication lines (electrical or optical). In some embodiments, the umbilical cable may include only fluidic lines and communication between the microarray scanner 1202 and the fluidics device 1204 may be conducted wirelessly. The different lines of the umbilical cable can be held together by one or more bands or through a common jacket. In embodiments where the microarray scanner 1202 and the fluidics device 1204 are modular, the umbilical cable may have a length that allows the microarray scanner 1202 and the fluidics device 1204 to be moved with respect to each other while maintaining the fluidic and communicative connections.

The umbilical cable may be removably coupled to the microarray scanner 1202 and/or the fluidics device 1204. As such, the microarray scanner 1202 can be used independently for scanning microarrays. When the user desires, the fluidics device 1204 can be provided and attached to the microarray scanner 1202 using the umbilical cable so that the fluidics device 1204 could deliver the solutions to the flow cell in a predetermined manner. To this end, the microarray scanner 1202 may have fluidic ports (or connectors) that the fluidic lines of the umbilical cable removably attach to. The microarray scanner 1202 may also have communication connectors (e.g., optical or electrical) that the communication lines of the umbilical cable removably attach to. In some embodiments, the fluidics device 1204 may have fluidic ports (or connectors) that the fluidic lines of the umbilical cable removably attach to and/or communication connectors that the communication lines of the umbilical cable removably attach to.

The fluidics device 1204 may be configured to hold a tray having, e.g., a plurality of reactant wells. The reactant wells may include various reaction components, such as, but not limited to, one or more samples, polymerases, primers, denaturants, linearization mixes for linearizing DNA, enzymes suitable for a particular assay (e.g., cluster amplification or SBS), nucleotides, cleavage mixes, oxidizing protectants, and other reagents. The fluidics device 1204 may hold all fluids that are necessary to perform a predetermined assay. In particular embodiments, the fluidics device 1204 may hold all reaction components necessary for performing sample analysis (e.g., SBS). The assay may be performed without removing or replacing any of the reactant wells.

Notwithstanding the above, embodiments described herein include assay systems having imaging and fluidic subsystems that are not modular (i.e., removable).

It is to be understood that the above description is intended to be illustrative, and not restrictive. For example, the above-described embodiments (and/or aspects thereof) may be used in combination with each other. In addition, many modifications may be made to embodiments without departing from the of the scope invention in order to adapt a particular situation or material. While the specific components and processes described herein are intended to define the parameters of the various embodiments, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

What is claimed is:

1. An assay instrument for detecting optical signals from samples, comprising:
    a sample stage comprising a first interface and a second interface, the first interface comprising a platform for holding a sample on an open-faced support and for imaging of an external surface and the second interface comprising a platform for holding a sample in a flow cell for imaging of at least one internal surface, wherein the sample stage is configured to couple to the flow cell with fluidics connectors;
    an objective lens positioned proximate to the sample stage for imaging;
    an optical detector for detecting optical signals from the open-faced support and flow cell; and
    a moving mechanism for selectively moving one or more optical components into an optical pathway between the sample stage and the optical detector to either a first configuration for surface-imaging of the open-faced support or a second configuration for imaging the flow cell.

2. The assay instrument of claim 1, further comprising a fluidic network that is configured to couple to the flow cell with fluidics connectors, wherein the fluidic network comprises a fluid storage system for storing reagents for sequencing by synthesis.

3. The assay instrument of claim 1, further comprising a protocol module for instructing the assay instrument to perform a sequencing by synthesis protocol for the flow cell and for instructing the assay instrument to perform a microarray scanning protocol for the open-faced support.

4. The assay instrument of claim 3, wherein the protocol module is configured to operate according to priority statuses of the samples whereby lower priority samples are paused when a schedule conflict arises.

5. The assay instrument of claim 4, wherein a sample in a flow cell has a higher priority than a sample on an open-faced support.

6. The assay instrument of claim 1, wherein a working distance exists between the sample stage and the objective lens, the working distance being less than 5000 microns.

7. The assay instrument of claim 1, wherein the resolution of the assay instrument is sufficient to individually resolve features or sites that are separated by a distance of less than 15 µm.

8. The assay instrument of claim 1, wherein the objective lens comprises
    (i) a collecting end that is configured to be positioned proximate to one of the first and second interfaces on the sample stage and configured to receive optical signals therefrom; and
    (ii) an afocal end configured to transmit the optical signals toward the optical detector, and
    wherein the one or more optical components comprise a first removable path compensator for adjusting an optical path of the optical signals when positioned between the collecting end of the objective lens and the sample.

9. The assay instrument of claim 8, wherein the one or more optical components further comprise a second removable path compensator for adjusting the optical path of the optical signals when located at an afocal position with respect to the objective lens.

10. The assay instrument of claim 9, wherein the moving mechanism includes a transfer device located at a fixed position with respect to the sample stage, the transfer device configured to move the first removable path compensator into and out of an imaging position between the collecting end of the objective lens and the sample stage.

11. The assay instrument of claim 10, wherein the transfer device comprises a platform assembly configured to removably couple the first path compensator to the objective lens, a motor assembly configured to move the sample stage in an x-y direction and also along a z-direction to and from the objective lens, and a bridge member configured to couple the platform assembly to the motor assembly.

12. The assay instrument of claim 9, wherein the first removable path compensator is configured to adjust the optical path between a configuration for imaging the flow cell and a configuration for imaging the open-faced support.

13. The assay instrument of claim 12, wherein the second path compensator is configured to adjust the optical path between a configuration for imaging a top surface of the flow cell and a configuration for imaging a bottom surface of the flow cell.

14. The assay instrument of claim 9, wherein the first path compensator is operatively coupled to the objective lens through magnetic forces.

15. The assay instrument of claim 1, wherein the optical signals propagate in a beam direction, and wherein the one or more optical components comprise an optical device which has a rotation axis and comprises first and second bandpass filters, the rotation axis extending in a non-parallel manner with respect to the beam direction, the first and second bandpass filters having fixed orientations with respect to the rotation axis, the optical device being selectively rotatable about the rotation axis to position at least one of the first and second bandpass filters within the optical path between the optical detector and the objective lens along which the optical signals propagate.

16. The assay instrument of claim 1, wherein portions of the optical signals are directed by the one or more optical components along a first optical path and a second optical path between the optical detector and the objective lens; wherein
    the one or more optical components comprise first and second optical devices located proximate to the first and second optical paths, respectively, each of the first and second optical devices having a rotation axis and comprising a plurality of bandpass filters, the bandpass filters having fixed orientations with respect to the rotation axis, wherein each of the first and second optical devices selectively rotates about the corresponding rotation axis to position at least one of the bandpass filters within the corresponding optical path.

17. The assay instrument of claim 1, wherein
    the one or more optical components comprise a removable optical wedge, which is positioned in the optical path between the optical detector and the objective lens for detecting first optical signals and removed from the optical path for detecting second optical signals, the optical wedge directing the first optical signals when positioned in the optical path so that the first optical signals are incident upon the sample detector, the second optical signals being incident upon the sample detector when the optical wedge is removed from the optical path.

18. The assay instrument of claim 1, further comprising an excitation light source assembly comprising first and second excitation light sources, the first and second excitation light sources configured to excite the sample during separate first and second imaging sessions, respectively, the sample generating corresponding light emissions when excited by each of the first and second excitation light sources.

19. The assay instrument of claim 18, wherein the one or more optical components comprise a beam splitter separating the corresponding light emissions of each of the first and second excitation light sources into reflected and transmitted portions, the transmitted portions of the first and second excitation light sources being directed along a common transmitted optical path, the reflected portions of the first and second excitation light sources being directed along a common reflected optical path.

20. The assay instrument of claim 19, wherein the one or more optical components include a plurality of optical wedges, each of the transmitted and reflected optical paths having an optical wedge that is selectively moveable, wherein the optical wedge of the reflected optical path redirects the reflected portion during the first imaging session and the optical wedge of the transmitted optical path redirects the transmitted portion during the second imaging session.

* * * * *